(12) United States Patent
Basu et al.

(10) Patent No.: US 9,724,367 B2
(45) Date of Patent: Aug. 8, 2017

(54) INJECTABLE FORMULATIONS FOR ORGAN AUGMENTATION

(75) Inventors: Joydeep Basu, Winston-Salem, NC (US); Richard Payne, Winston-Salem, NC (US); Neil F. Robbins, Winston-Salem, NC (US); Oluwatoyin A. Knight, Winston-Salem, NC (US); Deepak Jain, Winston-Salem, NC (US); Craig R. Halberstadt, Winston-Salem, NC (US); Monica A. Serban, Winston-Salem, NC (US)

(73) Assignee: RegenMed (Cayman) LTD., George Town, Grand Cayman (KY)

( * ) Notice: Subject to any disclaimer, the term of this patent is extended or adjusted under 35 U.S.C. 154(b) by 206 days.

(21) Appl. No.: 13/883,433

(22) PCT Filed: Nov. 10, 2011

(86) PCT No.: PCT/US2011/001887
§ 371 (c)(1),
(2), (4) Date: Jul. 26, 2013

(87) PCT Pub. No.: WO2012/064369
PCT Pub. Date: May 18, 2012

(65) Prior Publication Data
US 2013/0330364 A1 Dec. 12, 2013

Related U.S. Application Data

(60) Provisional application No. 61/412,383, filed on Nov. 10, 2010, provisional application No. 61/474,278, filed on Apr. 12, 2011, provisional application No. 61/550,184, filed on Oct. 21, 2011.

(51) Int. Cl.
| | |
|---|---|
| A61F 13/00 | (2006.01) |
| A61K 9/14 | (2006.01) |
| A61K 31/74 | (2006.01) |
| A61K 38/00 | (2006.01) |
| A61K 38/16 | (2006.01) |
| A61K 47/00 | (2006.01) |
| A61K 35/22 | (2015.01) |
| A61L 27/22 | (2006.01) |
| A61L 27/54 | (2006.01) |
| A61K 45/06 | (2006.01) |

(52) U.S. Cl.
CPC ............. *A61K 35/22* (2013.01); *A61K 45/06* (2013.01); *A61L 27/222* (2013.01); *A61L 27/54* (2013.01); *A61L 2400/06* (2013.01); *A61L 2430/26* (2013.01)

(58) Field of Classification Search
None
See application file for complete search history.

(56) References Cited

U.S. PATENT DOCUMENTS

| | | | |
|---|---|---|---|
| 4,377,513 A | 3/1983 | Sugimoto et al. | |
| 4,769,037 A | 9/1988 | Midcalf | |
| 4,935,365 A * | 6/1990 | Nilsson et al. | ............... 435/178 |
| 4,996,154 A | 2/1991 | Gabriels | |
| 5,085,629 A | 2/1992 | Goldberg et al. | |
| 5,092,886 A | 3/1992 | Dobos-Hardy | |
| 5,429,938 A | 7/1995 | Humes | |
| 5,516,680 A | 5/1996 | Naughton et al. | |
| 5,545,131 A | 8/1996 | Davankov | |
| 5,549,674 A | 8/1996 | Humes et al. | |
| 5,798,113 A * | 8/1998 | Dionne et al. | ................ 424/422 |
| 5,854,006 A | 12/1998 | Hanigan et al. | |
| 5,952,226 A | 9/1999 | Aebischer et al. | |
| 5,994,127 A | 11/1999 | Selden et al. | |
| 6,020,200 A | 2/2000 | Enevold | |
| 6,060,270 A | 5/2000 | Humes | |
| 6,129,761 A | 10/2000 | Hubbell | |
| 6,140,039 A | 10/2000 | Naughton et al. | |
| 6,224,893 B1 | 5/2001 | Langer et al. | |
| 6,283,761 B1 | 9/2001 | Joao | |
| 6,306,406 B1 | 10/2001 | Deluca | |
| 6,346,274 B1 | 2/2002 | Koll et al. | |
| 6,365,385 B1 | 4/2002 | Opara | |
| 6,376,244 B1 | 4/2002 | Atala | |
| 6,410,320 B1 | 6/2002 | Humes | |
| 6,548,081 B2 | 4/2003 | Sadozai et al. | |
| 6,576,019 B1 | 6/2003 | Atala | |
| 6,673,339 B1 | 1/2004 | Atala et al. | |
| 6,747,002 B2 | 6/2004 | Cheung et al. | |
| 6,777,205 B1 | 8/2004 | Carcagno et al. | |

(Continued)

FOREIGN PATENT DOCUMENTS

| | | |
|---|---|---|
| CN | 104496 | 8/1990 |
| KR | 20010026239 | 4/2001 |

(Continued)

OTHER PUBLICATIONS

Pisitkun et al. Identification and Proteomic Profiling of Exosomes in Human Urine. PNAS, 2004. 101(36): 13368-13373.*
Heller, Wilfried. The Non-Isothermal Gel-Sol-Gel Transformation of Mixed Gelatin-Methycellulose Systems, Journal of Physical Chemistry, 1941: 45(3):378-388.*
Aboushwareb et al. "Erythropoietin producing cells for potential cell therapy", World Journal Urology 26:295-300, 2008.
Adhirajan et al. "Gelatin microspheres cross-linked with EDC as a drug delivery system for doxycyline: development and characterization", Journal of Microencapsulation 24(7):659-671, 2007.
Aliotta et al. "Microvesicle entry into marrow cells mediates tissue-specific changes in mRNA by direct delivery of mRNA and induction of transcription", Experimental Hematology 38:233-245, 2010.

(Continued)

*Primary Examiner* — Christopher M Babic
*Assistant Examiner* — Kimberly A Aron
(74) *Attorney, Agent, or Firm* — Christopher DeVry; Ginger R. Dreger; Arnold & Porter Kaye Scholer LLP

(57) ABSTRACT

The present invention concerns phase changing injectable formulations for organ augmentation containing active agents, such as bioactive cell populations, and methods of making and using the same.

47 Claims, 26 Drawing Sheets

(56) References Cited

U.S. PATENT DOCUMENTS

| | | | |
|---|---|---|---|
| 6,784,154 B2 | 8/2004 | Westenfelder | |
| 6,827,938 B2 | 12/2004 | Hart et al. | |
| 6,991,652 B2 | 1/2006 | Burg | |
| 7,326,570 B2 | 2/2008 | Nigam et al. | |
| 8,318,484 B2 | 11/2012 | Presnell et al. | |
| 2001/0041718 A1* | 11/2001 | Thompson et al. | 514/317 |
| 2002/0012961 A1* | 1/2002 | Botstein et al. | 435/69.1 |
| 2002/0051808 A1 | 5/2002 | Deluca | |
| 2002/0182254 A1 | 12/2002 | Calias et al. | |
| 2003/0124099 A1 | 7/2003 | Atala | |
| 2004/0122077 A1* | 6/2004 | Walsh | 514/423 |
| 2004/0167634 A1 | 8/2004 | Atala et al. | |
| 2004/0241203 A1* | 12/2004 | Shakesheff et al. | 424/426 |
| 2007/0059293 A1 | 3/2007 | Atala et al. | |
| 2007/0078084 A1 | 4/2007 | Kishore et al. | |
| 2007/0116679 A1 | 5/2007 | Atala | |
| 2007/0128174 A1 | 6/2007 | Kleinsek et al. | |
| 2007/0276507 A1 | 11/2007 | Bertram et al. | |
| 2008/0003292 A1 | 1/2008 | Ahlers et al. | |
| 2008/0103606 A1* | 5/2008 | Berkland et al. | 623/23.72 |
| 2008/0305146 A1 | 12/2008 | Atala et al. | |
| 2010/0104544 A1 | 4/2010 | Atala et al. | |
| 2010/0112062 A1 | 5/2010 | Atala et al. | |
| 2010/0131075 A1 | 5/2010 | Ludlow et al. | |
| 2010/0144902 A1* | 6/2010 | Shu | 514/774 |
| 2010/0215715 A1 | 8/2010 | Han et al. | |
| 2011/0053157 A1 | 3/2011 | Skog et al. | |
| 2011/0117162 A1 | 5/2011 | Presnell et al. | |
| 2013/0149347 A1 | 6/2013 | Presnell et al. | |

FOREIGN PATENT DOCUMENTS

| | | |
|---|---|---|
| WO | WO 90/02796 | 3/1990 |
| WO | WO 90/12604 | 11/1990 |
| WO | WO 92/19195 | 11/1992 |
| WO | WO 93/07913 | 4/1993 |
| WO | WO 95/11048 | 4/1995 |
| WO | WO 96/40175 | 12/1996 |
| WO | WO 00/02600 | 1/2000 |
| WO | WO 01/48153 | 7/2001 |
| WO | WO 01/92322 A1 | 12/2001 |
| WO | WO 02/061053 | 8/2002 |
| WO | WO 03/043674 | 5/2003 |
| WO | WO 2007/035843 | 3/2007 |
| WO | WO 2007/095193 | 8/2007 |
| WO | WO 2008/045498 | 4/2008 |
| WO | WO 2008/098019 | 8/2008 |
| WO | WO 2008/153970 | 12/2008 |
| WO | WO 2010/056328 | 5/2010 |
| WO | WO 2010/056328 A1 | 5/2010 |
| WO | WO 2010/057013 | 5/2010 |
| WO | WO 2010/057015 | 5/2010 |
| WO | WO 2011/140137 | 10/2011 |
| WO | WO 2011/143499 | 11/2011 |
| WO | WO 2011/156642 | 12/2011 |
| WO | WO 2012/064369 | 5/2012 |

OTHER PUBLICATIONS

Amann et al. "Cardiac remodeling in experimental renal failure—an immunohistochemical study", Nephrology Dialysis Transplantation 13:1958-1966, 1998.
Anglani et al. "The renal stem cell system in kidney repair and regeneration", Frontiers Bioscience 13:6395-6405, 2008.
Apak et al. "Comparative evaluation of various total antioxidant capacity assays applied to pehnolic compounds with the CUPRAC assay", Molecules 12:1496-1547, 2007.
Basu et al, "Organ specific regenerative markers in peri-organ adipose: kidney", Lipids in Health and Disease 10:171, 2011.
Base et al. "Functional evaluation of primary renal cell/biomaterial neo-kidney augment prototypes for renal tissue engineering", Cell Transplantation 20:1771-1790, 2011.
Ben-Zeev et al. "Cell-cell and cell-matrix interactions differentially regulate the expression hepatic and cytoskeletal genes in primary cultures of rat hepatocytes", PNAS 85:2161-2165, 1988.
Brenner, BM. "Nephron adaptation to renal injury or ablation", Am. J. Physiol. 249:F324-F337, 1985.
Brown et al. "Characterization of human tubular cell monolayers as a model of proximal tubular xenobiotic handling", Toxicology and Applied Pharmacology 233:428-438, 2008.
Brunskill et al. "Atlas of gene expression in the developing kidney at microanatomic resolution", Dev Cell. 15(5):781-791, 2008.
Castrop, H. "Mediators of tubuloglomerular feedback regulation of glomerular filtration: ATP and adenosine", Acta Physiol. 189:3-14, 2007.
Cenni et al. "Biocompatibility and performance in vitro of a hemostatic gelatin sponge", J Biomater Sci Polym Edn. 11(7): 685-699, 2000.
Chang et al. "In vivo evaluation of a biodegradable EDC/NHS-cross-linked gelatin peripheral nerve guide conduit material", Macromolecular Bioscience 7:500-507, 2007.
Chade et al. "Endothelial progenitor cells restore renal Function in chronic experimental renovascular disease", Circulation 119:547-557, 2009.
Cornwall et al. "Extracellular matrix biomaterials for soft tissue repair", Clin Podiatr Med Surg 26:507-523, 2009.
Database WPI Week 198834, Thomson Scientific, London, GB; XP002671248, Jul. 19, 1988 (Abstract).
Daley, GQ et al. "Realistic prospects for stem cell therapeutics", Hematology 398-418, 2003.
Damink et al. "Cross-linking of dermal sheep collagen using a water-soluble carbodiimide", Biomaterials 17:765-773, 1996.
Djabourov et al. "Thermally reversible gelation of gelatin-water system", American Chemical Society Chapter 14, 1987.
Ding et al. "The bioartificial kidney and bioengineered membranes in acute kidney injury", Nephron Experimental Nephrology 109:e118-e122, 2008.
Donnelly, S. "New insights into renal anemia", Canadian Journal Diabetes 27(2):176-181, 2003.
Dudas et al. "BMP-7 fails to atenuate TGF-beta-1 induced epithelial-to-mesenchymal transition in human proximal tubule epithelial cells", Nephrol Dial Transplant 24(5):1406-1416, 2009.
Eliopoulos et al. "Erythropoietin delivery by genetically engineered bone marrow stromal cells for correction of anemia in mice with chronic renal failure", J Am Soc. Nephrol 17:1576-1584, 2006.
Engvall et al. "Binding of soluble form of fibroblast surface protein, fibronectin, to collagen", International Journal Cancer 20(1):1-5; 1977.
Fisher et al. "Erythropoietin:physiology and pharmacology update", Experimental Biology and Medicine 228:1-14, 2003.
Fontaine et al. "Transplantation of genetically altered hepatocytes using cell-polymer constructs", Transplantation Proceedings 25(1):1002-1004, 1993.
Gagnieu et al. "In vivo biodegradability and biocompatibility of porcine type I atelocollagen newly crosslinked by oxidized glycogen", Bio-Medical Materials Engineering 17:9-18, 2007.
Genestie et al. "Polarity and transport properties of rabbit kidney proximal tubule cells on collagen IV coated porous membranes", Am. J Physiol. 269(1):22-30, 1995.
Griffiths-Jones et al. "MiRBase:microRNA sequences, targets and gene nomenclature", Nucleic Acids Research 34:D140-D144, 2006.
Guo at al. "Cellular maintenance and repair of the kidney", Annu. Rev. Physiol. 72:357-376, 2010.
Guo et al. "miR-15b and miR-16 are implicated in activation of the rat hepatic stellate cell: an essential role for apoptosis", J Hepatology 50(4):766-778, 2009.
Hammerman, M.. "Growing kidneys", Current Opinion Nephrology and Hypertension 10:13-17, 2001.
Held et al. "In vivo genetic selection of renal proximal tubules", Molecular Therapy 13(1):49-58, 2006.
Hills et al. "C-peptide reverses TGF-beta1-induced changes in renal proximal tubular cells: implications for treatment of diabetic neuropathy", Am J Physiol Renal Physiol 296(3):F614-621; 2009.
Hopkins et al. "Stem cell options for kidney disease", Journal of Patholoy 217:265-281, 2009.

(56) References Cited

OTHER PUBLICATIONS

Humes et al. "Initial clinical results of the bioartificial kidney containing human cells in ICU patients with acute renal failure", Kidney International 66:1578-1588, 2004.
Humes et al. "Replacement of renal function in uremic animals with a tissue-engineered kidney", Nature Biotechnology 17:451-455,1999.
Humphreys et al. "Mesenchymal stem cells in acute kidney injury", Annu. Rev. Med. 59:311-325, 2008.
Jarad et al. "Update on the glomerular filtration barrier", Current Opinion in Nephrology and Hypertension 18:226-232, 2009.
Joraku et al. "In vitro generation of three-dimensional renal structures", Methods 47:129-133, 2009.
Kaufman et al. "Compensatory adaptation of structure and function following progressive renal ablation", Kidney International 6:10-17,1974.
Kelley et al. "Tubular cell-enriched subpopulation of primary renal cells improves survival and augments kidney function in rodent model of chronic kidney disease." Am J Physiol Renal Physiol. 299(5):F1026-F1039, 2010.
Kelley et al. "A population of selected renal cells augments renal function and extends survival in the ZSFI model of progressive diabetic nephropathy", Cell Transplantation 22(6):1023-1039, 2013.
Kim et al. "Distinct differentiation properties of human dental pulp cells on collagen, gelatin, and chitosan scaffolds", Oral Surg Oral Med Oral Pathol Oral Radiol Endod 108:e94-100, 2009.
Kim et al. "Kidney tissue reconstruction by fetal kidney cell transplantation: Effect of gestation stage of fetal kidney cells", Stem Cells 25:1393-1401, 2007.
Kimura et al. "Adipose tissue formation in collagen scaffolds with different biodegradabilities", J Biomater Sci Polym Ed 21(4):463-476, 2010.
Kommareddy et al. "Poly (ethylene glycol) modified thiolated gelatin nanoparticles for glutathione-responsive intracellular DNA delivery", Nanomedicine 3(1):32-42, 2007.
Kreisberg et al. "Separation of proximal tubule cells from suspensions of rat kidney cells in density gradients of ficoll in tissue culture medium", Am J. Pathol. 86:591-602, 1977.
Krantz, SB "Erythropoietin", Blood 77(3):419-434, 1991.
Kucic et al. "Mesenchymal stromal cells genetically engineered to overexpress IGF-I enhance cell-based gene therapy of renal failure-induced anemia", Am. J. Physiol. Renal Physiol. 295:F488-F496, 2008.
Kuijpers et al. "Cross-linking and characterisation of gelatin matrices for biomedical applications", J. Biomater Sci. Polymer Edn. 11(3):225-243, 2000.
Kurtz et al. "Renal mesangial cell cultures as a model for study of erythropoietin production", Proc. Natl. Acad. Sci. USA 80:4008-4011, 1983.
Lai et al. "Biocompatibility of chemically cross-linked gelatin hydrogels for ophthalmic use", J Mater Sci: Mater Med 21:1899-1911, 2010.
Lee et al. "Biomedical applications of collagen", International Journal of Pharmaceutics 221:1-22 , 2001.
Li et al. "Aberrant planar cell polarity induced by urinary tract obstruction", Am J Physiol Renal Physiology 297(6)1:F1526-33, 2009.
Lie et al. "Wnt signalling regulates adult hippocampal neurogenesis", Nature 437(7063):1370-1375, 2005.
Lin et al. "Intrarenal cells , not bone marrow-derived cells are the major source for regeneration in postischemic kidney", Journal Clinical Investigation 115(7):1756-1764, 2005.
Marshall et al. "Increasing renal mass improves survival in anephric rats following metanephros transplantation", Experimental Physiology 92.1:263-271, 2007.
Marquez et al. "MicroRNA-21 is upregulated during the proliferative phase of liver regeneration, targets Pellino~l, and inhibits NF-kB signaling", Am J Physiol Gastrointest Liver Physiol 298(4):G535-41, 2010.

Nangaku M. "Chronic hypoxia and tubulointerstitial injury: a final common pathway to end stage renal failure", J. Am Soc Nephrol 17:17-25, 2006.
Newsome, "Yet another role for mesenchymal stem cells?", Transplantation 85(11):1548-1549, 2008.
Ormrod et al. "Experimental Uremia: description of a model producing varying degrees of stable uremia", Nephron 26:249-254, 1980.
Patschan et al. "Therapeutic use of stem and endothelial progenitor cells in acute renal injury: ça ira", Current Opinion in Pharmacology 6:176-183, 2006.
Pieper et al. "Development of tailor-made collagen-glycosaminoglycan matrices: EDC/NHS crosslinking and ultrastructural aspects", Biomaterials 21(6):581-593, 2000.
Platt et al. "Experimental renal failure", Department of Medicine, University of Manchester 217-231, 1952.
Plotkin et al. "Mesenchymal cells from adult kidney support angiogenesis and differentiate into multiple interstitial cell types including erythropoietinproducing fibroblasts", Am J. Physiol Renal 291:F902-F912, 2006.
Powe et al. "Public health surveillance of CKD: Principles, steps and challenges", Am. J Kidney Diseases 53(S3): S37-S45, 2009.
Presnell et al. "Isolation, characterization, and expansion methods for defined primary renal cell populations from rodent, canine, and human normal and diseased kidneys", Tissue Engineering Part C,17(3):261-273, 2011.
Prodromidi et al. "Bone marrow-derived cells contribute to podocyte regeneration and amelioration of renal disease in a mouse model of alport syndrome", Stem Cells 24:2448-2455, 2006.
Rangan et al. "NF-kappaB signaling in chronic kidney disease", Frontiers in Bioscience 14:3496-3522 , 2009.
Rerolle et al. "Plasminogen activator inhibitor type 1 is a potential target in renal fibrogenesis", Kidney International 58:1841-1850, 2000.
Rinsch et al. "Delivery of erythropoietin by encapsulated myoblasts in a genetic model of severe anemia", Kidney International 62:1395-1401, 2002.
Rohanizadeh et al. "Gelatin sponges (Gelfoam) as a scaffold for osteoblasts", J Mater Sci Mater Med 19(3):1173-1182, 2008.
Rossert et al. "Anemia management and the delay of chronic renal failure progression", J. Am Soc Nephrol 14:S173-S177, 2003.
Saal et al. "MicroRNAs and the kidney: coming of age", Current Opinion in Nephrology and Hypertension 18:317-323, 2009.
Sakai et al. "An injectable, in situ enzymatically gellable, gelatin derivative for drug delivery and tissue engineering", Biomaterials 30:3371-3377, 2009.
Sanz et al. "NF-kappa B in renal inflammation", J Am Soc Nephrol 21(8):1254-1262, 2010.
Sehgal et al. "Collagen-coated microparticles in drug delivery", Expert Opinion Drug Delivery 6(7):687-695, 2009.
Seo et al. "Positive feedback loop between plasminogen activator inhibitor-1 and transforming growth factor-beta 1 during renal fibrosis in diabetes", Am J Nephrol 30(6):481-490, 2009.
Sugimoto et al. "Bone-marrow-derived stem cells repair basement membrane collagen defects and reverse genetic kidney disease", PNAS 103(19):7321-7326, 2006.
Sutter et al. "Recombinant gelatin hydrogels for the sustained release of proteins", J Control Release 119 (3):301-312, 2007.
Takemoto et al. "Preparation of collagen/gelatin sponge scaffold for sustained release of bFGF", Tissue Engineering Part A 14(10):1629-1638, 2008.
Taganov et al. "NF-kB-dependent induction of microRNA miR-146, an inhibitor targeted to signaling proteins of innate immune responses", PNAS 103(33):12481-12486, 2006.
Vandelli et al. "Gelatin microspheres crosslinked with D, L-glyceraldehyde as a potential drug delivery system: preparation, characterization, in vitro and in vivo studies", International Journal of Pharmaceutics 215:175-184, 2001.
Vandelli et al. "Microwave-treated gelatin microspheres as drug delivery system", Journal of Controlled Release 96:67-84, 2004.
Waksman et al. "The antigenicity of collagen", J Immunol 63(4):427-433, 1949.

(56) References Cited

OTHER PUBLICATIONS

Wang et al. "Export of microRNAs and microRNA-protective protein by mammalian cells", Nucleic Acids Research 38(20):7248-7259, 2010.

Willert et al. "Wnt proteins are lipid-modified and can act as stem cell growth factors", Nature. 423(6938):448-452, 2003.

Xia et al. "MicroRNA-15b regulates cell cycle progression by targeting cyclins in glioma cells", Biochem Biophys Res Commun. 380 (2):205-10, 2009.

Yokoo et al. "Generation of a transplantable erythropoietin-producer derived from human mesenchymal stem cells", Transplantation 85:1654-1658, 2008.

Yokoo et al. "Xenobiotic kidney organogenesis from human mesenchymal stem cells using a growing rodent embryo", J. Am. Soc. Nephrol. 17:1026-1034, 2006.

Young et al. "Gelatin as a delivery vehicle for the controlled release of bioactive molecules", Journal Control Release 109 (1-3):256-274, 2005.

Zeisberg et al. "Renal fibrosis. Extracellular matrix microenvironment regulates migratory behavior of activated tubular epithelial cells", American J Pathology 160(6):2001-2008, 2002.

Zeisberg et al. "BMP-7 counteracts TGF-β1-induced epithelial-to-mesenchymal transition and reverses chronic renal injury", Nature Medicine 9(7):964-968, 2003.

Zhou et al. "Urinary exosomal transcription factors, a new class of biomarkers for renal disease", Kidney International 74(5):613-621, 2008.

Adhirajan et al., "Gelatin microspheres cross-linked with EDC as a drug delivery system for doxyxyline: development and characterization," J Microencapsul. 2007, vol. 24, No. 7, pp. 647-659.

Goh et al., "Limited beneficial effects of perfluorocarbon emulsions on encapsulated cells in culture: experimental and modeling studies," J Biotechnol. 2010, vol. 150, No. 2, pp. 232-239.

Tan et al., "Injectable, Biodegradable Hydrogels for Tissue Engineering Applications," Materials 2010, vol. 3, pp. 1746-1767.

Zandi, M., "Studies on the Gelation of Gelatin Solutions and on the Use of Resulting Gels for Medical Scaffolds," Dissertation, University of Duisburg-Essen, Feb. 18, 2008.

\* cited by examiner

Weibull(87.3028,1.35014)

Fitted 2 parameter Weibull

Parameter Estimates

| Type | Parameter | Estimate | Lower 95% | Upper 95% |
|---|---|---|---|---|
| Scale | $\alpha$ | 87.302843 | 81.449346 | 93.492869 |
| Shape | $\beta$ | 1.3501387 | 1.2643035 | 1.4383645 |

-2log(Likelihood) = 5304.26509923386

Goodness-of-Fit Test

Cramer-von Mises W Test

| W-Square | Prob>W^2 |
|---|---|
| 0.712984 | > 0.2500 |

Note: Ho = The data is from the Weibull distribution. Small p-values reject Ho.

A

B

A.

B.

A

B

A

B

INJECTABLE FORMULATIONS FOR ORGAN AUGMENTATION

CROSS REFERENCE TO RELATED APPLICATION

This application is a US National Stage application claiming the benefit under 35 USC §371 of PCT/US2011/01887 filed Nov. 10, 2011, which claims the benefit under 35 USC §119 of U.S. Provisional Application Nos. 61/412,383 filed Nov. 10, 2010, 61/474,278 filed Apr. 12, 2011, and 61/550,184 filed Oct. 21, 2011. The disclosures of the foregoing applications are incorporated herein by reference in their entirety.

FIELD OF THE INVENTION

The present invention relates to therapeutic formulations of active agents, such as bioactive cell populations, and methods of preparing the same, as well as methods of administering the formulations to a subject in need.

BACKGROUND OF THE INVENTION

Collagen and gelatin-based biomaterials have been successfully employed for a variety of tissue engineering applications (Rohanizadeh et al. J Mater Sci Mater Med 2008; 19: 1173-1182; Takemoto et al. Tissue Eng Part A 2008; 14: 1629-1638; Young et al. J Control Release 2005; 109: 256-274). Both of these macromolecules are characterized by excellent biocompatibility and low antigenicity (Cenni et al. J Biomater Sci Polym Ed 2000; 11: 685-699; Lee et al. Int J Pharm 2001; 221: 1-22; Waksman et al. J Immunol 1949; 63: 427-433); however, since gelatin is obtained by the hydrolysis of collagen, it has certain advantages over the latter: (a) it is readily available and easy to use; (b) offers options relative to molecular weight and bloom (i.e. control over physical properties); and (c) is more flexible towards chemical modification and more straightforward to manufacture. Moreover, from a biological standpoint, gelatin maintains cytocompatibility and cell adherence properties similar to collagen Engvall et al. Int J Cancer 1977; 20:1-5; Kim et al. Oral Surg Oral Med Oral Pathol Oral Radiol Endod 2009; 108: e94-100).

Various methods have been reported for the crosslinking of these macromolecules for the purpose of delaying their biodegradation to prolong their in vivo residence (in tissue engineering applications) or tailoring their drug releasing capacity (when used as drug carriers). Numerous methods have been published for chemical or photochemical crosslinking of collagen or gelatin (Adhirajan et al. J Microencapsul 2007; 24: 647-659; Chang et al. Macromol Biosci 2007; 7: 500-507; Gagnieu et al. Biomed Mater Eng 2007; 17: 9-18; Kimura et al. J Biomater Sci Polym Ed 2010; 21: 463-476; Ma et al. J Biomed Mater Res A 2004; 71: 334-342; Vandelli et al. Int J Pharm 2001; 215: 175-184; Vandelli et al. J Control Release 2004; 96: 67-84). The majority of these procedures are targeted to reduce the susceptibility of these biomaterials to enzymatic degradation and to extend their in vivo residence time (Chang et al. supra 2007; Ma et al. supra 2004). Other crosslinking methods are typically employed to yield gelatin or collagen-based biomaterials suitable as slow release drug, protein or nucleic acid carriers (Kimura supra 2010; Vandelli supra 2004; Kommareddy et al. Nanomedicine 2007; 3: 32-42; Sehgal et al. Expert Opin Drug Deliv 2009; 6: 687-695; Sutter et al. J Control Release 2007; 119: 301-312). A widely used crosslinking agent class for collagen and gelatin as well as other tissue engineering-compatible systems is the carbodiimides (Adhirajan supra 2007; Olde Damink et al. Biomaterials 1996; 17: 765-773; Pieper et al. Biomaterials 2000; 21: 581-593; Cornwell et al. Clin Podiatr Med Surg 2009; 26: 507-523). These molecules are known as zero-length crosslinkers and act by mediating the formation of amide bonds between carboxyl and primary amine functionalities present on the species to be crosslinked. In addition, carbodiimides are less cytotoxic compared to other common crosslinking agent (e.g. glutaraldehyde) (Lai et al. J Mater Sci Mater Med 2010; 21: 1899-1911). Glutaraldehylde is used as a crosslinker in Cultispher™ beads. Burg U.S. Pat. No. 6,991,652 describes tissue engineering composites containing three-dimensional support constructs for cells that may be delivered to a subject.

Regenerative medicine technologies provide next-generation therapeutic options for chronic kidney disease (CKD). Presnell et al. WO/2010/056328 and Hagan et al. PCT/US2011/036347 describe isolated bioactive renal cells, including tubular and erythropoietin (EPO)-producing kidney cell populations, and methods of isolating and culturing the same, as well as methods of treating a subject in need with the cell populations.

There is a need for therapeutic formulations that are suitable for delivery of active agents, such as for example, bioactive cells in tissue engineering and regenerative medicine applications, to subjects in need.

SUMMARY OF THE INVENTION

In one aspect, the present invention provides injectable, therapeutic formulations containing active agents, e.g., bioactive cells. In one embodiment, the injectable formulation comprises bioactive cells and a temperature-sensitive cell-stabilizing biomaterial. In another embodiment, the a temperature-sensitive cell-stabilizing biomaterial maintains (i) a substantially solid state at about 8° C. or below and/or (ii) a substantially liquid state at ambient temperature or above. In one other embodiment, the bioactive cells comprise renal cells, as described herein. In another embodiment, the bioactive cells are substantially uniformly dispersed throughout the volume of the cell-stabilizing biomaterial. In other embodiments, the biomaterial has a solid-to-liquid transitional state between about 8° C. and about ambient temperature or above. In one embodiment, the substantially solid state is a gel state. In another embodiment, the cell-stabilizing biomaterial comprises a hydrogel. In one other embodiment, the hydrogel comprises gelatin. In other embodiments, the gelatin is present in the formulation at about 0.5% to about 1% (w/v). In one embodiment, the gelatin is present in the formulation at about 0.75% (w/v). In another embodiment, the formulation further includes a cell viability agent. In one other embodiment, the cell viability agent comprises an agent selected from the group consisting of an antioxidant, an oxygen carrier, an immunomodulatory factor, a cell recruitment factor, a cell attachment factor, an anti-inflammatory agent, an immunosuppressant, an angiogenic factor, and a wound healing factor. In some embodiments, the cell viability agent is an antioxidant. In one embodiment, the antioxidant is 6-hydroxy-2,5,7,8-tetramethylchroman-2-carboxylic acid. In another embodiment, the 6-hydroxy-2,5,7,8-tetramethylchroman-2-carboxylic acid is present at about 50 µM to about 150 µM. In one other embodiment, the 6-hydroxy-2,5,7,8-tetramethylchroman-2-carboxylic acid is present at about 100 µM. In some embodiments, the cell viability agent is an oxygen carrier. In one embodiment, the oxygen carrier is a perfluorocarbon. In other embodiments, the cell viability agent is an immunomodulatory agent. In one embodiment, the cell viability agent is an immunosuppressant.

In another aspect, the present invention provides injectable, therapeutic formulations containing bioactive renal cells. In one embodiment, the formulation comprises bioactive renal cells, about 0.75% (w/v) gelatin, and about 100 µM 6-hydroxy-2,5,7,8-tetramethylchroman-2-carboxylic acid, wherein the formulation has (i) a substantially solid state at about 8° C. or below, and (ii) a substantially liquid state at ambient temperature or above. In another embodiment, the bioactive renal cells are substantially uniformly dispersed throughout the volume of the cell-stabilizing biomaterial. In one other embodiment, the biomaterial comprises a solid-to-liquid transitional state between about 8° C. and about ambient temperature. In other embodiments, the substantially solid state is a gel state. In some embodiments, the formulation further includes a cell viability agent. In yet another embodiment, the cell viability agent comprises an agent selected from the group consisting of an antioxidant, an oxygen carrier, an immunomodulatory factor, a cell recruitment factor, a cell attachment factor, an anti-inflammatory agent, an angiogenic factor, and a wound healing factor. In one embodiment, the cell viability agent is an oxygen carrier. In another embodiment, the oxygen carrier is a perfluorocarbon. In one other embodiment, the cell viability agent is an immunomodulatory agent. In other embodiments, the cell viability agent is an immunosuppressant.

In one other aspect, the present invention provides a formulation described herein that further includes biocompatible beads. In one embodiment, the biocompatible beads comprise a biomaterial. In another embodiment, the beads are crosslinked. In one other embodiment, the crosslinked beads have a reduced susceptibility to enzymatic degradation as compared to non-crosslinked biocompatible beads. In other embodiments, the crosslinked beads are carbodiimide-crosslinked beads. In one embodiment, the carbodiimide is selected from the group consisting of 1-Ethyl-3-[3-dimethylaminopropyl] carbodiimide hydrochloride (EDC), DCC—N,N'-dicyclohexylcarbodiimide (DCC), and N,N'-Diisopropylcarbodiimide (DIPC). In another embodiment, the carbodiimide is 1-Ethyl-3-[3-dimethylaminopropyl] carbodiimide hydrochloride (EDC). In one other embodiment, the crosslinked beads comprise a reduced number of free primary amines as compared to non-crosslinked beads. In other embodiments, the number of free primary amines is detectable spectrophotometrically at about 355 nm. In some embodiments, the beads are seeded with the bioactive cells. In one embodiment, the bioactive cells are renal cells. In another embodiment, the formulation further comprises additional biocompatible beads that comprise a temperature-sensitive biomaterial that maintains (i) a substantially solid state at ambient temperature or below, and (ii) a substantially liquid state at about 37° C. or above. In one other embodiment, the biomaterial of the beads comprises a solid-to-liquid transitional state between ambient temperature and about 37° C. In other embodiments, the substantially solid state is a gel state. In one embodiment, the biomaterial of the beads comprises a hydrogel. In another embodiment, the hydrogel comprises gelatin. In one other embodiment, the beads comprise gelatin at about 5% (w/v) to about 10% (w/v). In some embodiments, the additional biocompatible beads are spacer beads. In other embodiments, the spacer beads are not seeded with bioactive cells.

In another aspect, the formulations of the present invention contain products secreted by a renal cell population. In one embodiment, the formulations comprise products secreted by a renal cell population and/or bioactive cells. In one other embodiment, the bioactive cells are renal cells. In another embodiment, the products comprise one or more of paracrine factors, endocrine factors, and juxtacrine factors. In one other embodiment, the products comprise vesicles. In other embodiments, the vesicles comprise microvesicles. In one embodiment, the vesicles comprise exosomes. In another embodiment, the vesicles comprise a secreted product selected from the group consisting of paracrine factors, endocrine factors, juxtacrine factors, and RNA.

DETAILED DESCRIPTION OF THE INVENTION

Figure 1:
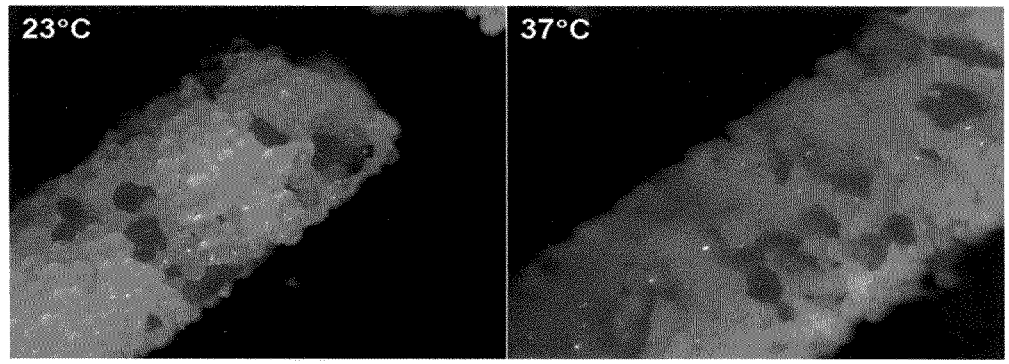
FIG. 1. Temperature responsiveness of uncrosslinked gelatin beads.

The present invention is directed to therapeutic formulations for active agents, such as bioactive cells, as well as methods of preparing the same and methods of treating a subject in need with the formulations. The bioactive cell formulations may be suitable for heterogenous mixtures or fractions of bioactive renal cells (BRCs). The bioactive renal cells may be isolated renal cells including tubular and erythropoietin (EPO)-producing kidney cells. The BRC cell populations may include enriched tubular and EPO-producing cell populations. The BRCs may be derived from or are themselves renal cell fractions from healthy individuals. In addition, the present invention provides renal cell fractions obtained from an unhealthy individual that may lack certain cellular components when compared to the corresponding renal cell fractions of a healthy individual, yet still retain therapeutic properties. The present invention also provides therapeutically-active cell populations lacking cellular components compared to a healthy individual, which cell populations can be, in one embodiment, isolated and expanded from autologous sources in various disease states.

Although bioactive cell formulations are described herein, the present invention contemplates formulations containing a variety of other active agents. Other suitable active agents include, without limitation, cellular aggregates, acellular biomaterials, secreted products from bioactive cells, large and small molecule therapeutics, as well as combinations thereof. For example, one type of bioactive cells may be combined with biomaterial-based microcarriers with or without therapeutic molecules or another type of bioactive cells, unattached cells may be combined with acellular particles.

1. Definitions

Unless defined otherwise, technical and scientific terms used herein have the same meaning as commonly understood by one of ordinary skill in the art to which this invention belongs. *Principles of Tissue Engineering*, 3$^{rd}$ Ed. (Edited by R Lanza, R Langer, & J Vacanti), 2007 provides one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

The term "cell population" as used herein refers to a number of cells obtained by isolation directly from a suitable tissue source, usually from a mammal. The isolated cell population may be subsequently cultured in vitro. Those of ordinary skill in the art will appreciate that various methods for isolating and culturing cell populations for use with the present invention and various numbers of cells in a cell population that are suitable for use in the present invention. A cell population may be an unfractionated, heterogeneous cell population derived from an organ or tissue, e.g., the kidney. For example, a heterogeneous cell population may be isolated from a tissue biopsy or from whole organ tissue. Alternatively, the heterogeneous cell population may be derived from in vitro cultures of mammalian cells, established from tissue biopsies or whole organ tissue. An unfractionated heterogeneous cell population may also be referred to as a non-enriched cell population. In one embodiment, the cell populations contain bioactive cells.

The term "native organ" shall mean the organ of a living subject. The subject may be healthy or un-healthy. An unhealthy subject may have a disease associated with that particular organ.

The term "native kidney" shall mean the kidney of a living subject. The subject may be healthy or un-healthy. An unhealthy subject may have a kidney disease.

The term "regenerative effect" shall mean an effect which provides a benefit to a native organ, such as the kidney. The effect may include, without limitation, a reduction in the degree of injury to a native organ or an improvement in, restoration of, or stabilization of a native organ function.

Renal injury may be in the form of fibrosis, inflammation, glomerular hypertrophy, etc. and related to a disease associated with the native organ in the subject.

The term "admixture" as used herein refers to a combination of two or more isolated, enriched cell populations derived from an unfractionated, heterogeneous cell population. According to certain embodiments, the cell populations of the present invention are renal cell populations.

An "enriched" cell population or preparation refers to a cell population derived from a starting organ cell population (e.g., an unfractionated, heterogeneous cell population) that contains a greater percentage of a specific cell type than the percentage of that cell type in the starting population. For example, a starting kidney cell population can be enriched for a first, a second, a third, a fourth, a fifth, and so on, cell population of interest. As used herein, the terms "cell population", "cell preparation" and "cell prototype" are used interchangeably.

In one aspect, the term "enriched" cell population as used herein refers to a cell population derived from a starting organ cell population (e.g., a cell suspension from a kidney biopsy or cultured mammalian kidney cells) that contains a percentage of cells capable of producing EPO that is greater than the percentage of cells capable of producing EPO in the starting population. For example, the term "B4" is a cell population derived from a starting kidney cell population that contains a greater percentage of EPO-producing cells, glomerular cells, and vascular cells as compared to the starting population. The cell populations of the present invention may be enriched for one or more cell types and depleted of one or more other cell types. For example, an enriched EPO-producing cell population may be enriched for interstitial fibroblasts and depleted of tubular cells and collecting duct epithelial cells relative to the interstitial fibroblasts and tubular cells in a non-enriched cell population, i.e. the starting cell population from which the enriched cell population is derived. In all embodiments citing EPO-enriched or "B4" populations, the enriched cell populations are heterogeneous populations of cells containing cells that can produce EPO in an oxygen-regulated manner, as demonstrated by oxygen-tunable EPO expression from the endogenous native EPO gene.

In another aspect, an enriched renal cell population, which contains a greater percentage of a specific cell type, e.g., vascular, glomerular, or endocrine cells, than the percentage of that cell type in the starting population, may also lack or be deficient in one or more specific cell types, e.g., vascular, glomerular, or endocrine cells, as compared to a starting kidney cell population derived from a healthy individual or subject. For example, the term "B4'," or B4 prime," in one aspect, is a cell population derived from a starting kidney cell population that lacks or is deficient in one or more cell types, e.g., vascular, glomerular or endocrine, depending on the disease state of the starting specimen, as compared to a healthy individual. In one embodiment, the B4' cell population is derived from a subject having chronic kidney disease. In one embodiment, the B4' cell population is derived from a subject having focal segmental glomerulosclerosis (FSGS). In another embodiment, the B4' cell population is derived from a subject having autoimmune glomerulonephritis. In another aspect, B4' is a cell population derived from a starting cell population including all cell types, e.g., vascular, glomerular, or endocrine cells, which is later depleted of or made deficient in one or more cell types, e.g., vascular, glomerular, or endocrine cells. In yet another aspect, B4' is a cell population derived from a starting cell population including all cell types, e.g., vascular, glomerular, or endocrine cells, in which one or more specific cell types e.g., vascular, glomerular, or endocrine cells, is later enriched. For example, in one embodiment, a B4' cell population may be enriched for vascular cells but depleted of glomerular and/or endocrine cells. In another embodiment, a B4' cell population may be enriched for glomerular cells but depleted of vascular and/or endocrine cells. In another embodiment, a B4' cell population may be enriched for endocrine cells but depleted of vascular and/or glomerular cells. In another embodiment, a B4' cell population may be enriched for vascular and endocrine cells but depleted of glomerular cells. In preferred embodiments, the B4' cell population, alone or admixed with another enriched cell population, e.g., B2 and/or B3, retains therapeutic properties. A B4' cell population, for example, is described herein in the Examples, e.g., Examples 11-13.

In another aspect, an enriched cell population may also refer to a cell population derived from a starting kidney cell population as discussed above that contains a percentage of cells expressing one or more vascular, glomerular and proximal tubular markers with some EPO-producing cells that is greater than the percentage of cells expressing one or more vascular, glomerular and proximal tubular markers with some EPO-producing cells in the starting population. For example, the term "B3" refers to a cell population derived from a starting kidney cell population that contains a greater percentage of proximal tubular cells as well as vascular and glomerular cells as compared to the starting population. In one embodiment, the B3 cell population contains a greater percentage of proximal tubular cells as compared to the starting population but a lesser percentage of proximal tubular cells as compared to the B2 cell population. In another embodiment, the B3 cell population contains a greater percentage of vascular and glomerular cells markers with some EPO-producing cells as compared to the starting population but a lesser percentage of vascular and glomerular cells markers with some EPO-producing cells as compared to the B4 cell population.

In another aspect, an enriched cell population may also refer to a cell population derived from a starting kidney cell population as discussed above that contains a percentage of cells expressing one or more tubular cell markers that is greater than the percentage of cells expressing one or more tubular cell markers in the starting population. For example, the term "B2" refers to a cell population derived from a starting kidney cell population that contains a greater percentage of tubular cells as compared to the starting population. In addition, a cell population enriched for cells that express one or more tubular cell markers (or "B2") may contain some epithelial cells from the collecting duct system. Although the cell population enriched for cells that express one or more tubular cell markers (or "B2") is relatively depleted of EPO-producing cells, glomerular cells, and vascular cells, the enriched population may contain a smaller percentage of these cells (EPO-producing, glomerular, and vascular) in comparison to the starting population. In general, a heterogeneous cell population is depleted of one or more cell types such that the depleted cell population contains a lesser proportion of the cell type(s) relative to the proportion of the cell type(s) contained in the heterogeneous cell population prior to depletion. The cell types that may be depleted are any type of kidney cell. For example, in certain embodiments, the cell types that may be depleted include cells with large granularity of the collecting duct and tubular system having a density of <about 1.045 g/ml, referred to as "B1". In certain other embodiments, the cell types that may be depleted include debris and small cells of low granularity and viability having a density of >about 1.095 g/ml, referred to as "B5". In some embodiments, the cell population enriched for tubular cells is relatively depleted of all of the following: "B1", "B5", oxygen-tunable EPO-expressing cells, glomerular cells, and vascular cells.

The term "hypoxic" culture conditions as used herein refers to culture conditions in which cells are subjected to a reduction in available oxygen levels in the culture system relative to standard culture conditions in which cells are cultured at atmospheric oxygen levels (about 21%). Non-hypoxic conditions are referred to herein as normal or normoxic culture conditions.

The term "oxygen-tunable" as used herein refers to the ability of cells to modulate gene expression (up or down) based on the amount of oxygen available to the cells. "Hypoxia-inducible" refers to the upregulation of gene expression in response to a reduction in oxygen tension (regardless of the pre-induction or starting oxygen tension).

The term "biomaterial" as used herein refers to a natural or synthetic biocompatible material that is suitable for introduction into living tissue. A natural biomaterial is a material that is made by or originates from a living system. Synthetic biomaterials are materials which are not made by or do not originate from a living system. The biomaterials disclosed herein may be a combination of natural and synthetic biocompatible materials. As used herein, biomaterials include, for example, polymeric matrices and scaffolds. Those of ordinary skill in the art will appreciate that the biomaterial(s) may be configured in various forms, for example, as porous foam, gels, liquids, beads, solids, and may comprise one or more natural or synthetic biocompatible materials. In one embodiment, the biomaterial is the liquid form of a solution that is capable of becoming a hydrogel.

The term "modified release" or the equivalent terms "controlled release", "delayed release", or "slow release" refer to formulations that release an active agent, such as bioactive cells, over time or at more than one point in time following administration to an individual. Modified release of an active agent, which can occur over a range of desired times, e.g., minutes, hours, days, weeks, or longer, depending upon the formulation, is in contrast to standard formulations in which substantially the entire dosage unit is available immediately after administration. For tissue engineering and regenerative medicine applications, preferred modified release formulations provide for the release of an active agent at multiple time points following local administration (e.g., administration of an active agent directly to a solid organ). For example, a modified release formulation of bioactive cells would provide an initial release of cells immediately at the time of administration and a later, second release of cells at a later time. The time delay for the second release of an active agent may be minutes, hours, or days after the initial administration. In general, the period of time for delay of release corresponds to the period of time that it takes for a biomaterial carrier of the active agent to lose it structural integrity. The delayed release of an active agent begins as such integrity begins to degrade and is completed by the time integrity fails completely. Those of ordinary skill in the art will appreciate other suitable mechanisms of release.

The term "anemia" as used herein refers to a deficit in red blood cell number and/or hemoglobin levels due to inadequate production of functional EPO protein by the EPO-producing cells of a subject, and/or inadequate release of EPO protein into systemic circulation, and/or the inability of erythroblasts in the bone marrow to respond to EPO protein.

A subject with anemia is unable to maintain erythroid homeostasis. In general, anemia can occur with a decline or loss of kidney function (e.g., chronic renal failure), anemia associated with relative EPO deficiency, anemia associated with congestive heart failure, anemia associated with myelo-suppressive therapy such as chemotherapy or anti-viral therapy (e.g., AZT), anemia associated with non-myeloid cancers, anemia associated with viral infections such as HIV, and anemia of chronic diseases such as autoimmune diseases (e.g., rheumatoid arthritis), liver disease, and multi-organ system failure.

The term "EPO-deficiency" refers to any condition or disorder that is treatable with an erythropoietin receptor agonist (e.g., recombinant EPO or EPO analogs), including anemia.

The term "organ-related disease" as used herein refers to disorders associated with any stage or degree of acute or chronic organ failure that results in a loss of the organ's ability to perform its function.

The term "kidney disease" as used herein refers to disorders associated with any stage or degree of acute or chronic renal failure that results in a loss of the kidney's ability to perform the function of blood filtration and elimination of excess fluid, electrolytes, and wastes from the blood. Kidney disease also includes endocrine dysfunctions such as anemia (erythropoietin-deficiency), and mineral imbalance (Vitamin D deficiency). Kidney disease may originate in the kidney or may be secondary to a variety of conditions, including (but not limited to) heart failure, hypertension, diabetes, autoimmune disease, or liver disease. Kidney disease may be a condition of chronic renal failure that develops after an acute injury to the kidney. For example, injury to the kidney by ischemia and/or exposure to toxicants may cause acute renal failure; incomplete recovery after acute kidney injury may lead to the development of chronic renal failure.

The term "treatment" refers to both therapeutic treatment and prophylactic or preventative measures for kidney disease, anemia, EPO deficiency, tubular transport deficiency, or glomerular filtration deficiency wherein the object is to reverse, prevent or slow down (lessen) the targeted disorder. Those in need of treatment include those already having a kidney disease, anemia, EPO deficiency, tubular transport deficiency, or glomerular filtration deficiency as well as those prone to having a kidney disease, anemia, EPO deficiency, tubular transport deficiency, or glomerular filtration deficiency or those in whom the kidney disease, anemia, EPO deficiency, tubular transport deficiency, or glomerular filtration deficiency is to be prevented. The term "treatment" as used herein includes the stabilization and/or improvement of kidney function.

The term "in vivo contacting" as used herein refers to direct contact in vivo between products secreted by an enriched population of cells and a native organ. For example, products secreted by an enriched population of renal cells (or an admixture or construct containing renal cells/renal cell fractions) may in vivo contact a native kidney. The direct in vivo contacting may be paracrine, endocrine, or juxtacrine in nature. The products secreted may be a heterogeneous population of different products described herein.

The term "ribonucleic acid" or "RNA" as used herein refers to a chain of nucleotide units where each unit is made up of a nitrogenous base, a ribose sugar, and a phosphate. The RNA may be in single or double stranded form. The RNA may be part of, within, or associated with a vesicle. The vesicle may be an exosome. RNA includes, without limitation, mRNAs, rRNA, small RNAs, snRNAs, snoRNAs, microRNAs (miRNAs), small interfering RNAs (siRNAs), and noncoding RNAs. The RNA is preferably human RNA.

The term "construct" refers to one or more cell populations deposited on or in a surface of a scaffold or matrix made up of one or more synthetic or naturally-occurring biocompatible materials. The one or more cell populations may be coated with, deposited on, embedded in, attached to, seeded, or entrapped in a biomaterial made up of one or more synthetic or naturally-occurring biocompatible biomaterials, polymers, proteins, or peptides. The one or more cell populations may be combined with a biomaterial or scaffold or matrix in vitro or in vivo. In general, the one or more biocompatible materials used to form the scaffold/biomaterial is selected to direct, facilitate, or permit the formation of multicellular, three-dimensional, organization of at least one of the cell populations deposited thereon. The one or more biomaterials used to generate the construct may also be selected to direct, facilitate, or permit dispersion and/or integration of the construct or cellular components of the construct with the endogenous host tissue, or to direct, facilitate, or permit the survival, engraftment, tolerance, or functional performance of the construct or cellular components of the construct.

The term "marker" or "biomarker" refers generally to a DNA, RNA, protein, carbohydrate, or glycolipid-based molecular marker, the expression or presence of which in a cultured cell population can be detected by standard methods (or methods disclosed herein) and is consistent with one or more cells in the cultured cell population being a particular type of cell. The marker may be a polypeptide expressed by the cell or an identifiable physical location on a chromosome, such as a gene, a restriction endonuclease recognition site or a nucleic acid encoding a polypeptide (e.g., an mRNA) expressed by the native cell. The marker may be an expressed region of a gene referred to as a "gene expression marker", or some segment of DNA with no known coding function. The biomarkers may be cell-derived, e.g., secreted, products.

The terms "differentially expressed gene," "differential gene expression" and their synonyms, which are used interchangeably, refer to a gene whose expression is activated to a higher or lower level in a first cell or cell population, relative to its expression in a second cell or cell population. The terms also include genes whose expression is activated to a higher or lower level at different stages over time during passage of the first or second cell in culture. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes or their gene products, or a comparison of the ratios of the expression between two or more genes or their gene products, or even a comparison of two differently processed products of the same gene, which differ between the first cell and the second cell. Differential expression includes both quantitative, as well as qualitative, differences in the temporal or cellular expression pattern in a gene or its expression products among, for example, the first cell and the second cell. For the purpose of this invention, "differential gene expression" is considered to be present when there is a difference between the expression of a given gene in the first cell and the second cell. The differential expression of a marker may be in cells from a patient before administration of a cell population, admixture, or construct (the first cell) relative to expression in cells from the patient after administration (the second cell).

The terms "inhibit", "down-regulate", "under-express" and "reduce" are used interchangeably and mean that the expression of a gene, or level of RNA molecules or equivalent RNA molecules encoding one or more proteins or protein subunits, or activity of one or more proteins or protein subunits, is reduced relative to one or more controls, such as, for example, one or more positive and/or negative controls. The under-expression may be in cells from a patient before administration of a cell population, admixture, or construct relative to cells from the patient after administration.

The term "up-regulate" or "over-express" is used to mean that the expression of a gene; or level of RNA molecules or equivalent RNA molecules encoding one or more proteins or protein subunits, or activity of one or more proteins or protein subunits, is elevated relative to one or more controls, such as, for example, one or more positive and/or negative controls. The over-expression may be in cells from a patient after administration of a cell population, admixture, or construct relative to cells from the patient before administration.

The term "subject" shall mean any single human subject, including a patient, eligible for treatment, who is experiencing or has experienced one or more signs, symptoms, or other indicators of an organ-related disease, such as kidney disease, anemia, or EPO deficiency. Such subjects include without limitation subjects who are newly diagnosed or previously diagnosed and are now experiencing a recurrence or relapse, or are at risk for a kidney disease, anemia, or EPO deficiency, no matter the cause. The subject may have been previously treated for a kidney disease, anemia, or EPO deficiency, or not so treated.

The term "patient" refers to any single animal, more preferably a mammal (including such non-human animals as, for example, dogs, cats, horses, rabbits, zoo animals, cows, pigs, sheep, and non-human primates) for which treatment is desired. Most preferably, the patient herein is a human.

The term "sample" or "patient sample" or "biological sample" shall generally mean any biological sample obtained from a subject or patient, body fluid, body tissue, cell line, tissue culture, or other source. The term includes tissue biopsies such as, for example, kidney biopsies. The term includes cultured cells such as, for example, cultured mammalian kidney cells. Methods for obtaining tissue biopsies and cultured cells from mammals are well known in the art. If the term "sample" is used alone, it shall still mean that the "sample" is a "biological sample" or "patient sample", i.e., the terms are used interchangeably.

The term "test sample" refers to a sample from a subject that has been treated by a method of the present invention. The test sample may originate from various sources in the mammalian subject including, without limitation, blood, semen, serum, urine, bone marrow, mucosa, tissue, etc.

The term "control" or "control sample" refers a negative or positive control in which a negative or positive result is expected to help correlate a result in the test sample. Controls that are suitable for the present invention include, without limitation, a sample known to exhibit indicators characteristic of normal erythroid homeostasis, a sample known to exhibit indicators characteristic of anemia, a sample obtained from a subject known not to be anemic, and a sample obtained from a subject known to be anemic. Additional controls suitable for use in the methods of the present invention include, without limitation, samples derived from subjects that have been treated with pharmacological agents known to modulate erythropoiesis (e.g., recombinant EPO or EPO analogs). In addition, the control may be a sample obtained from a subject prior to being treated by a method of the present invention. An additional suitable control may be a test sample obtained from a subject known to have any type or stage of kidney disease, and a sample from a subject known not to have any type or stage of kidney disease. A control may be a normal healthy matched control. Those of skill in the art will appreciate other controls suitable for use in the present invention.

"Regeneration prognosis", "regenerative prognosis", or "prognostic for regeneration" generally refers to a forecast or prediction of the probable regenerative course or outcome of the administration or implantation of a cell population, admixture or construct described herein. For a regeneration prognosis, the forecast or prediction may be informed by one or more of the following: improvement of a functional organ (e.g., the kidney) after implantation or administration, development of a functional kidney after implantation or administration, development of improved kidney function or capacity after implantation or administration, and expression of certain markers by the native kidney following implantation or administration.

"Regenerated organ" refers to a native organ after implantation or administration of a cell population, admixture, or construct as described herein. The regenerated organ is characterized by various indicators including, without limitation, development of function or capacity in the native organ, improvement of function or capacity in the native organ, and the expression of certain markers in the native organ. Those of ordinary skill in the art will appreciate that other indicators may be suitable for characterizing a regenerated organ.

"Regenerated kidney" refers to a native kidney after implantation or administration of a cell population, admixture, or construct as described herein. The regenerated kidney is characterized by various indicators including, without limitation, development of function or capacity in the native kidney, improvement of function or capacity in the native kidney, and the expression of certain markers in the native kidney. Those of ordinary skill in the art will appreciate that other indicators may be suitable for characterizing a regenerated kidney.

The term "cellular aggregate" or "spheroid" refers to an aggregate or assembly of cells cultured to allow 3D growth as opposed to growth as a monolayer. It is noted that the term "spheroid" does not imply that the aggregate is a geometric sphere. The aggregate may be highly organized with a well defined morphology or it may be an unorganized mass; it may include a single cell type or more than one cell type. The cells may be primary isolates, or a permanent cell line, or a combination of the two. Included in this definition are organoids and organotypic cultures.

The term "ambient temperature" refers to the temperature at which the formulations of the present invention will be administered to a subject. Generally, the ambient temperature is the temperature of a temperature-controlled environment. Ambient temperature ranges from about 18° C. to about 30° C. In one embodiment, ambient temperature is about 18° C., about 19° C., about 20° C., about 21° C., about 22° C., about 23° C., about 24° C., about 25° C., about 26° C., about 27° C., about 28° C., about 29° C., or about 30° C.

2. Cell Populations

The formulations of the present invention may contain isolated, heterogeneous populations of kidney cells, and admixtures thereof, enriched for specific bioactive components or cell types and/or depleted of specific inactive or undesired components or cell types for use in the treatment of kidney disease, i.e., providing stabilization and/or improvement and/or regeneration of kidney function, were previously described in Presnell et al. U.S. 2011-0117162 and Hagan et al. PCT/US2011/036347, the entire contents of which are incorporated herein by reference. The formulations may contain isolated renal cell fractions that lack cellular components as compared to a healthy individual yet retain therapeutic properties, i.e., provide stabilization and/or improvement and/or regeneration of kidney function. The cell populations, cell fractions, and/or admixtures of cells described herein may be derived from healthy individuals, individuals with a kidney disease, or subjects as described herein.

The present invention provides formulations described herein are suitable for use with various bioactive cell populations including, without limitation, isolated cell population(s), cell fraction(s), admixture(s), enriched cell population(s), cellular aggregate(s), and any combination thereof. In one embodiment, the bioactive cell populations are bioactive renal cells.

Bioactive Cell Populations

The present invention contemplates therapeutic formulations suitable for bioactive cell populations that are to be administered to target organs or tissue in a subject in need. A bioactive cell population generally refers to a cell population potentially having therapeutic properties upon administration to a subject. For example, upon administration to a subject in need, a bioactive renal cell population can provide stabilization and/or improvement and/or regeneration of kidney function in the subject. The therapeutic properties may include a regenerative effect.

Bioactive cell populations include, without limitation, stem cells (e.g., pluripotent, multipotent, oligopotent, or unipotent) such as embryonic stem cells, amniotic stem cells, adult stem cells (e.g., hematopoietic, mammary, intestinal, mesenchymal, placental, lung, bone marrow, blood, umbilical cord, endothelial, dental pulp, adipose, neural, olfactory, neural crest, testicular), induced pluripotent stem cells; genetically modified cells; as well as cell populations or tissue explants derived from any source of the body. The formulations of the present invention may also be used with renal adipose-derived cell populations as described in Basu et al. PCT/US11/39859 filed on Jun. 9, 2011; and with the adipose-derived or peripheral blood-derived smooth muscle cells described in Ludlow et al. U.S. 2010-0131075 and Ludlow et al. PCT/US11/35058 filed on May 3, 2011; or bladder-derived urothelial or smooth muscle cells as described in Atala U.S. Pat. No. 6,576,019, each of which is incorporate herein by reference in its entirety. The bioactive cell populations may be isolated, enriched, purified, homogeneous, or heterogeneous in nature. Those of ordinary skill in the art will appreciate other bioactive cell populations that are suitable for use in the formulations of the present invention.

In one embodiment, the source of cells is the same as the intended target organ or tissue. For example, renal cells may be sourced from the kidney to be used in a formulation to be administered to the kidney. In another embodiment, the source of cells is not the same as the intended target organ or tissue. For example, erythropoietin-expressing cells may be sourced from renal adipose to be used in a formulation to be administered to the kidney.

In one aspect, the present invention provides formulations containing certain subfractions of a heterogeneous population of renal cells, enriched for bioactive components and depleted of inactive or undesired components provide superior therapeutic and regenerative outcomes than the starting population. For example, bioactive renal cells described herein, e.g., B2, B4, and B3, which are depleted of inactive or undesired components, e.g., B1 and B5, alone or admixed, can be part of a formulation to be used for the stabilization and/or improvement and/or regeneration of kidney function.

In another aspect, the formulations contain a specific subfraction, B4, depleted of or deficient in one or more cell types, e.g., vascular, endocrine, or endothelial, i.e., B4', that retain therapeutic properties, e.g., stabilization and/or improvement and/or regeneration of kidney function, alone or when admixed with other bioactive subfractions, e.g., B2 and/or B3. In a preferred embodiment, the bioactive cell population is B2. In certain embodiments, the B2 cell population is admixed with B4 or B4'. In other embodiments, the B2 cell population is admixed with B3. In other embodiments, the B2 cell population is admixed with both B3 and B4, or specific cellular components of B3 and/or B4.

The B2 cell population is characterized by expression of a tubular cell marker selected from the group consisting of one or more of the following: megalin, cubilin, hyaluronic acid synthase 2 (HAS2), Vitamin D3 25-Hydroxylase (CYP2D25), N-cadherin (Ncad), E-cadherin (Ecad), Aquaporin-1 (Aqp1), Aquaporin-2 (Aqp2), RAB17, member RAS oncogene family (Rab17), GATA binding protein 3 (Gata3), FXYD domain-containing ion transport regulator 4 (Fxyd4), solute carrier family 9 (sodium/hydrogen exchanger), member 4 (Slc9a-4), aldehyde dehydrogenase 3 family, member B1 (Aldh3b1), aldehyde dehydrogenase 1 family, member A3 (Aldh1a3), and Calpain-8 (Capn8), and collecting duct marker Aquaporin-4 (Aqp4). B2 is larger and more granulated than B3 and/or B4 and thus having a buoyant density between about 1.045 g/ml and about 1.063 g/ml (rodent), between about 1.045 g/ml and 1.052 g/ml (human), and between about 1.045 g/ml and about 1.058 g/ml (canine).

The B3 cell population is characterized by the expression of vascular, glomerular and proximal tubular markers with some EPO-producing cells, being of an intermediate size and granularity in comparison to B2 and B4, and thus having a buoyant density between about 1.063 g/ml and about 1.073 g/ml (rodent), between about 1.052 g/ml and about 1.063 g/ml (human), and between about 1.058 g/ml and about 1.063 g/ml (canine). B3 is characterized by expression of markers selected from the group consisting of one or more of the following: aquaporin 7 (Aqp7), FXYD domain-containing ion transport regulator 2 (Fxyd2), solute carrier family 17 (sodium phosphate), member 3 (Slc17a3), solute carrier family 3, member 1 (Slc3a1), claudin 2 (Cldn2), napsin A aspartic peptidase (Napsa), solute carrier family 2 (facilitated glucose transporter), member 2 (Slc2a2), alanyl (membrane) aminopeptidase (Anpep), transmembrane protein 27 (Tmem27), acyl-CoA synthetase medium-chain family member 2 (Acsm2), glutathione peroxidase 3 (Gpx3), fructose-1,6-biphosphatase 1 (Fbp1), and alanine-glyoxylate aminotransferase 2 (Agxt2). B3 is also characterized by the vascular expression marker Platelet endothelial cell adhesion molecule (Pecam) and the glomerular expression marker podocin (Podn).

The B4 cell population is characterized by the expression of a vascular marker set containing one or more of the following: PECAM, VEGF, KDR, HIF1a, CD31, CD146; a glomerular marker set containing one or more of the following: Podocin (Podn), and Nephrin (Neph); and an oxygen-tunable EPO enriched population compared to unfractionated (UNFX), B2 and B3. B4 is also characterized by the expression of one or more of the following markers: chemokine (C—X—C motif) receptor 4 (Cxcr4), endothelin receptor type B (Ednrb), collagen, type V, alpha 2 (Col5a2), Cadherin 5 (Cdh5), plasminogen activator, tissue (Plat), angiopoietin 2 (Angpt2), kinase insert domain protein receptor (Kdr), secreted protein, acidic, cysteine-rich (osteonectin) (Sparc), serglycin (Srgn), TIMP metallopeptidase inhibitor 3 (Timp3), Wilms tumor 1 (Wt1), wingless-type MMTV integration site family, member 4 (Wnt4), regulator of G-protein signaling 4 (Rgs4), Platelet endothelial cell adhesion molecule (Pecam), and Erythropoietin (Epo). B4 is also characterized by smaller, less granulated cells compared to either B2 or B3, with a buoyant density between about 1.073 g/ml and about 1.091 g/ml (rodent), between about 1.063 g/ml and about 1.091 g/mL (human and canine).

The B4' cell population is defined as having a buoyant density of between 1.063 g/mL and 1.091 g/mL and expressing one or more of the following markers: PECAM, vEGF, KDR, HIF1a, podocin, nephrin, EPO, CK7, CK8/18/19. In one embodiment, the B4' cell population is characterized by the expression of a vascular marker set containing one or more of the following: PECAM, vEGF, KDR, HIF1a, CD31, CD146. In another embodiment, the B4' cell population is characterized by the expression of an endocrine marker EPO. In one embodiment, the B4' cell population is characterized by the expression of a glomerular marker set containing one or more of the following: Podocin (Podn), and Nephrin (Neph). In certain embodiments, the B4' cell population is characterized by the expression of a vascular marker set containing one or more of the following: PECAM, vEGF, KDR, HIF1a and by the expression of an endocrine marker EPO. In another embodiment, B4' is also characterized by smaller, less granulated cells compared to either B2 or B3, with a buoyant density between about 1.073 g/ml and about 1.091 g/ml (rodent), between about 1.063 g/ml and about 1.091 g/mL (human and canine).

In one aspect, the present invention provides formulations containing an isolated, enriched B4' population of human renal cells comprising at least one of erythropoietin (EPO)-producing cells, vascular cells, and glomerular cells having a density between 1.063 g/mL and 1.091 g/mL. In one embodiment, the B4' cell population is characterized by expression of a vascular marker. In certain embodiments, the B4' cell population is not characterized by expression of a glomerular marker. In some embodiments, the B4' cell population is capable of oxygen-tunable erythropoietin (EPO) expression.

In one embodiment, formulation contains the B4' cell population but does not include a B2 cell population comprising tubular cells having a density between 1.045 g/mL and 1.052 g/mL. In another embodiment, the B4' cell population formulation does not include a B1 cell population comprising large granular cells of the collecting duct and tubular system having a density of <1.045 g/ml. In yet another embodiment, the B4' cell population formulation does not include a B5 cell population comprising debris and small cells of low granularity and viability with a density >1.091 g/ml.

In one embodiment, the B4' cell population-containing formulation does not include a B2 cell population comprising tubular cells having a density between 1.045 g/mL and 1.052 g/mL; a B1 cell population comprising large granular cells of the collecting duct and tubular system having a density of <1.045 g/ml; and a B5 cell population comprising debris and small cells of low granularity and viability with a density >1.091 g/ml. In some embodiments, the B4' cell population may be derived from a subject having kidney disease.

In one aspect, the present invention provides formulations containing admixtures of human renal cells comprising a first cell population, B2, comprising an isolated, enriched population of tubular cells having a density between 1.045 g/mL and 1.052 g/mL, and a second cell population, B4', comprising erythropoietin (EPO)-producing cells and vascular cells but depleted of glomerular cells having a density between about 1.063 g/mL and 1.091 g/mL, wherein the admixture does not include a B1 cell population comprising large granular cells of the collecting duct and tubular system having a density of <1.045 g/ml, or a B5 cell population comprising debris and small cells of low granularity and viability with a density >1.091 g/ml. In certain embodiment, the B4' cell population is characterized by expression of a vascular marker. In one embodiment, the B4' cell population is not characterized by expression of a glomerular marker. In certain embodiments, B2 further comprises collecting duct epithelial cells. In one embodiment, the formulation contains an admixture of cells that is capable of receptor-mediated albumin uptake. In another embodiment, the admixture of cells is capable of oxygen-tunable erythropoietin (EPO) expression. In one embodiment, the admixture contains HAS-2-expressing cells capable of producing and/or stimulating the production of high-molecular weight species of hyaluronic acid (HA) both in vitro and in vivo. In all embodiments, the first and second cell populations may be derived from kidney tissue or cultured kidney cells (Basu et al. Lipids in Health and Disease, 2011, 10:171).

In one embodiment, the formulation contains an admixture that is capable of providing a regenerative stimulus upon in vivo delivery. In other embodiments, the admixture is capable of reducing the decline of, stabilizing, or improving glomerular filtration, tubular resorption, urine production, and/or endocrine function upon in vivo delivery. In one embodiment, the B4' cell population is derived from a subject having kidney disease.

In one aspect, the present invention provides formulations containing an isolated, enriched B4' population of human renal cells comprising at least one of erythropoietin (EPO)-producing cells, vascular cells, and glomerular cells having a density between 1.063 g/mL and 1.091 g/mL. In one embodiment, the B4' cell population is characterized by expression of a vascular marker. In certain embodiments, the B4' cell population is not characterized by expression of a glomerular marker. The glomerular marker that is not expressed may be podocin (see Example 10). In some embodiments, the B4' cell population is capable of oxygen-tunable erythropoietin (EPO) expression.

In one embodiment, the B4' cell population-containing formulation does not include a B2 cell population comprising tubular cells having a density between 1.045 g/mL and 1.052 g/mL. In another embodiment, the B4' cell population formulation does not include a B1 cell population comprising large granular cells of the collecting duct and tubular system having a density of <1.045 g/ml. In yet another embodiment, the B4' cell population formulation does not include a B5 cell population comprising debris and small cells of low granularity and viability with a density >1.091 g/ml.

In one embodiment, the B4' cell population-containing formulation does not include a B2 cell population comprising tubular cells having a density between 1.045 g/mL and 1.052 g/mL; a B1 cell population comprising large granular cells of the collecting duct and tubular system having a density of <1.045 g/ml; and a B5 cell population comprising debris and small cells of low granularity and viability with a density >1.091 g/ml. In some embodiments, the B4' cell population may be derived from a subject having kidney disease.

In one aspect, the present invention provides formulations containing an admixture of human renal cells comprising a first cell population, B2, comprising an isolated, enriched population of tubular cells having a density between 1.045 g/mL and 1.052 g/mL, and a second cell population, B4', comprising erythropoietin (EPO)-producing cells and vascular cells but depleted of glomerular cells having a density between about 1.063 g/mL and 1.091 g/mL, wherein the admixture does not include a B1 cell population comprising large granular cells of the collecting duct and tubular system having a density of <1.045 g/ml, or a B5 cell population comprising debris and small cells of low granularity and viability with a density >1.091 g/ml. In certain embodiment, the B4' cell population is characterized by expression of a vascular marker. In one embodiment, the B4' cell population is not characterized by expression of a glomerular marker. In certain embodiments, B2 further comprises collecting duct epithelial cells. In one embodiment, the admixture of cells is capable of receptor-mediated albumin uptake. In another embodiment, the admixture of cells is capable of oxygen-tunable erythropoietin (EPO) expression. In one embodiment, the admixture contains HAS-2-expressing cells capable of producing and/or stimulating the production of high-molecular weight species of hyaluronic acid (HA) both in vitro and in vivo. In all embodiments, the first and second cell populations may be derived from kidney tissue or cultured kidney cells.

In another aspect, the present invention provides formulations containing a heterogeneous renal cell population comprising a combination of cell fractions or enriched cell populations (e.g., B1, B2, B3, B4 (or B4'), and B5). In one embodiment, the combination has a buoyant density between about 1.045 g/ml and about 1.091 g/ml. In one other embodiment, the combination has a buoyant density between less than about 1.045 g/ml and about 1.099 g/ml or about 1.100 g/ml. In another embodiment, the combination has a buoyant density as determined by separation on a density gradient, e.g., by centrifugation. In yet another embodiment, the combination of cell fractions contains B2, B3, and B4 (or B4') depleted of B1 and/or B5. In some embodiments, the combination of cell fractions contains B2, B3, B4 (or B4'), and B5 but is depleted of B1. Once depleted of B1 and/or B5, the combination may be subsequently cultured in vitro prior to the preparation of a formulation comprising the combination of B2, B3, and B4 (or B4') cell fractions.

The inventors of the present invention have surprisingly discovered that in vitro culturing, of a B1-depleted combination of B2, B3, B4, and B5 results in depletion of B5. In one embodiment, B5 is depleted after at least one, two, three, four, or five passages. In one other embodiment, the B2, B3, B4, and B5 cell fraction combination that is passaged under the conditions described herein provides a passaged cell population having B5 at a percentage that is less than about 5%, less than about 4%, less than about 3%, less than about 2%, less than about 1%, or less than about 0.5% of the passaged cell population.

In another embodiment, B4' is part of the combination of cell fractions. In one other embodiment, the in vitro culturing depletion of B5 is under hypoxic conditions.

In one embodiment, the formulation contains an admixture that is capable of providing a regenerative stimulus upon in vivo delivery. In other embodiments, the admixture is capable of reducing the decline of, stabilizing, or improving glomerular filtration, tubular resorption, urine production, and/or endocrine function upon in vivo delivery. In one embodiment, the B4' cell population is derived from a subject having kidney disease.

In a preferred embodiment, the formulation contains an admixture that comprises B2 in combination with B3 and/or B4. In another preferred embodiment, the admixture comprises B2 in combination with B3 and/or B4'. In other preferred embodiments, the admixture consists of or consists essentially of (i) B2 in combination with B3 and/or B4; or (ii) B2 in combination with B3 and/or B4'.

The admixtures that contain a B4' cell population may contain B2 and/or B3 cell populations that are also obtained from a non-healthy subject. The non-healthy subject may be the same subject from which the B4' fraction was obtained. In contrast to the B4' cell population, the B2 and B3 cell populations obtained from non-healthy subjects are typically not deficient in one or more specific cell types as compared to a starting kidney cell population derived from a healthy individual.

As described in Presnell et al. WO/2010/056328, it has been found that the B2 and B4 cell preparations are capable of expressing higher molecular weight species of hyaluronic acid (HA) both in vitro and in vivo, through the actions of hyaluronic acid synthase-2 (HAS-2)—a marker that is enriched more specifically in the B2 cell population. Treatment with B2 in a 5/6 Nx model was shown to reduce fibrosis, concomitant with strong expression HAS-2 expression in vivo and the expected production of high-molecular-weight HA within the treated tissue. Notably, the 5/6 Nx model left untreated resulted in fibrosis with limited detection of HAS-2 and little production of high-molecular-weight HA. Without wishing to be bound by theory, it is hypothesized that this anti-inflammatory high-molecular weight species of HA produced predominantly by B2 (and to some degree by B4) acts synergistically with the cell preparations in the reduction of renal fibrosis and in the aid of renal regeneration. Accordingly, the instant invention includes formulations containing the bioactive renal cells described herein along with a biomaterial comprising hyaluronic acid. Also contemplated by the instant invention is the provision of a biomaterial component of the regenerative stimulus via direct production or stimulation of production by the implanted cells.

In one aspect, the present invention provides formulations that contain isolated, heterogeneous populations of EPO-producing kidney cells for use in the treatment of kidney disease, anemia and/or EPO deficiency in a subject in need. In one embodiment, the cell populations are derived from a kidney biopsy. In another embodiment, the cell populations are derived from whole kidney tissue. In one other embodiment, the cell populations are derived from in vitro cultures of mammalian kidney cells, established from kidney biopsies or whole kidney tissue. In all embodiments, these populations are unfractionated cell populations, also referred to herein as non-enriched cell populations.

In another aspect, the present invention provides formulations that contain isolated populations of erythropoietin (EPO)-producing kidney cells that are further enriched such that the proportion of EPO-producing cells in the enriched subpopulation is greater relative to the proportion of EPO-producing cells in the starting or initial cell population. In one embodiment, the enriched EPO-producing cell fraction contains a greater proportion of interstitial fibroblasts and a lesser proportion of tubular cells relative to the interstitial fibroblasts and tubular cells contained in the unenriched initial population. In certain embodiments, the enriched EPO-producing cell fraction contains a greater proportion of glomerular cells and vascular cells and a lesser proportion of collecting duct cells relative to the glomerular cells, vascular cells and collecting duct cells contained in the unenriched initial population. In such embodiments, these populations are referred to herein as the "B4" cell population.

In another aspect, the present invention provides formulations containing an EPO-producing kidney cell population that is admixed with one or more additional kidney cell populations. In one embodiment, the EPO-producing cell population is a first cell population enriched for EPO-producing cells, e.g., B4. In another embodiment, the EPO-producing cell population is a first cell population that is not enriched for EPO-producing cells, e.g., B2. In another embodiment, the first cell population is admixed with a second kidney cell population. In some embodiments, the second cell population is enriched for tubular cells, which may be demonstrated by the presence of a tubular cell phenotype. In another embodiment, the tubular cell phenotype may be indicated by the presence of one tubular cell marker. In another embodiment, the tubular cell phenotype may be indicated by the presence of one or more tubular cell markers. The tubular cell markers include, without limitation, megalin, cubilin, hyaluronic acid synthase 2 (HAS2), Vitamin D3 25-Hydroxylase (CYP2D25), N-cadherin (Ncad), E-cadherin (Ecad), Aquaporin-1 (Aqp1), Aquaporin-2 (Aqp2), RAB17, member RAS oncogene family (Rab17), GATA binding protein 3 (Gata3), FXYD domain-containing ion transport regulator 4 (Fxyd4), solute carrier family 9 (sodium/hydrogen exchanger), member 4 (Slc9a-4), aldehyde dehydrogenase 3 family, member B1 (Aldh3b1), aldehyde dehydrogenase 1 family, member A3 (Aldh1a3), and Calpain-8 (Capn8). In another embodiment, the first cell population is admixed with at least one of several types of kidney cells including, without limitation, interstitium-derived cells, tubular cells, collecting duct-derived cells, glomerulus-derived cells, and/or cells derived from the blood or vasculature.

The formulations of the present invention may include EPO-producing kidney cell populations containing B4 or B4' in the form of an admixture with B2 and/or B3, or in the form of an enriched cell population, e.g., B2+B3+B4/B4'.

In one aspect, the formulation contains EPO-producing kidney cell populations that are characterized by EPO expression and bioresponsiveness to oxygen, such that a reduction in the oxygen tension of the culture system results in an induction in the expression of EPO. In one embodiment, the EPO-producing cell populations are enriched for EPO-producing cells. In one embodiment, the EPO expression is induced when the cell population is cultured under conditions where the cells are subjected to a reduction in available oxygen levels in the culture system as compared to a cell population cultured at normal atmospheric (~21%) levels of available oxygen. In one embodiment, EPO-producing cells cultured in lower oxygen conditions express greater levels of EPO relative to EPO-producing cells cultured at normal oxygen conditions. In general, the culturing of cells at reduced levels of available oxygen (also referred to as hypoxic culture conditions) means that the level of reduced oxygen is reduced relative to the culturing of cells at normal atmospheric levels' of available oxygen (also referred to as normal or normoxic culture conditions). In one embodiment, hypoxic cell culture conditions include culturing cells at about less than 1% oxygen, about less than 2% oxygen, about less than 3% oxygen, about less than 4% oxygen, or about less than 5% oxygen. In another embodiment, normal or normoxic culture conditions include culturing cells at about 10% oxygen, about 12% oxygen, about 13% oxygen, about 14% oxygen, about 15% oxygen, about 16% oxygen, about 17% oxygen, about 18% oxygen, about 19% oxygen, about 20% oxygen, or about 21% oxygen.

In one other embodiment, induction or increased expression of EPO is obtained and can be observed by culturing cells at about less than 5% available oxygen and comparing EPO expression levels to cells cultured at atmospheric (about 21%) oxygen. In another embodiment, the induction of EPO is obtained in a culture of cells capable of expressing EPO by a method that includes a first culture phase in which the culture of cells is cultivated at atmospheric oxygen (about 21%) for some period of time and a second culture phase in which the available oxygen levels are reduced and the same cells are cultured at about less than 5% available oxygen. In another embodiment, the EPO expression that is responsive to hypoxic conditions is regulated by HIF1α. Those of ordinary skill in the art will appreciate that other oxygen manipulation culture conditions known in the art may be used for the cells described herein.

In one aspect, the formulation contains enriched populations of EPO-producing mammalian cells characterized by bio-responsiveness (e.g., EPO expression) to perfusion conditions. In one embodiment, the perfusion conditions include transient, intermittent, or continuous fluid flow (perfusion). In one embodiment, the EPO expression is mechanically-induced when the media in which the cells are cultured is intermittently or continuously circulated or agitated in such a manner that dynamic forces are transferred to the cells via the flow. In one embodiment, the cells subjected to the transient, intermittent, or continuous fluid flow are cultured in such a manner that they are present as three-dimensional structures in or on a material that provides framework and/or space for such three-dimensional structures to form. In one embodiment, the cells are cultured on porous beads and subjected to intermittent or continuous fluid flow by means of a rocking platform, orbiting platform, or spinner flask. In another embodiment, the cells are cultured on three-dimensional scaffolding and placed into a device whereby the scaffold is stationary and fluid flows directionally through or across the scaffolding. Those of ordinary skill in the art will appreciate that other perfusion culture conditions known in the art may be used for the cells described herein.

Cellular Aggregates

In one other aspect, the formulations of the present invention contain cellular aggregates or spheroids. In one embodiment, the cellular aggregate comprises a bioactive cell population described herein. In another embodiment, the cellular aggregate comprises bioactive renal cells such as, for example, renal cell admixtures, enriched renal cell populations, and combinations of renal cell fractions.

In certain embodiments, the bioactive renal cells of the invention may be cultured in 3D formats as described further herein. In some embodiments, the term "organoid" refers to an accumulation of cells, with a phenotype and/or function, consistent with a native kidney. In some embodiments, organoids comprise mixed populations of cells, of a variety of lineages, which are typically found in vivo in a given tissue. In some embodiments, the organoids of this invention are formed in vitro, via any means, whereby the cells of the invention form aggregates, which in turn may form spheroids, organoids, or a combination thereof. Such aggregates, spheroids or organoids, in some embodiments, assume a structure consistent with a particular organ. In some embodiments, such aggregates, spheroids or organoids, express surface markers, which are typically expressed by cells of the particular organ. In some embodiments, such aggregates, spheroids or organoids, produce compounds or materials, which are typically expressed by cells of the particular organ. In certain embodiments, the cells of the invention may be cultured on natural substrates, e.g., gelatin. In other embodiments, the cells of the invention may be cultured on synthetic substrates, e.g., PGLA. An exemplary method for providing cellular aggregates is provided in Example 20.

Inactive Cell Populations

As described herein, the present invention is based, in part, on the surprising finding that certain subfractions of a heterogeneous population of renal cells, enriched for bioactive components and depleted of inactive or undesired components, provide superior therapeutic and regenerative outcomes than the starting population. In preferred embodiments, the formulations provided by the present invention contain cellular populations that are depleted of B1 and/or B5 cell populations. For instance, the following may be depleted of B1 and/or B5: admixtures of two or more of B2, B3, and B4 (or B4'); an enriched cell population of B2, B3, and B4 (or B4').

The B1 cell population comprises large, granular cells of the collecting duct and tubular system, with the cells of the population having a buoyant density less than about 1.045 g/m. The B5 cell population is comprised of debris and small cells of low granularity and viability and having a buoyant density greater than about 1.091 g/ml.

Methods of Isolating and Culturing Cell Populations

In one aspect, the formulations of the present invention contain cell populations that have been isolated and/or cultured from kidney tissue. Methods are provided herein for separating and isolating the renal cellular components, e.g., enriched cell populations that will be used in the formulations for therapeutic use, including the treatment of kidney disease, anemia, EPO deficiency, tubular transport deficiency, and glomerular filtration deficiency. In one embodiment, the cell populations are isolated from freshly digested, i.e., mechanically or enzymatically digested, kidney tissue or from heterogeneous in vitro cultures of mammalian kidney cells.

The formulations may contain heterogeneous mixtures of renal cells that have been cultured in hypoxic culture conditions prior to separation on a density gradient provides for enhanced distribution and composition of cells in both B4, including B4', and B2 and/or B3 fractions. The enrichment of oxygen-dependent cells in B4 from B2 was observed for renal cells isolated from both diseased and non-diseased kidneys. Without wishing to be bound by theory, this may be due to one or more of the following phenomena: 1) selective survival, death, or proliferation of specific cellular components during the hypoxic culture period; 2) alterations in cell granularity and/or size in response to the hypoxic culture, thereby effecting alterations in buoyant density and subsequent localization during density gradient separation; and 3)

alterations in cell gene/protein expression in response to the hypoxic culture period, thereby resulting in differential characteristics of the cells within any given fraction of the gradient. Thus, in one embodiment, the formulations contain cell populations enriched for tubular cells, e.g., B2, are hypoxia-resistant.

Exemplary techniques for separating and isolating the cell populations of the invention include separation on a density gradient based on the differential specific gravity of different cell types contained within the population of interest. The specific gravity of any given cell type can be influenced by the degree of granularity within the cells, the intracellular volume of water, and other factors. In one aspect, the present invention provides optimal gradient conditions for isolation of the cell preparations of the instant invention, e.g., B2 and B4, including B4', across multiple species including, but not limited to, human, canine, and rodent. In a preferred embodiment, a density gradient is used to obtain a novel enriched population of tubular cells fraction, i.e., B2 cell population, derived from a heterogeneous population of renal cells. In one embodiment, a density gradient is used to obtain a novel enriched population of EPO-producing cells fraction, i.e., B4 cell population, derived from a heterogeneous population of renal cells. In other embodiments, a density gradient is used to obtain enriched subpopulations of tubular cells, glomerular cells, and endothelial cells of the kidney. In one embodiment, both the EPO-producing and the tubular cells are separated from the red blood cells and cellular debris. In one embodiment, the EPO-producing, glomerular, and vascular cells are separated from other cell types and from red blood cells and cellular debris, while a subpopulation of tubular cells and collecting duct cells are concomitantly separated from other cell types and from red blood cells and cellular debris. In one other embodiment, the endocrine, glomerular, and/or vascular cells are separated from other cell types and from red blood cells and cellular debris, while a subpopulation of tubular cells and collecting duct cells are concomitantly separated from other cell types and from red blood cells and cellular debris.

In one aspect, the formulations of the present invention contain cell populations generated by using, in part, the OPTIPREP® (Axis-Shield) density gradient medium, comprising 60% nonionic iodinated compound iodixanol in water, based on certain key features described below. One of skill in the art, however, will recognize that any density gradient or other means, e.g., immunological separation using cell surface markers known in the art, comprising necessary features for isolating the cell populations of the instant invention may be used in accordance with the invention. It should also be recognized by one skilled in the art that the same cellular features that contribute to separation of cellular subpopulations via density gradients (size and granularity) can be exploited to separate cellular subpopulations via flow cytometry (forward scatter=a reflection of size via flow cytometry, and side scatter=a reflection of granularity). Importantly, the density gradient medium should have low toxicity towards the specific cells of interest. While the density gradient medium should have low toxicity toward the specific cells of interest, the instant invention contemplates the use of gradient mediums which play a role in the selection process of the cells of interest. Without wishing to be bound by theory, it appears that the cell populations of the instant invention recovered by the gradient comprising iodixanol are iodixanol-resistant, as there is an appreciable loss of cells between the loading and recovery steps, suggesting that exposure to iodixanol under the conditions of the gradient leads to elimination of certain cells. The cells appearing in the specific bands after the iodixanol gradient are resistant to any untoward effects of iodixanol and/or density gradient exposure. Accordingly, the use of additional contrast media which are mild to moderate nephrotoxins in the isolation and/or selection of the cell populations for the formulations described herein is also contemplated. In addition, the density gradient medium should also not bind to proteins in human plasma or adversely affect key functions of the cells of interest.

In another aspect, the present invention provides formulations containing cell populations that have been enriched and/or depleted of kidney cell types using fluorescent activated cell sorting (FACS). In one embodiment, kidney cell types may be enriched and/or depleted using BD FACSAria™ or equivalent.

In another aspect, the formulations contain cell populations that have been enriched and/or depleted of kidney cell types using magnetic cell sorting. In one embodiment, kidney cell types may be enriched and/or depleted using the Miltenyi autoMACS® system or equivalent.

In another aspect, the formulations may include renal cell populations that have been subject to three-dimensional culturing. In one aspect, the methods of culturing the cell populations are via continuous perfusion. In one embodiment, the cell populations cultured via three-dimensional culturing and continuous perfusion demonstrate greater cellularity and interconnectivity when compared to cell populations cultured statically. In another embodiment, the cell populations cultured via three dimensional culturing and continuous perfusion demonstrate greater expression of EPO, as well as enhanced expression of renal tubule-associate genes such as e-cadherin when compared to static cultures of such cell populations. In yet another embodiment, the cell populations cultured via continuous perfusion demonstrate greater levels of glucose and glutamine consumption when compared to cell populations cultured statically.

As described herein (including Example 7), low or hypoxic oxygen conditions may be used in the methods to prepare the cell populations for the formulations of the present invention. However, the methods of preparing cell populations may be used without the step of low oxygen conditioning. In one embodiment, normoxic conditions may be used.

In one other aspect, the present invention provides protocols for preparing cellular aggregates or spheroids (see, e.g., Example 20).

Those of ordinary skill in the art will appreciate that other methods of isolation and culturing known in the art may be used for the cells described herein.

3. Biomaterials

A variety of biomaterials may be combined with an active agent to provide the therapeutic formulations of the present invention. The biomaterials may be in any suitable shape (e.g., beads) or form (e.g., liquid, gel, etc.). As described in Bertram et al. U.S. Published Application 20070276507 (incorporated herein by reference in its entirety), polymeric matrices or scaffolds may be shaped into any number of desirable configurations to satisfy any number of overall system, geometry or space restrictions. In one embodiment, the matrices or scaffolds of the present invention may be three-dimensional and shaped to conform to the dimensions and shapes of an organ or tissue structure. For example, in the use of the polymeric scaffold for treating kidney disease, anemia, EPO deficiency, tubular transport deficiency, or glomerular filtration deficiency, a three-dimensional (3-D) matrix may be used. A variety of differently shaped 3-D scaffolds may be used. Naturally, the polymeric matrix may be shaped in different sizes and shapes to conform to differently sized patients. The polymeric matrix may also be shaped in other ways to accommodate the special needs of the patient. In another embodiment, the polymeric matrix or scaffold may be a biocompatible, porous polymeric scaffold. The scaffolds may be formed from a variety of synthetic or naturally-occurring materials including, but not limited to, open-cell polylactic acid (OPLA®), cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, collagens, gelatin, alginate, laminins, fibronectin, silk, elastin, alginate, hyaluronic acid, agarose, or copolymers or physical blends thereof. Scaffolding configurations may range from liquid suspensions to soft porous scaffolds to rigid, shape-holding porous scaffolds. In one embodiment, the configuration is the liquid form of a solution that is capable of becoming a hydrogel.

Hydrogels may be formed from a variety of polymeric materials and are useful in a variety of biomedical applications. Hydrogels can be described physically as three-dimensional networks of hydrophilic polymers. Depending on the type of hydrogel, they contain varying percentages of water, but altogether do not dissolve in water. Despite their high water content, hydrogels are capable of additionally binding great volumes of liquid due to the presence of hydrophilic residues. Hydrogels swell extensively without changing their gelatinous structure. The basic physical features of hydrogel can be specifically modified, according to the properties of the polymers used and the additional special equipments of the products.

Preferably, the hydrogel is made of a polymer, a biologically derived material, a synthetically derived material or combinations thereof, that is biologically inert and physiologically compatible with mammalian tissues. The hydrogel material preferably does not induce an inflammatory response. Examples of other materials which can be used to form a hydrogel include (a) modified alginates, (b) polysaccharides (e.g. gellan gum and carrageenans) which gel by exposure to monovalent cations, (c) polysaccharides (e.g., hyaluronic acid) that are very viscous liquids or are thixotropic and form a gel over time by the slow evolution of structure, (d) gelatin or collagen, and (e) polymeric hydrogel precursors (e.g., polyethylene oxide-polypropylene glycol block copolymers and proteins). U.S. Pat. No. 6,224,893 B1 provides a detailed description of the various polymers, and the chemical properties of such polymers, that are suitable for making hydrogels in accordance with the present invention.

Scaffolding or biomaterial characteristics may enable cells to attach and interact with the scaffolding or biomaterial material, and/or may provide porous spaces into which cells can be entrapped. In one embodiment, the porous scaffolds or biomaterials of the present invention allow for the addition or deposition of one or more populations or admixtures of cells on a biomaterial configured as a porous scaffold (e.g., by attachment of the cells) and/or within the pores of the scaffold (e.g., by entrapment of the cells). In another embodiment, the scaffolds or biomaterials allow or promote for cell:cell and/or cell:biomaterial interactions within the scaffold to form constructs as described herein.

In one embodiment, the biomaterial used in accordance with the present invention is comprised of hyaluronic acid (HA) in hydrogel form, containing HA molecules ranging in size from 5.1 kDA to >$2\times10^6$ kDa. In another embodiment, the biomaterial used in accordance with the present invention is comprised of hyaluronic acid in porous foam form, also containing HA molecules ranging in size from 5.1 kDA to >$2\times10^6$ kDa. In yet another embodiment, the biomaterial used in accordance with the present invention is comprised of a poly-lactic acid (PLA)-based foam, having an open-cell structure and pore size of about 50 microns to about 300 microns. In yet another embodiment, the specific cell populations, preferentially B2 but also B4, provide directly and/or stimulate synthesis of high molecular weight Hyaluronic Acid through Hyaluronic Acid Synthase-2 (HAS-2), especially after intra-renal implantation.

The biomaterials described herein may also be designed or adapted to respond to certain external conditions, e.g., in vitro or in vivo. In one embodiment, the biomaterials are temperature-sensitive (e.g., either in vitro or in vivo). In another embodiment, the biomaterials are adapted to respond to exposure to enzymatic degradation (e.g., either in vitro or in vivo). The biomaterials' response to external conditions can be fine tuned as described herein. Temperature sensitivity of the formulation described can be varied by adjusting the percentage of a biomaterial in the formulation. For example, the percentage of gelatin in a solution can be adjusted to modulate the temperature sensitivity of the gelatin in the final formulation (e.g., liquid, gel, beads, etc.). Alternatively, biomaterials may be chemically cross-linked to provide greater resistance to enzymatic degradation. For instance, a carbodiimide crosslinker may be used to chemically crosslink gelatin beads thereby providing a reduced susceptibility to endogenous enzymes.

In one aspect, the response by the biomaterial to external conditions concerns the loss of structural integrity of the biomaterial. Although temperature-sensitivity and resistance to enzymatic degradation are provided above, other mechanisms exist by which the loss of material integrity may occur in different biomaterials. These mechanisms may include, but are not limited to thermodynamic (e.g., a phase transition such as melting, diffusion (e.g., diffusion of an ionic crosslinker from a biomaterial into the surrounding tissue)), chemical, enzymatic, pH (e.g., pH-sensitive liposomes), ultrasound, and photolabile (light penetration). The exact mechanism by which the biomaterial loses structural integrity will vary but typically the mechanism is triggered either at the time of implantation or post-implantation.

Those of ordinary skill in the art will appreciate that other types of synthetic or naturally-occurring materials known in the art may be used to form scaffolds as described herein.

In one aspect, the present invention provides constructs as described herein made from the above-referenced scaffolds or biomaterials.

4. Constructs

In one aspect, the invention provides formulations that contain implantable constructs having one or more of the cell populations described herein for the treatment of kidney disease, anemia, or EPO deficiency in a subject in need. In one embodiment, the construct is made up of a biocompatible material or biomaterial, scaffold or matrix composed of one or more synthetic or naturally-occurring biocompatible materials and one or more cell populations or admixtures of cells described herein deposited on or embedded in a surface of the scaffold by attachment and/or entrapment. In certain embodiments, the construct is made up of a biomaterial and one or more cell populations or admixtures of cells described herein coated with, deposited on, deposited in, attached to, entrapped in, embedded in, seeded, or combined with the biomaterial component(s). Any of the cell populations described herein, including enriched cell populations or admixtures thereof, may be used in combination with a matrix to form a construct.

In one aspect, the formulation contains constructs that are made up of biomaterials designed or adapted to respond to external conditions as described herein. As a result, the nature of the association of the cell population with the biomaterial in a construct will change depending upon the external conditions. For example, a cell population's association with a temperature-sensitive biomaterial varies with temperature. In one embodiment, the construct contains a cell population and biomaterial having a substantially solid state at about 8° C. or lower and a substantially liquid state at about ambient temperature or above, wherein the cell population is suspended in the biomaterial at about 8° C. or lower.

However, the cell population is substantially free to move throughout the volume of the biomaterial at about ambient temperature or above. Having the cell population suspended in the substantially solid phase at a lower temperature provides stability advantages for the cells, such as for anchorage-dependent cells, as compared to cells in a fluid. Moreover, having cells suspended in the substantially solid state provides one or more of the following benefits: i) prevents settling of the cells, ii) allows the cells to remain anchored to the biomaterial in a suspended state; iii) allows the cells to remain more uniformly dispersed throughout the volume of the biomaterial; iv) prevents the formation of cell aggregates; and v) provides better protection for the cells during storage and transportation of the formulation. A formulation that can retain such features leading up to the administration to a subject is advantageous at least because the overall health of the cells in the formulation will be better and a more uniform and consistent dosage of cells will be administered.

In another embodiment, the deposited cell population or cellular component of the construct is a first kidney cell population enriched for oxygen-tunable EPO-producing cells. In another embodiment, the first kidney cell population contains glomerular and vascular cells in addition to the oxygen-tunable EPO-producing cells. In one embodiment, the first kidney cell population is a B4' cell population. In one other embodiment, the deposited cell population or cellular component(s) of the construct includes both the first enriched renal cell population and a second renal cell population. In some embodiments, the second cell population is not enriched for oxygen-tunable EPO producing cells. In another embodiment, the second cell population is enriched for renal tubular cells. In another embodiment, the second cell population is enriched for renal tubular cells and contains collecting duct epithelial cells. In other embodiments, the renal tubular cells are characterized by the expression of one or more tubular cell markers that may include, without limitation, megalin, cubilin, hyaluronic acid synthase 2 (HAS2), Vitamin D3 25-Hydroxylase (CYP2D25), N-cadherin (Ncad), E-cadherin (Ecad), Aquaporin-1 (Aqp1), Aquaporin-2 (Aqp2), RAB17, member RAS oncogene family (Rab17), GATA binding protein 3 (Gata3), FXYD domain-containing ion transport regulator 4 (Fxyd4), solute carrier family 9 (sodium/hydrogen exchanger), member 4 (Slc9a-4), aldehyde dehydrogenase 3 family, member B1 (Aldh3b1), aldehyde dehydrogenase 1 family, member A3 (Aldh1a3), and Calpain-8 (Capn8).

In one embodiment, the cell populations deposited on or combined with biomaterials or scaffolds to form constructs of the present invention are derived from a variety of sources, such as autologous sources. Non-autologous sources are also suitable for use, including without limitation, allogeneic, or syngeneic (autogeneic or isogeneic) sources.

Those of ordinary skill in the art will appreciate there are several suitable methods for depositing or otherwise combining cell populations with biomaterials to form a construct.

In one aspect, the constructs of the present invention are suitable for use in the methods of use described herein. In one embodiment, the constructs are suitable for administration to a subject in need of treatment for a kidney disease of any etiology, anemia, or EPO deficiency of any etiology. In other embodiments, the constructs are suitable for administration to a subject in need of an improvement in or restoration of erythroid homeostasis. In another embodiment, the constructs are suitable for administration to a subject in need of improved kidney function.

In yet another aspect, the present invention provides a construct for implantation into a subject in need of improved kidney function comprising: a) a biomaterial comprising one or more biocompatible synthetic polymers or naturally-occurring proteins or peptides; and b) an admixture of mammalian renal cells derived from a subject having kidney disease comprising a first cell population, B2, comprising an isolated, enriched population of tubular cells having a density between 1.045 g/mL and 1.052 g/mL and a second cell population, B4', comprising erythropoietin (EPO)-producing cells and vascular cells but depleted of glomerular cells having a density between 1.063 g/mL and 1.091 g/mL, coated with, deposited on or in, entrapped in, suspended in, embedded in and/or otherwise combined with the biomaterial. In certain embodiments, the admixture does not include a B1 cell population comprising large granular cells of the collecting duct and tubular system having a density of <1.045 g/ml, or a B5 cell population comprising debris and small cells of low granularity and viability with a density >1.091 g/ml.

In one embodiment, the construct includes a B4' cell population which is characterized by expression of a vascular marker. In some embodiments, the B4' cell population is not characterized by expression of a glomerular marker. In certain embodiments, the admixture is capable of oxygen-tunable erythropoietin (EPO) expression. In all embodiments, the admixture may be derived from mammalian kidney tissue or cultured kidney cells.

In one embodiment, the construct includes a biomaterial configured as a three-dimensional (3-D) porous biomaterial suitable for entrapment and/or attachment of the admixture. In another embodiment, the construct includes a biomaterial configured as a liquid or semi-liquid gel suitable for embedding, attaching, suspending, or coating mammalian cells. In yet another embodiment, the construct includes a biomaterial configured comprised of a predominantly high-molecular weight species of hyaluronic acid (HA) in hydrogel form. In another embodiment, the construct includes a biomaterial comprised of a predominantly high-molecular weight species of hyaluronic acid in porous foam form. In yet another embodiment, the construct includes a biomaterial comprised of a poly-lactic acid-based foam having pores of between about 50 microns to about 300 microns. In still another embodiment, the construct includes one or more cell populations that may be derived from a kidney sample that is autologous to the subject in need of improved kidney function. In certain embodiments, the sample is a kidney biopsy. In some embodiments, the subject has a kidney disease. In yet other embodiments, the cell population is derived from a non-autologous kidney sample. In one embodiment, the construct provides erythroid homeostasis.

5. Secreted Products

In one other aspect, the present invention concerns formulations that contain active agents, such as cell populations, in combination with products secreted from an enriched renal cell population or admixture of enriched renal cell populations, as described herein. In one embodiment, the products include one or more of the following: paracrine factors, endocrine factors, juxtacrine factors, and vesicles. The vesicles may include one or more of the following: paracrine factors, endocrine factors, juxtacrine factors, microvesicles, exosomes, and RNA. The secreted products may also include products that are not within microvesicles including, without limitation, paracrine factors, endocrine factors, juxtacrine factors, and RNA. For example, extracellular miRNAs have been detected externally to vesicles (Wang et al., *Nuc Acids Res* 2010, 1-12 doi:10.1093/nar/gkq601, Jul. 7, 2010). The secreted products may also be referred to as cell-derived products, e.g., cell-derived vesicles.

In one other embodiment, the formulation contains secreted products that are part of a vesicle derived from renal cells. The vesicles may be capable of delivering the factors to other destinations. In one embodiment, the vesicles are secreted vesicles. Several types of secreted vesicles are contemplated including, without limitation, exosomes, microvesicles, ectosomes, membrane particles, exosome-like vesicles, and apoptotic vesicles (Thery et al. 2010. Nat. Rev. Immunol. 9:581-593). In one embodiment, the secreted vesicles are exosomes. In one other embodiment, the secreted vesicles are microvesicles. In one other embodiment, the secreted vesicles contain or comprise one or more cellular components. The components may be one or more of the following: membrane lipids, RNA, proteins, metabolities, cytosolic components, and any combination thereof. In a preferred embodiment, the secreted vesicles comprise, consist of, or consist essentially of microRNAs. Preferably, the miRNAs are human miRNAs. In one embodiment, one or more miRNAs are selected from the group consisting of miR-30b-5p, miR-449a, miR-146a, miR-130a, miR-23b, miR-21, miR-124, and miR-151. In one other embodiment, one or more miRNAs may be selected from the group consisting of let-7a-1; let-7a-2; let-7a-3; let-7b; let-7c; let-7d; let-7e; let-7f-1; let-7f-2; let-7g; let-7i; mir-1-1; mir-1-2; mir-7-1; mir-7-2; mir-7-3; mir-9-1; mir-9-2; mir-9-3; mir-10a; mir-10b; mir-15a; mir-15b; mir-16-1; mir-16-2; mir-17; mir-18a; mir-18b; mir-19a; mir-19b-1; mir-19b-2; mir-20a; mir-20b; mir-21; mir-22; mir-23a; mir-23b; mir-23c; mir-24-1; mir-24-2; mir-25; mir-26a-1; mir-26a-2; mir-26b; mir-27a; mir-27b; mir-28; mir-29a; mir-29b-1; mir-29b-2; mir-29c; mir-30a; mir-30b; mir-30c-1; mir-30c-2; mir-30d; mir-30e; mir-31; mir-32; mir-33a; mir-33b; mir-34a; mir-34b; mir-34c; mir-92a-1; mir-92a-2; mir-92b; mir-93; mir-95; mir-96; mir-98; mir-99a mir-99b; mir-100; mir-101-1; mir-101-2; mir-103-1; mir-103-1-as; mir-103-2; mir-103-2-as; mir-105-1; mir-105-2; mir-106a; mir-106b; mir-107; mir-122; mir-124-1; mir-124-2; mir-124-3; mir-125a; mir-125b-1; mir-125b-2; mir-126; mir-127; mir-128-1; mir-128-2; mir-129-1; mir-129-2; mir-130a; mir-130b; mir-132; mir-132; mir-133a-1; mir-133a-2; mir-133b; mir-134; mir-135a-1; mir-135a-2; mir-135b; mir-136 MI101351120; mir-137; mir-138-1; mir-138-2; mir-139; mir-140; mir-141; mir-142; mir-143; mir-144; mir-145; mir-146a; mir-146b; mir-147; mir-147b; mir-148a; mir-148b; mir-149; mir-150; mir-151; mir-152; mir-153-1; mir-153-2; mir-154; mir-155; mir-181a-1; mir-181a-2; mir-181b-1; mir-181b-2; mir-181c; mir-181d; mir-182; mir-183; mir-184; mir-185; mir-186; mir-187; mir-188; mir-190; mir-190b; mir-191; mir-192; mir-193a; mir-193b; mir-194-1; mir-194-2; mir-195; mir-196a-1; mir-196a-2; mir-196b; mir-197; mir-198; mir-199a-1; mir-199a-2; mir-199b; mir-200a; mir-200b; mir-200c; mir-202; mir-203; mir-204; mir-205; mir-206; mir-208a; mir-208b; mir-210; mir-211; mir-212; mir-214; mir-215; mir-216a; mir-216b; mir-217; mir-218-1; mir-218-2; mir-219-1; mir-219-2; mir-221; mir-222; mir-223; 224; mir-296; mir-297; mir-298; mir-299; mir-300; mir-301a; mir-301b; mir-302a; mir-302b; mir-302c; mir-302d; mir-302e; mir-302f; mir-320a; mir-320b-1; mir-320b-2; mir-320c-1; mir-320c-2; mir-320d-1; mir-320d-2; mir-320e; mir-323; mir-323b; mir-324; mir-325; mir-326; mir-328; mir-329-1; mir-329-2; mir-330; mir-331; mir-335; mir-337; mir-338; mir-339; mir-340; mir-342; mir-345; mir-346; mir-361; mir-362; mir-363; mir-365-1; mir-365-2; mir-367; mir-369; mir-370; mir-37; mir-372; mir-373; mir-374a; mir-374b; mir-374c; mir-375; mir-376a-1; mir-376a-2; mir-376b; mir-376c; mir-377; mir-378; mir-378b; mir-378c; mir-379; mir-380; mir-381; mir-382; mir-383; mir-384; mir-409; mir-410; mir-411; mir-412; mir-421; mir-422a; mir-423; mir-424; mir-425; mir-429; mir-431; mir-432; mir-433; mir-448; mir-449a; mir-449b; mir-449c; mir-450a-1; mir-450a-2; mir-450b; mir-451; mir-452; mir-454; mir-455; mir-466; mir-483; mir-484; mir-485; mir-486; mir-487a; mir-487b; mir-488; mir-489; mir-490; mir-491; mir-492; mir-493; mir-494; mir-495; mir-496; mir-497; mir-498; mir-499; mir-500a; mir-500b; mir-501; mir-502; mir-503; mir-504; mir-505; mir-506; mir-507; mir-508; mir-509-1; mir-509-2; mir-509-3; mir-510; mir-511-1; mir-511-2; mir-512-1; mir-512-2; mir-513a-1; mir-513a-2; mir-513b; mir-513c; mir-514-1; mir-514-2; mir-514-3; mir-514b; mir-515-1; mir-515-2; mir-516a-1; mir-516a-2; mir-516b-1; mir-516b-2; mir-517a; mir-517b; mir-517c; mir-518a-1; mir-518a-2; mir-518b; mir-518c; mir-518d; mir-518e; mir-518f; mir-519a-1; mir-519a-2; mir-519b; mir-519c; mir-519d; mir-519e; mir-520a; mir-520b; mir-520c; mir-520d; mir-520e; mir-520f; mir-520g; mir-520h; mir-521-1; mir-521-2; mir-522; mir-523; mir-524; mir-525; mir-526a-1; mir-526a-2; mir-526b; mir-527; mir-532; mir-539; mir-541; mir-542; mir-543; mir-544; mir-544b; mir-545; mir-548a-1; mir-548a-2; mir-548a-3; mir-548a-1; mir-548aa-2; mir-548b; mir-548c; mir-548d-1; mir-548d-2; mir-548e; mir-548f-1; mir-548f-2; mir-548f-3; mir-548f-4; mir-548f-5; mir-548g; mir-548h-1; mir-548h-2; mir-548h-3; mir-548h-4; mir-548i-1; mir-548i-2; mir-548i-3; mir-548i-4; mir-548j; mir-548k; mir-548l; mir-548m; mir-548n; mir-548o; mir-548p; mir-548s; mir-548t; mir-548u; mir-548v; mir-548w; mir-548x; mir-548y; mir-548z; mir-549; mir-550a-1; mir-550a-2; mir-550b-1; mir-550b-2; mir-551a; mir-551b; mir-552; mir-553; mir-554; mir-555; mir-556; mir-557; mir-558; mir-559; mir-561; mir-562; mir-563; mir-564; mir-566; mir-567; mir-568; mir-569; mir-570; mir-571; mir-572; mir-573; mir-574; mir-575; mir-576; mir-577; mir-578; mir-579; mir-580; mir-581; mir-582; mir-583; mir-584; mir-585; mir-586; mir-587; mir-588; mir-589; mir-590;

mir-591; mir-592; mir-593; mir-595; mir-596; mir-597; mir-598; mir-599; mir-600; mir-601; mir-602; mir-603; mir-604; mir-605; mir-606; mir-607; mir-608; mir-609; mir-610; mir-611; mir-612; mir-613; mir-614; mir-615; mir-616; mir-617; mir-618; mir-619; mir-620; mir-621; mir-622; mir-623; mir-624; mir-625; mir-626; mir-627; mir-628; mir-629; mir-630; mir-631; mir-632; mir-633; mir-634; mir-635; mir-636; mir-637; mir-638; mir-639; mir-640; mir-641; mir-642a; mir-642b; mir-643; mir-644; mir-645; mir-646; mir-647; mir-648; mir-649; mir-650; mir-651; mir-652; mir-653; mir-654; mir-655; mir-656; mir-657; mir-658; mir-659; mir-660; mir-661; mir-662; mir-663; mir-663b; mir-664; mir-665; mir-668; mir-670; mir-671; mir-675; mir-676; mir-708; mir-711; mir-718; mir-720; mir-744; mir-758; mir-759; mir-760; mir-761; mir-762; mir-764; mir-765; mir-766; mir-767; mir-769; mir-770; mir-802; mir-873; mir-874; mir-875; mir-876; mir-877; mir-885; mir-887; mir-888; mir-889; mir-890; mir-891a; mir-891b; mir-892a; mir-892b; mir-920; mir-921; mir-922; mir-924; mir-933; mir-934; mir-935; mir-936; mir-937; mir-938; mir-939; mir-940; mir-941-1; mir-941-2; mir-941-3; mir-941-4; mir-942; mir-942; mir-943; mir-944; mir-1178; mir-1179; mir-1180; mir-1181; mir-1182; mir-1183; mir-1184-1; mir-1184-2; mir-1184-3; mir-1185-1; mir-1185-2; mir-1193; mir-1197; mir-1200; mir-1202; mir-1203; mir-1204; mir-1205; mir-1206; mir-1207; mir-1208; mir-1224; mir-1225; mir-1226; mir-1227; mir-1228; mir-1229; mir-1231; mir-1233-1; mir-1233-2; mir-1234; mir-1236; mir-1237; mir-1238; mir-1243; mir-1244-1; mir-1244-2; mir-1244-3; mir-1245; mir-1246; mir-1247; mir-1248; mir-1249; mir-1250; mir-1251; mir-1252; mir-1253; mir-1254; mir-1255a; mir-1255b-1; mir-1255b-2; mir-1256; mir-1257; mir-1258; mir-1260; mir-1260b; mir-1261; mir-1262; mir-1263; mir-1264; mir-1265; mir-1266; mir-1267; mir-1268; mir-1269; mir-1270-1; mir-1270-2; mir-1271; mir-1272; mir-1273; mir-1273c; mir-1273d; mir-1273e; mir-1274a; mir-1274b; mir-1275; mir-1276; mir-1277; mir-1278; mir-1279; mir-1280; mir-1281; mir-1282; mir-1283-1; mir-1283-2; mir-1284; mir-1285-1; mir-1285-2; mir-1286; mir-1287; mir-1288; mir-1289-1; mir-1289-2; mir-1290; mir-1291; mir-1292; mir-1293; mir-1294; mir-1295; mir-1296; mir-1297; mir-1298; mir-1299; mir-1301; mir-1302-1; mir-1302-10; mir-1302-11; mir-1302-2; mir-1302-3; mir-1302-4; mir-1302-5; mir-1302-6; mir-1302-7; mir-1302-8; mir-1302-9; mir-1303; mir-1304; mir-1305; mir-1306; mir-1307; mir-1321; mir-1322; mir-1323; mir-1324; mir-1468; mir-1469; mir-1470; mir-1471; mir-1537; mir-1538; mir-1539; mir-1825; mir-1827; mir-1908; mir-1909; mir-1910; mir-1911; mir-1912; mir-1913; mir-1914; mir-1915; mir-1972-1; mir-1972-2; mir-1973; mir-1976; mir-2052; mir-2053; mir-2054; mir-2110; mir-2113; mir-2114; mir-2115; mir-2116; mir-2117; mir-2276; mir-2277; mir-2278; mir-2355; mir-2861; mir-2909; mir-3065; mir-3074; mir-3115; mir-3116-1; mir-3116-2; mir-3117; mir-3118-1; mir-3118-2; mir-3118-3; mir-3118-4; mir-3118-5; mir-3118-6; mir-3119-1; mir-3119-2; mir-3120; mir-3121; mir-3122; mir-3123; mir-3124; mir-3125; mir-3126; mir-3127; mir-3128; mir-3129; mir-3130-1; mir-3130-2; mir-3131; mir-3132; mir-3133; mir-3134; mir-3135; mir-3136; mir-3137; mir-3138; mir-3139; mir-3140; mir-3141; mir-3142; mir-3143; mir-3144; mir-3145; mir-3146; mir-3147; mir-3148; mir-3149; mir-3150; mir-3151; mir-3152; mir-3153; mir-3154; mir-3155; mir-3156-1; mir-3156-2; mir-3156-3; mir-3157; mir-3158-1; mir-3158-2; mir-3159; mir-3160-1; mir-3160-2; mir-3161; mir-3162; mir-3163; mir-3164; mir-3165; mir-3166; mir-3167; mir-3168; mir-3169; mir-3170; mir-3171; mir-3173; mir-3174; mir-3175; mir-3176; mir-3177; mir-3178; mir-3179-1; mir-3179-2; mir-3179-3; mir-3180-1; mir-3180-2; mir-3180-3; mir-3180-4; mir-3180-5; mir-3181; mir-3182; mir-3183; mir-3184; mir-3185; mir-3186; mir-3187; mir-3188; mir-3189; mir-3190; mir-3191; mir-3192; mir-3193; mir-3194; mir-3195; mir-3196; mir-3197; mir-3198; mir-3199-1; mir-3199-2; mir-3200; mir-3201; mir-3202-1; mir-3202-2; mir-3605; mir-3606; mir-3607; mir-3609; mir-3610; mir-3611; mir-3612; mir-3613; mir-3614; mir-3615; mir-3616; mir-3617; mir-3618; mir-3619; mir-3620; mir-3621; mir-3622a; mir-3622b; mir-3646; mir-3647; mir-3648; mir-3649; mir-3650; mir-3651; mir-3652; mir-3653; mir-3654; mir-3655; mir-3656mir-3657; mir-3658; mir-3659; mir-3660; mir-3661; mir-3662; mir-3663; mir-3664; mir-3665; mir-3666; mir-3667; mir-3668; mir-3669; mir-3670; mir-3670; mir-3671; mir-3671; mir-3673; mir-3673; mir-3675; mir-3675; mir-3676; mir-3663; mir-3677; mir-3678; mir-3679; mir-3680; mir-3681; mir-3682; mir-3683; mir-3684; mir-3685; mir-3686; mir-3687; mir-3688; mir-3689a; mir-3689b; mir-3690; mir-3691; mir-3692; mir-3713; mir-3714; mir-3907; mir-3908; mir-3909; mir-3910-1; mir-3910-2; mir-3911; mir-3912; mir-3913-1; mir-3913-2; mir-3914-1; mir-3914-2; mir-3915; mir-3916; mir-3917; mir-3918; mir-3919; mir-3920; mir-3921; mir-3922; mir-3923; mir-3924; mir-3925; mir-3926-1; mir-3926-2; mir-3927; mir-3928; mir-3929; mir-3934; mir-3935; mir-3936; mir-3937; mir-3938; mir-3939; mir-3940; mir-3941; mir-3942; mir-3943; mir-3944; mir-3945; mir-4251; mir-4252; mir-4253; mir-4254; mir-4255; mir-4256; mir-4257; mir-4258; mir-4259; mir-4260; mir-4261; mir-4262; mir-4263; mir-4264; mir-4265; mir-4266; mir-4267; mir-4268; mir-4269; mir-4270; mir-4271; mir-4272; mir-4273; mir-4274; mir-4275; mir-4276; mir-4277; mir-4278; mir-4279; mir-4280; mir-4281; mir-4282; mir-4283-1; mir-4283-2; mir-4284; mir-4285; mir-4286; mir-4287; mir-4288; mir-4289; mir-4290; mir-4291; mir-4292; mir-4293; mir-4294; mir-4295; mir-4296; mir-4297; mir-4298; mir-4299; mir-4300; mir-4301; mir-4302; mir-4303; mir-4304; mir-4305; mir-4306; mir-4307; mir-4308; mir-4309; mir-4310; mir-4311; mir-4312; mir-4313; mir-4314; mir-4315-1; mir-4315-2; mir-4316; mir-4317; mir-4318; mir-4319; mir-4320; mir-4321; mir-4322; mir-4323; mir-4324; mir-4325; mir-4326; mir-4327; mir-4328; mir-4329; mir-4329; and mir-4330.

The present invention relates to formulations that contain cell-derived or secreted miRNAs obtainable from the cell populations or constructs described herein. Alternatively, the formulations contain nucleic acid molecules comprising the sequence of an miRNA described herein. In one embodiment, the formulations contain one or more of the individual miRNAs that may be used to provide a regenerative effect to a native kidney. Combinations of the individual miRNAs may be suitable for providing such an effect. Exemplary combinations include two or more of the following: miR-21; miR-23a; miR-30c; miR-1224; miR-23b; miR-92a; miR-100; miR-125b-5p; miR-195; miR-10a-5p; and any combination thereof. Another exemplary combination includes two or more of the following: miR-30b-5p, miR-449a, miR-146a, miR-130a, miR-23b, miR-21, miR-124, miR-151, and any combination thereof. In one embodiment, the combination of miRNAs may include 2, 3, 4, 5, 6, 7, 8, 9, 10, or more individual miRNAs. Those of ordinary skill in the art will appreciate that other miRNAs and combinations of mirRNAs may be suitable for use in the present invention. Sources of additional miRNAs include miRBase at http://mirbase.org, which is hosted and maintained in the Faculty of Life Sciences at the University of Manchester.

In one embodiment, formulations contain secreted products that comprise paracrine and/or juxtacrine factors, such as alpha-1 microglobulin, beta-2-microglobulin, calbindin, clusterin, connective tissue growth factor, cystatin-C, glutathione-S-transferase alpha, kidney injury moleculte-1, neutraphil gelatinase-associated lipocalin, osteopontin, trefoil factor 3, tam-horsfall urinary glycoprotein, tissue-inhibitor of metallo proteinase 1, vascular endothelial growth factor, fibronectin, interleukin-6, monocyte chemotactic protein-1.

In general, paracrine factors are molecules synthesized by a cell that can diffuse over small distances to induce or effect changes in a neighboring cell, i.e., a paracrine interaction. The diffusable molecules are referred to as paracrine factors. In general, juxtacrine factors are molecules that facilitate intercellular communication that is transmitted via oligosaccharide, lipid, or protein components of a cell membrane, and may affect either the emitting cell or the immediately adjacent cells. Juxtacrine signaling typically involves physical contact between the two cells involved.

In yet another embodiment, the present invention concerns a formulation containing one or more isolated renal-cell derived secreted vesicles, as described herein. Those of ordinary skill in the art will appreciate that various types of formulations containing the secreted vesicles will be suitable.

In another aspect, the present invention provides methods of preparing formulations that contain renal cell secreted products, e.g., vesicles. In one embodiment, the method includes the steps of providing a renal cell population, including admixtures of one or more enriched renal cell populations. In another embodiment, the method further includes the step of culturing the population under suitable conditions. The conditions may be low oxygen conditions. In another embodiment, the method further includes the step of isolating the secreted products from the renal cell population. The secreted vesicles may be obtained from the cell culture media of the cell population. After the secreted products are isolated they can then be used as part of a formulation described herein. In one other embodiment, the renal cells that provide the secreted products are characterized by vesicle production and/or secretion that is bioresponsive to oxygen levels, such that a reduction in the oxygen tension of the culture system results in an induction of vesicle production and/or secretion. In one embodiment, the vesicle production and/or secretion is induced when the cell population is cultured under conditions where the cells are subjected to a reduction in available oxygen levels in the culture system as compared to a cell population cultured at normal atmospheric (~21%) levels of available oxygen. In one embodiment, the cell populations cultured in lower oxygen conditions produce and/or secrete greater levels of vesicles relative to cell populations cultured at normal oxygen conditions. In general, the culturing of cells at reduced levels of available oxygen (also referred to as hypoxic culture conditions) means that the level of reduced oxygen is reduced relative to the culturing of cells at normal atmospheric levels of available oxygen (also referred to as normal or normoxic culture conditions). In one embodiment, hypoxic cell culture conditions include culturing cells at about less than 1% oxygen, about less than 2% oxygen, about less than 3% oxygen, about less than 4% oxygen, or about less than 5% oxygen. In another embodiment, normal or normoxic culture conditions include culturing cells at about 10% oxygen, about 12% oxygen, about 13% oxygen, about 14% oxygen, about 15% oxygen, about 16% oxygen, about 17% oxygen, about 18% oxygen, about 19% oxygen, about 20% oxygen, or about 21% oxygen. In a preferred embodiment, the method provides for the isolation of exosomes and/or microvesicles from renal cells.

In one embodiment, the formulation contains products that are secreted from renal cells. The products may be secreted from renal cells that are not on a scaffold, e.g., the cells are not part of a construct as described herein.

In another embodiment, the formulation contains products that are secreted by renal cells that have been seeded on a scaffold, e.g., a construct. The construct includes one or more enriched renal cell populations, or an admixture thereof, that are directly seeded on or in a scaffold.

In another aspect, the present invention provides in vitro methods for screening/optimizing/monitoring the biotherapeutic efficacy of one or more enriched renal cell populations, and admixtures or constructs containing the same prior to formulation. In one embodiment, the method includes the step of providing one or more test populations, test admixture or test construct (the "test article"). In another embodiment, the method includes the step of culturing the test article under suitable conditions, as described herein. In one other embodiment, the method includes the step of collecting cell culture media from the cultured test article. This media may be referred to as "conditioned media" and it is expected to contain products secreted by the renal cells of the test article.

In one other aspect, the conditioned media may be used to conduct one or more in vitro assays in order to test the biotherapeutic efficacy of the test article. In one embodiment, the conditioned media is subjected to an epithelial-mesenchymal transition (EMT) assay. The assay may test for EMT induced by TGFβ1. Examples 18 provide exemplary protocols for this assay.

In another embodiment, the conditioned media is subjected to the detection of RNAs, e.g., via PCR-based assays, and/or vesicles or exosomes, e.g., via FACS. In one other embodiment, the conditioned media is subjected to a signaling pathway assay, e.g., immune response (e.g., NFκB), fibrotic response (PAI-1), and angiogenesis. Examples 15-17 provides exemplary protocols for these assays.

6. Methods of Use

In another aspect, the formulations of the present invention may be administered for the treatment of disease. For example, bioactive cells may be administered to a native organ as part of a formulation described herein. In one embodiment, the bioactive cells may be sourced from the native organ that is the subject of the administration or from a source that is not the target native organ.

In one aspect, the present invention provides methods for the treatment of a kidney disease, anemia, or EPO deficiency in a subject in need with the formulations containing kidney cell populations and admixtures of kidney cells as described herein. In one embodiment, the method comprises administering to the subject a formulation containing a composition that includes a first kidney cell population enriched for EPO-producing cells. In another embodiment, the first cell population is enriched for EPO-producing cells, glomerular cells, and vascular cells. In one embodiment, the first kidney cell population is a B4' cell population. In another embodiment, the composition may further include one or more additional kidney cell populations. In one embodiment, the additional cell population is a second cell population not enriched for EPO-producing cells. In another embodiment, the additional cell population is a second cell population not enriched for EPO-producing cells, glomerular cells, or vascular cells. In another embodiment, the composition also includes a kidney cell population or admixture of kidney cells deposited in, deposited on, embedded in, coated with, suspended in, or entrapped in a biomaterial to form an implantable construct, as described herein, for the treatment of a disease or disorder described herein. In one embodiment, the cell populations are used alone or in combination with other cells or biomaterials, e.g., hydrogels, porous scaffolds, or native or synthetic peptides or proteins, to stimulate regeneration in acute or chronic disease states.

In another aspect, the effective treatment of a kidney disease, anemia, or EPO deficiency in a subject by the methods of the present invention can be observed through various indicators of erythropoiesis and/or kidney function. In one embodiment, the indicators of erythroid homeostasis include, without limitation, hematocrit (HCT), hemoglobin (HB), mean corpuscular hemoglobin (MCH), red blood cell count (RBC), reticulocyte number, reticulocyte %, mean corpuscular volume (MCV), and red blood cell distribution width (RDW). In one other embodiment, the indicators of kidney function include, without limitation, serum albumin, albumin to globulin ratio (A/G ratio), serum phosphorous, serum sodium, kidney size (measurable by ultrasound), serum calcium, phosphorous:calcium ratio, serum potassium, proteinuria, urine creatinine, serum creatinine, blood nitrogen urea (BUN), cholesterol levels, triglyceride levels and glomerular filtration rate (GFR). Furthermore, several indicators of general health and well-being include, without limitation, weight gain or loss, survival, blood pressure (mean systemic blood pressure, diastolic blood pressure, or systolic blood pressure), and physical endurance performance.

In another embodiment, an effective treatment with a bioactive renal cell formulation is evidenced by stabilization of one or more indicators of kidney function. The stabilization of kidney function is demonstrated by the observation of a change in an indicator in a subject treated by a method of the present invention as compared to the same indicator in a subject that has not been treated by a method of the present invention. Alternatively, the stabilization of kidney function may be demonstrated by the observation of a change in an indicator in a subject treated by a method of the present invention as compared to the same indicator in the same subject prior to treatment. The change in the first indicator may be an increase or a decrease in value. In one embodiment, the treatment provided by the present invention may include stabilization of blood urea nitrogen (BUN) levels in a subject where the BUN levels observed in the subject are lower as compared to a subject with a similar disease state who has not been treated by the methods of the present invention. In one other embodiment, the treatment may include stabilization of serum creatinine levels in a subject where the serum creatinine levels observed in the subject are lower as compared to a subject with a similar disease state who has not been treated by the methods of the present invention. In another embodiment, the treatment may include stabilization of hematocrit (HCT) levels in a subject where the HCT levels observed in the subject are higher as compared to a subject with a similar disease state who has not been treated by the methods of the present invention. In another embodiment, the treatment may include stabilization of red blood cell (RBC) levels in a subject where the RBC levels observed in the subject are higher as compared to a subject with a similar disease state who has not been treated by the methods of the present invention. Those of ordinary skill in the art will appreciate that one or more additional indicators described herein or known in the art may be measured to determine the effective treatment of a kidney disease in the subject.

In another aspect, the present invention concerns formulations for use in methods of providing erythroid homeostasis in a subject. In one embodiment, the method includes the step of (a) administering to the subject a formulation containing a renal cell population, e.g., B2 or B4', or admixture of renal cells, e.g., B2/B4' and/or B2/B3, or an enriched renal cell population, as described herein; and (b) determining, in a biological sample from the subject, that the level of an erythropoiesis indicator is different relative to the indicator level in a control, wherein the difference in indicator level (i) indicates the subject is responsive to the administering step (a), or (ii) is indicative of erythroid homeostasis in the subject. In another embodiment, the method includes the step of (a) administering to the subject a formulation comprising a renal cell population or admixture of renal cells as described herein; and (b) determining, in a biological sample from the subject, that the level of an erythropoiesis indicator is different relative to the indicator level in a control, wherein the difference in indicator level (i) indicates the subject is responsive to the administering step (s), or (ii) is indicative of erythroid homeostasis in the subject. In another embodiment, the method includes the step of (a) providing a biomaterial or biocompatible polymeric scaffold; (b) depositing a renal cell population or admixture of renal cells of the present invention on or within the biomaterial or scaffold in a manner described herein to form an implantable construct; (c) preparing a formulation containing the construct; (d) implanting the construct into the subject; and (e) determining, in a biological sample from the subject, that the level of an erythropoiesis indicator is different relative to the indicator level in a control, wherein the difference in indicator level (i) indicates the subject is responsive to the administering step (a), or (ii) is indicative of erythroid homeostasis in the subject.

In another aspect, the present invention concerns formulations for use in methods of providing both stabilization of kidney function and restoration of erythroid homeostasis to a subject in need, said subject having both a deficit in kidney function and an anemia and/or EPO-deficiency. In one embodiment, the method includes the step of administering a formulation containing a renal cell population or admixture of renal cells as described herein that contain at least one of the following cell types: tubular-derived cells, glomerulus-derived cells, insterstitium-derived cells, collecting duct-derived cells, stromal tissue-derived cells, or cells derived from the vasculature. In another embodiment, the population or admixture contains both EPO-producing cells and tubular epithelial cells, the tubular cells having been identified by at least one of the following markers: megalin, cubilin, hyaluronic acid synthase 2 (HAS2), Vitamin D3 25-Hydroxylase (CYP2D25), N-cadherin (Ncad), E-cadherin (Ecad), Aquaporin-1 (Aqp1), Aquaporin-2 (Aqp2), RAB17, member RAS oncogene family (Rab17), GATA binding protein 3 (Gata3), FXYD domain-containing ion transport regulator 4 (Fxyd4), solute carrier family 9 (sodium/hydrogen exchanger), member 4 (Slc9a-4), aldehyde dehydrogenase 3 family, member B1 (Aldh3b1), aldehyde dehydrogenase 1 family, member A3 (Aldh1a3), and Calpain-8 (Capn8). In this embodiment, treatment of the subject would be demonstrated by an improvement in at least one indicator of kidney function concomitant with improvement in at least one indicator of erythropoiesis, compared to either an untreated subject or to the subject's pre-treatment indicators.

In one aspect, the present invention provides formulations for use in methods of (i) treating a kidney disease, anemia, or an EPO-deficiency; (ii) stabilizing kidney function, (iii) restoring erythroid homeostasis, or (iv) any combination of thereof by administering a renal cell population enriched for EPO-producing cells or admixture of renal cells containing a cell population enriched for EPO-producing cells as described herein, wherein the beneficial effects of the administration are greater than the effects of administering a cell population not enriched for EPO-producing cells. In another embodiment, the enriched cell population provides an improved level of serum blood urea nitrogen (BUN). In another embodiment, the enriched cell population provides an improved retention of protein in the serum. In another embodiment, the enriched cell population provides improved levels of serum cholesterol and/or triglycerides. In another embodiment, the enriched cell population provides an improved level of Vitamin D. In one embodiment, the enriched cell population provides an improved phosphorus:calcium ratio as compared to a non-enriched cell population. In another embodiment, the enriched cell population provides an improved level of hemoglobin as compared to a non-enriched cell population. In a further embodiment, the enriched cell population provides an improved level of serum creatinine as compared to a non-enriched cell population. In yet another embodiment, the enriched cell population provides an improved level of hematocrit as compared to a non-enriched cell population. In a further embodiment, the enriched cell population provides an improved level of red blood cell number (RBC#) as compared to a non-enriched cell population. In one embodiment, the improved level of hematocrit is restored to 95% normal healthy level. In a further embodiment, the enriched cell population provides an improved reticulocyte number as compared to a non-enriched cell population. In other embodiments, the enriched cell population provides an improved reticulocyte percentage as compared to a non-enriched cell population. In yet other embodiments, the enriched cell population provides an improved level of red blood cell volume distribution width (RDW) as compared to a non-enriched cell population. In yet another embodiment, the enriched cell population provides an improved level of hemoglobin as compared to a non-enriched cell population. In yet another embodiment, the enriched cell population provides an erythroietic response in the bone marrow, such that the marrow cellularity is near-normal and the myeloid:erythroid ratio is near normal.

In another aspect, the present invention provides formulations for use in methods of (i) treating a kidney disease, anemia, or an EPO-deficiency; (ii) stabilizing kidney function, (iii) restoring erythroid homeostasis, or (iv) any combination of thereof by administering an enriched cell population, wherein the beneficial effects of administering a renal cell population or admixture of renal cell populations described herein are characterized by improved erythroid homeostasis when compared to the beneficial effects provided by the administering of recombinant EPO (rEPO). In one embodiment, the population or admixture, when administered to a subject in need provides improved erythroid homeostasis (as determined by hematocrit, hemoglobin, or RBC#) when compared to the administration of recombinant EPO protein. In one embodiment, the population or admixture, when administered provides an improved level of hematocrit, RBC, or hemoglobin as compared to recombinant EPO, being no greater than about 10% lower or higher than hematocrit in a control. In a further embodiment, a single dose or delivery of the population or admixture, when administered provides improvement in erythroid homeostasis (as determined by increase in hematocrit, hemoglobin, or RBC#) in the treated subject for a period of time that significantly exceeds the period of time that a single dose or delivery of the recombinant EPO protein provides improvement in erythroid homeostasis. In another embodiment, the population or admixture, when administered at a dose described herein does not result in hematocrit, hemoglobin, or RBC# greater than about 110% of normal levels in matched healthy controls. In a further embodiment, the population or admixture, when administered at a dose described herein provides superior erythroid homeostasis (as determined by hematocrit, hemoglobin, or RBC#) compared to recombinant EPO protein delivered at a dose described herein. In another embodiment, the recombinant EPO is delivered at a dose of about 100 IU/kg, about 200 IU/kg, about 300 IU/kg, about 400 IU/kg, or about 500 IU/kg. Those of ordinary skill in the art will appreciate that other dosages of recombinant EPO known in the art may be suitable.

Another embodiment of the present invention is directed to the use of formulations containing at least one cell population, including enriched cell populations and admixtures thereof, described herein, or an implantable construct described herein, or secreted products as described herein, for the preparation of a medicament for the treatment of a kidney disease, anemia, or EPO deficiency in a subject in need, the providing of erythroid homeostasis in a subject in need, the improvement of kidney function in a subject in need, or providing a regenerative effect to a native kidney.

Another embodiment of the present invention is directed to formulations containing specific enriched cell population(s) (described herein) for the treatment of a kidney disease of a specific etiology, based on selection of specific cell subpopulation(s) based on specific verified therapeutic attributes.

In yet another aspect, the present invention provides formulations for use in methods of treating a kidney disease in a subject in need, comprising: administering to the subject a formulation comprising an admixture of mammalian renal cells comprising a first cell population, B2, comprising an isolated, enriched population of tubular cells having a density between 1.045 g/mL and 1.052 g/mL, and a second cell population, B4', comprising erythropoietin (EPO)-producing cells and vascular cells but depleted of glomerular cells having a density between 1.063 g/mL and 1.091 g/mL, wherein the admixture does not include a B1 cell population comprising large granular cells of the collecting duct and tubular system having a density of <1.045 g/ml, or a B5 cell population comprising debris and small cells of low granularity and viability with a density >1.091 g/ml. In certain embodiments, the method includes determining in a test sample from the subject that the level of a kidney function indicator is different relative to the indicator level in a control, wherein the difference in indicator level is indicative of a reduction in decline, stabilization, or an improvement of one or more kidney functions in the subject. In one embodiment, the B4' cell population used in the method is characterized by expression of a vascular marker. In certain embodiments, the B4' cell population used in the method is not characterized by expression of a glomerular marker. In one embodiment, the admixture of cells used in the method is capable of oxygen-tunable erythropoietin (EPO) expression. In certain embodiments, the kidney disease to be treated by the methods of the invention is accompanied by an erythropoietin (EPO) deficiency. In certain embodiments, the EPO deficiency is anemia. In some embodiments, the EPO deficiency or anemia occurs secondary to renal failure in the subject. In some other embodiments, the EPO deficiency or anemia occurs secondary to a disorder selected from the group consisting of chronic renal failure, primary EPO deficiency, chemotherapy or anti-viral therapy, non-myeloid cancer, HIV infection, liver disease, cardiac failure, rheumatoid arthritis, or multi-organ system failure. In certain embodiments, the composition used in the method further comprises a biomaterial comprising one or more biocompatible synthetic polymers and/or naturally-occurring proteins or peptides, wherein the admixture is coated with, deposited on or in, entrapped in, suspended in, embedded in and/or otherwise combined with the biomaterial. In certain embodiments, the admixture used in the formulations of the invention is derived from mammalian kidney tissue or cultured mammalian kidney cells. In other embodiments, the admixture is derived from a kidney sample that is autologous to the subject in need. In one embodiment, the sample is a kidney biopsy. In other embodiments, the formulation contains an admixture derived from a non-autologous kidney sample.

In yet another aspect, the invention provides a use of a formulation containing the cell preparations and admixtures described herein or an implantable construct of the instant invention for the preparation of a medicament useful in the treatment of a kidney disease, anemia or EPO deficiency in a subject in need thereof.

In another aspect, the present invention provides formulations for use in methods for the regeneration of a native kidney in a subject in need thereof. In one embodiment, the method includes the step of administering or implanting a cell population, admixture, or construct described herein to the subject. A regenerated native kidney may be characterized by a number of indicators including, without limitation, development of function or capacity in the native kidney, improvement of function or capacity in the native kidney, and the expression of certain markers in the native kidney. In one embodiment, the developed or improved function or capacity may be observed based on the various indicators of erythroid homeostasis and kidney function described above. In another embodiment, the regenerated kidney is characterized by differential expression of one or more stem cell markers. The stem cell marker may be one or more of the following: SRY (sex determining region Y)-box 2 (Sox2); Undifferentiated Embryonic Cell Transcription Factor (UTF1); Nodal Homolog from Mouse (NODAL); Prominin 1 (PROM1) or CD133 (CD133); CD24; and any combination thereof (see Hagan et al. PCT/US2011/036347 incorporated herein by reference in its entirety). In another embodiment, the expression of the stem cell marker(s) is up-regulated compared to a control.

The cell populations described herein, including enriched cell populations and admixtures thereof, as well as constructs containing the same may be used to provide a regenerative effect to a native kidney. The effect may be provided by the cells themselves and/or by products secreted from the cells. The regenerative effect may be characterized by one or more of the following: a reduction in epithelial-mesenchymal transition (which may be via attenuation of TGF-β signaling); a reduction in renal fibrosis; a reduction in renal inflammation; differential expression of a stem cell marker in the native kidney; migration of implanted cells and/or native cells to a site of renal injury, e.g., tubular injury; engraftment of implanted cells at a site of renal injury, e.g., tubular injury; stabilization of one or more indicators of kidney function (as described herein); restoration of erythroid homeostasis (as described herein); and any combination thereof.

7. Methods of Monitoring Regeneration

In another aspect, the present invention provides a prognostic method for monitoring regeneration of a native kidney following administration or implantation of a formulation containing a cell population, admixture, or construct described herein to the subject. In one embodiment, the method includes the step of detecting the level of marker expression in a test sample obtained from the subject and in a control sample, wherein a higher level of expression of the marker in the test sample, as compared to the control sample, is prognostic for regeneration of the native kidney in the subject. In another embodiment, the method includes the detection of expression of one or more stem cell markers in the sample. The stem cell marker may be selected from Sox2; UTF1; NODAL; CD133; CD24; and any combination thereof (see Example 11 of Ilagan et al. PCT/US2011/036347). The detecting step may include determining that expression of the stem cell marker(s) is up-regulated or higher in the test sample relative to a control sample, wherein the higher level of expression is prognostic for regeneration of the subject's native kidney. In one other embodiment, mRNA expression of the stem cell marker(s) is detected. In other embodiments, the detection of mRNA expression may be via a PCR-based method, e.g., qRT-PCR. In situ hybridization may also be used for the detection of mRNA expression. In another embodiment, polypeptide expression of the stem cell marker may also be detected using an anti-stem cell marker agent. In one other embodiment, the agent is an antibody against the marker. In another embodiment, stem cell marker polypeptide expression is detected using immunohistochemistry or a Western Blot. Those of ordinary skill in the art will appreciate other methods for detecting mRNA and/or polypeptide expression of markers.

In another aspect, the invention provides methods for prognostic evaluation of a patient following implantation or administration of a formulation containing a cell population, admixture, or construct described herein. In one embodiment, the method includes the step of detecting the level of marker expression in a test sample obtained from said subject; (b) determining the expression level in the test sample relative to the level of marker expression relative to a control sample (or a control reference value); and (c) predicting regenerative prognosis of the patient based on the determination of marker expression levels, wherein a higher level of expression of marker in the test sample, as compared to the control sample (or a control reference value), is prognostic for regeneration in the subject.

In one other aspect, the present invention provides prognostic methods for monitoring regeneration of a native kidney following administration or implantation of a formulation containing a cell population, admixture, or construct described herein to the subject, in which a non-invasive method is used. As an alternative to a tissue biopsy, a regenerative outcome in the subject receiving treatment can be assessed from examination of a bodily fluid, e.g., urine. It has been discovered that microvesicles obtained from subject-derived urine sources contain certain components including, without limitation, specific proteins and miRNAs that are ultimately derived from the renal cell populations impacted by treatment with the cell populations of the present invention. These components may include factors involved in stem cell replication and differentiation, apoptosis, inflammation and immuno-modulation. A temporal analysis of microvesicle-associated miRNA/protein expression patterns allows for continuous monitoring of regenerative outcomes within the kidney of subjects receiving the cell populations, admixtures, or constructs of the present invention. Example 19 describes exemplary protocols for analysis of the urine of subjects.

These kidney-derived vesicles and/or the luminal contents of kidney derived vesicles shed into the urine of a subject may be analyzed for biomarkers indicative of regenerative outcome.

In one embodiment, the present invention provides methods of assessing whether a kidney disease (KD) patient is responsive to treatment with a therapeutic formulation. The method may include the step of determining or detecting the amount of vesicles or their luminal contents in a test sample obtained from a KD patient treated with the therapeutic, as compared to or relative to the amount of vesicles in a control sample, wherein a higher or lower amount of vesicles or their luminal contents in the test sample as compared to the amount of vesicles or their luminal contents in the control sample is indicative of the treated patient's responsiveness to treatment with the therapeutic.

The present invention also provides a method of monitoring the efficacy of treatment with a therapeutic in a KD patient. In one embodiment, the method includes the step of determining or detecting the amount of vesicles in a test sample obtained from a KD patient treated with the therapeutic, as compared to or relative to the amount of vesicles or their luminal contents in a control sample, wherein a higher or lower amount of vesicles or their luminal contents in the test sample as compared to the amount of vesicles or their luminal contents in the control sample is indicative of the efficacy of treatment with the therapeutic in the KD patient.

The present invention provides a method of identifying a patient subpopulation for which an agent is effective to treat kidney disease (KD). In one embodiment, the method includes the step of determining a correlation between efficacy of the agent and the presence of an amount of vesicles or their luminal contents in samples from the patient subpopulation as compared to the amount of vesicles or their luminal contents in a sample obtained from a control sample, wherein a higher or lower amount of vesicles in the samples from the patient subpopulation as compared to the amount of vesicles or their luminal contents in the control sample is indicative that the agent is effective to treat KD in the patient subpopulation.

The determining or detecting step may include analyzing the amount of miRNA or other secreted products that may exist in the test sample (see Example 19).

The non-invasive prognostic methods may include the step of obtaining a urine sample from the subject before and/or after administration or implantation of a cell population, admixture, or construct described herein. Vesicles and other secreted products may be isolated from the urine samples using standard techniques including without limitation, centrifugation to remove unwanted debris (Thou et al. 2008. Kidney Int. 74(5):613-621; Skog et al. U.S. Published Patent Application No. 20110053157, each of which is incorporated herein by reference in its entirety).

The present invention relates to non-invasive methods to detect regenerative outcome in a subject following treatment. The methods involve detection of vesicles or their luminal contents in urine from a treated subject. The luminal contents may be one or more miRNAs. The detection of combinations or panels of the individual miRNAs may be suitable for such prognostic methods. Exemplary combinations include two or more of the following: miR-24; miR-195; miR-871; miR-30b-5p; miR-19b; miR-99a; miR-429; let-7f; miR-200a; miR-324-5p; miR-10a-5p; and any combination thereof. In one embodiment, the combination of miRNAs may include 2, 3, 4, 5, 6, 7, 8, 9, 10, 11, or more individual miRNAs. Those of ordinary skill in the art will appreciate that other miRNAs and combinations of miRNAs may be suitable for use in such prognostic methods. Sources of additional miRNAs include miRBase at http://mirbase.org, which is hosted and maintained in the Faculty of Life Sciences at the University of Manchester.

Those of skill in the art will appreciate that the prognostic methods for detecting regeneration may be suitable for subjects treated with other therapeutics known in the art, apart from the cell populations and constructs described herein.

In some embodiments, the determining step comprises the use of a software program executed by a suitable processor for the purpose of (i) measuring the differential level of marker expression (or vesicles/vesicle contents) in a test sample and a control; and/or (ii) analyzing the data obtained from measuring differential level of marker expression in a test sample and a control. Suitable software and processors are well known in the art and are commercially available. The program may be embodied in software stored on a tangible medium such as CD-ROM, a floppy disk, a hard drive, a DVD, or a memory associated with the processor, but persons of ordinary skill in the art will readily appreciate that the entire program or parts thereof could alternatively be executed by a device other than a processor, and/or embodied in firmware and/or dedicated hardware in a well known manner.

Following the determining step, the measurement results, findings, diagnoses, predictions and/or treatment recommendations are typically recorded and communicated to technicians, physicians and/or patients, for example. In certain embodiments, computers will be used to communicate such information to interested parties, such as, patients and/or the attending physicians. In some embodiments, the assays will be performed or the assay results analyzed in a country or jurisdiction which differs from the country or jurisdiction to which the results or diagnoses are communicated.

In a preferred embodiment, a prognosis, prediction and/or treatment recommendation based on the level of marker expression measured in a test subject having a differential level of marker expression is communicated to the subject as soon as possible after the assay is completed and the prognosis and/or prediction is generated. The results and/or related information may be communicated to the subject by the subject's treating physician. Alternatively, the results may be communicated directly to a test subject by any means of communication, including writing, electronic forms of communication, such as email, or telephone. Communication may be facilitated by use of a computer, such as in case of email communications. In certain embodiments, the communication containing results of a prognostic test and/or conclusions drawn from and/or treatment recommendations based on the test, may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, prognosis and/or prediction of regeneration, and communicating of assay results or prognoses, may be carried out in diverse (e.g., foreign) jurisdictions.

In another aspect, the prognostic methods described herein provide information to an interested party concerning the regenerative success of the implantation or administration.

In all embodiments, the methods of providing a regenerated kidney to a subject in need of such treatment as described herein may include the post-implantation step of prognostic evaluation of regeneration as described above.

8. Bioactive Cell Formulations

The formulations described herein incorporate biomaterials having properties which create a favorable environment for the active agent, such as bioactive renal cells, to be administered to a subject. In one embodiment, the formulation contains a first biomaterial that provides a favorable environment from the time the active agent is formulated with the biomaterial up until the point of administration to the subject. In one other embodiment, the favorable environment concerns the advantages of having bioactive cells suspended in a substantially solid state versus cells in a fluid (as described herein) prior to administration to a subject. In another embodiment, the first biomaterial is a temperature-sensitive biomaterial. The temperature-sensitive biomaterial may have (i) a substantially solid state at about 8° C. or below, and (ii) a substantially liquid state at ambient temperature or above. In one embodiment, the ambient temperature is about room temperature.

In another aspect, the formulation contains bioactive cells combined with a second biomaterial that provides a favorable environment for the combined cells from the time of formulation up until a point after administration to the subject. In one embodiment, the favorable environment provided by the second biomaterial concerns the advantages of administering cells in a biomaterial that retains structural integrity up until the point of administration to a subject and for a period of time after administration. In one embodiment, the structural integrity of the second biomaterial following implantation is minutes, hours, days, or weeks. In one embodiment, the structural integrity is less than one month, less than one week, less than one day, or less than one hour. The relatively short term structural integrity provides a formulation that can deliver the active agent and biomaterial to a target location in a tissue or organ with controlled handling, placement or dispersion without being a hindrance or barrier to the interaction of the incorporated elements with the tissue or organ into which it was placed.

In another embodiment, the second biomaterial is a temperature-sensitive biomaterial that has a different sensitivity than the first biomaterial. The second biomaterial may have (i) a substantially solid state at about ambient temperature or below, and (ii) a substantially liquid state at about 37° C. or above. In one embodiment, the ambient temperature is about room temperature.

In one embodiment, the second biomaterial is crosslinked beads. The crosslinked beads may have finely tunable in vivo residence times depending on the degree of crosslinking, as described herein. In another embodiment, the crosslinked beads comprise bioactive cells and are resistant to enzymatic degradation as described herein.

The formulations of the present invention may include the first biomaterial combined with an active agent, e.g., bioactive cells, with or without a second biomaterial combined with an active agent, e.g., bioactive cells. Where a formulation includes a second biomaterial, it may be a temperature sensitive bead and/or a crosslinked bead. Various representative formulations are provided in the examples below (see also FIGS. 3-7).

The bioactive cell preparations, admixtures, and/or constructs described herein can be administered as bioactive cell formulations. In one aspect, the formulations include the cells and one or more biomaterials that provide stability to the bioactive cell preparations, admixtures, and/or constructs described herein. In one embodiment, the biomaterial is a temperature-sensitive biomaterial that can maintain at least two different phases or states depending on temperature. The biomaterial is capable of maintaining a first state at a first temperature, a second state at a second temperature, and/or a third state at a third temperature. The first, second or third state may be a substantially solid, a substantially liquid, or a substantially semi-solid or semi-liquid state. In one embodiment, the biomaterial has a first state at a first temperature and a second state at a second temperature, wherein the first temperature is lower than the second temperature.

In one other embodiment, the state of the temperature-sensitive biomaterial is a substantially solid state at a temperature of about 8° C. or below. In other embodiments, the substantially solid state is maintained at about 1° C., about 2° C., about 3° C., about 4° C., about 5° C., about 6° C., about 7° C., or about 8° C. In one embodiment, the substantially solid state has the form of a gel. In other embodiments, the state of the temperature-sensitive biomaterial is a substantially liquid state at ambient temperature or above. In one embodiment, the substantially liquid state is maintained at about 31° C., about 32° C., about 33° C., about 34° C., about 35° C., about 36° C., or about 37° C. In one embodiment, the ambient temperature is about room temperature.

In another embodiment, the state of the temperature-sensitive biomaterial is a substantially solid state at a temperature of about ambient temperature or below. In one embodiment, the ambient temperature is about room temperature. In another embodiment, the substantially solid state is maintained at about 17° C., about 16° C., about 15° C., about 14° C., about 13° C., about 12° C., about 11° C., about 10° C., about 9° C., about 8° C., about 7° C., about 6° C., about 5° C., about 4° C., about 3° C., about 2° C., or about 1° C. In one embodiment, the substantially solid state has the form of a bead. In another embodiment, the state of the temperature-sensitive biomaterial is a substantially liquid state at a temperature of about 37° C. or above. In one other embodiment, the substantially solid state is maintained at about 37° C., about 38° C., about 39° C., or about 40° C.

The temperature-sensitive biomaterials may be provided in the form of a solution, in the form of beads, or in other suitable forms described herein and/or known to those of ordinary skill in the art. The cell populations and preparations described herein may be coated with, deposited on, embedded in, attached to, seeded, suspended in, or entrapped in a temperature-sensitive biomaterial. Alternatively, the temperature-sensitive biomaterial may be provided without any cells, such as, for example in the form of spacer beads.

In other embodiments, the temperature-sensitive biomaterial has a transitional state between a first state and a second state. In one embodiment, the transitional state is a solid-to-liquid transitional state between a temperature of about 8° C. and about ambient temperature. In one embodiment, the ambient temperature is about room temperature. In one other embodiment, the solid-to-liquid transitional state occurs at one or more temperatures of about 8° C., about 9° C., about 10° C., about 11° C., about 12° C., about 13° C., about 14° C., about 15° C., about 16° C., about 17° C., and about 18° C.

The temperature-sensitive biomaterials have a certain viscosity at a given temperature measured in centipoise (cP). In one embodiment, the biomaterial has a viscosity at 25° C. of about 1 cP to about 5 cP, about 1.1 cP to about 4.5 cP, about 1.2 cP to about 4 cP, about 1.3 cP to about 3.5 cP, about 1.4 cP to about 3.5 cP, about 1.5 cP to about 3 cP, about 1.55 cP to about 2.5 cP, or about 1.6 cP to about 2 cP. In another embodiment, the 0.75% (w/v) solution has a viscosity at 37° C. of about 1.0 cP to about 1.15 cP. The viscosity at 37° C. may be about 1.0 cP, about 1.01 cP, about 1.02 cP, about 1.03 cP, about 1.04 cP, about 1.05 cP, about 1.06 cP, about 1.07 cP, about 1.08 cP, about 1.09 cP, about 1.10 cP, about 1.11 cP, about 1.12 cP, about 1.13 cP, about 1.14 cP, or about 1.15 cP. In one other embodiment, the biomaterial is a gelatin solution. The gelatin is present at about 0.5%, about 0.55%, about 0.6%, about 0.65%, about 0.7%, about 0.75%, about 0.8%, about 0.85%, about 0.9%, about 0.95% or about 1%, (w/v) in the solution. In one example, the biomaterial is a 0.75% (w/v) gelatin solution in PBS. In one embodiment, the 0.75% (w/v) solution has a viscosity at 25° C. of about 1.6 cP to about 2 cP. In one embodiment, the 0.75% (w/v) solution has a viscosity at 37° C. of about 1.07 cP to about 1.08 cP. The gelatin solution may be provided in PBS, DMEM, or another suitable solvent.

In one aspect, the bioactive cell formulation also includes a cell viability agent. In one embodiment, the cell viability agent is selected from the group consisting of an antioxidant, an oxygen carrier, an immunomodulatory factor, a cell recruitment factor, a cell attachment factor, an anti-inflammatory agent, an angiogenic factor, a wound healing factor, and products secreted from bioactive cells.

Antioxidants are characterized by the ability to inhibit oxidation of other molecules. Antioxidants include, without limitation, one or more of 6-hydroxy-2,5,7,8-tetramethyl-chroman-2-carboxylic acid (Trolox®), carotenoids, flavonoids, isoflavones, ubiquinone, glutathione, lipoic acid, superoxide dismutase, ascorbic acid, vitamin E, vitamin A, mixed carotenoids (e.g., beta carotene, alpha carotene, gamma carotene, lutein, lycopene, phytopene, phytofluene, and astaxanthin), selenium, Coenzyme Q10, indole-3-carbinol, proanthocyanidins, resveratrol, quercetin, catechins, salicylic acid, curcumin, bilirubin, oxalic acid, phytic acid, lipoic acid, vanilic acid, polyphenols, ferulic acid, theaflavins, and derivatives thereof. Those of ordinary skill in the art will appreciate other suitable antioxidants for use in the present invention.

Oxygen carriers are agents characterized by the ability to carry and release oxygen. They include, without limitation, perfluorocarbons and pharmaceuticals containing perfluorocarbons. Suitable perfluorocarbon-based oxygen carriers include, without limitation, perfluorooctyl bromide (C8F17Br); perfluorodichorotane (C8F16C12); perfluorodecyl bromide; perfluobron; perfluorodecalin; perfluorotripopylamine; perfluoromethylcyclopiperidine; Fluosol® (perfluorodecalin & perfluorotripopylamine); Perftoran® (perfluorodecalin & perfluoromethylcyclopiperidine); Oxygent® (perfluorodecyl bromide & perfluobron); Ocycyte™ (perfluoro(tert-butylcyclohexane)). Those of ordinary skill in the art will appreciate other suitable perfluorocarbon-based oxygen carriers for use in the present invention.

Immunomodulatory factors include, without limitation, osteopontin, FAS Ligand factors, interleukins, transforming growth factor beta, platelet derived growth factor, clusterin, transferrin, regulated upon action, normal T-cell expressed, secreted protein (RANTES), plasminogen activator inhibitor-1 (Pai-1), tumor necrosis factor alpha (TNF-alpha), interleukin 6 (IL-6), alpha-1 microglobulin, and beta-2-microglobulin. Those of ordinary skill in the art will appreciate other suitable immunomodulatory factors for use in the present invention.

Anti-inflammatory agents or immunosuppressant agents (described below) may also be part of the formulation. Those of ordinary skill in the art will appreciate other suitable antioxidants for use in the present invention.

Cell recruitment factors include, without limitation, monocyte chemotatic protein 1 (MCP-1), and CXCL-1. Those of ordinary skill in the art will appreciate other suitable cell recruitment factors for use in the present invention.

Cell attachment factors include, without limitation, fibronectin, procollagen, collagen, ICAM-1, connective tissue growth factor, laminins, proteoglycans, specific cell adhesion peptides such as RGD and YSIGR. Those of ordinary skill in the art will appreciate other suitable cell attachment factors for use in the present invention.

Angiogenic factors include, without limitation, matrix metalloprotease 1 (MMP1), matrix metalloprotease 2 (MMP2), vascular endothelial growth factor F (VEGF), matrix metalloprotease 9 (MMP-9), tissue inhibitor or matalloproteases-1 (TIMP-1) vascular endothelial growth factor F (VEGF), angiopoietin-2 (ANG-2). Those of ordinary skill in the art will appreciate other suitable angiogenic factors for use in the present invention.

Wound healing factors include, without limitation, keratinocyte growth factor 1 (KGF-1), tissue plasminogen activator (tPA), calbindin, clusterin, cystatin C, trefoil factor 3. Those of ordinary skill in the art will appreciate other suitable wound healing factors for use in the present invention.

Secreted products from bioactive cells described herein may also be added to the bioactive cell formulation as a cell viability agent.

In one other aspect, the formulation includes a temperature-sensitive biomaterial described herein and a population of biocompatible beads containing a biomaterial. In one embodiment, the beads are crosslinked. Crosslinking may be achieved using any suitable crosslinking agent known to those of ordinary skill in the art, such as, for example, carbodiimides; aldehydes (e.g. furfural, acrolein, formaldehyde, glutaraldehyde, glyceryl aldehyde), succinimide-based crosslinkers {Bis(sulfosuccinimidyl) suberate (BS3), Disuccinimidyl glutarate (DSG), Disuccinimidyl suberate (DSS), Dithiobis(succinimidyl propionate), Ethylene glycolbis(sulfosuccinimidylsuccinate), Ethylene glycolbis(succinimidylsuccinate) (EGS), Bis(Sulfosuccinimidyl) glutarate (BS2G), Disuccinimidyl tartrate (DST)}; epoxides (Ethylene glycol diglycidyl ether, 1,4 Butanediol diglycidyl ether); saccharides (glucose and aldose sugars); sulfonic acids and p-toluene sulfonic acid; carbonyldiimidazole; genipin; imines; ketones; diphenylphosphorylazide (DDPA); terephthaloyl chloride; cerium (III) nitrate hexahydrate; microbial transglutaminase; and hydrogen peroxide. Those of ordinary skill in the art will appreciate other suitable crosslinking agents and crosslinking methods for use in the present invention.

In one embodiment, the beads are carbodiimide-crosslinked beads. The carbodiimide-crosslinked beads may be crosslinked with a carbodiimide selected from the group consisting of 1-Ethyl-3-[3-dimethylaminopropyl]carbodiimide hydrochloride (EDC), DCC—N,N'-dicyclohexylcarbodiimide (DCC), and N,N'-Diisopropylcarbodiimide (DIPC). Beads treated with lower concentration of EDC were expected to have a higher number of free primary amines, while samples treated with high concentrations of crosslinker would have most of the primary amines engaged in amide bonds. The intensity of the orange color developed by the covalent bonding between the primary amine and picrylsulfonic acid, detectable spectrophotometrically at 335 nm, is proportional to the number of primary amines present in the sample. When normalized per milligram of protein present in the sample, an inverse correlation between the number of free amines present and the initial concentration of EDC used for crosslinking can be observed. This result is indicative of differential bead crosslinking, dictated by the amount of carbodiimide used in the reaction. In general, crosslinked beads exhibit a reduced number of free primary amines as compared to non-crosslinked beads. The number of free primary amines may be detected spectrophotometrically at about 335 nm.

The crosslinked beads have a reduced susceptibility to enzymatic degradation as compared to non-crosslinked biocompatible beads, thereby providing beads with finely tunable in vivo residence times. For example, the cross-linked beads are resistant to endogenous enzymes, such as collagenases. The provision of crosslinked beads is part of a delivery system focused on the development and production of biomaterials that facilitate one or more of: (a) delivery of attached cells to the desired sites and creation of space for regeneration and ingrowth of native tissue and vascular supply; (b) ability to persist at the site long enough to allow cells to establish, function, remodel their microenvironment and secrete their own extracellular matrix (ECM); (c) promotion of integration of the transplanted cells with the surrounding tissue; (d) ability to implant cells in a substantially solid form; (e) short term structural integrity that does not provide a significant barrier to tissue ingrowth or integration of delivered cells/materials with the host tissue; (f) localized in vivo delivery in a substantially solid form thereby preventing dispersion of cells within the tissue during implantation; (g) improved stability and viability of anchorage dependent cells compared to cells suspended in a fluid; and (h) biphasic release profile when cells are delivered i) in a substantially solid form (e.g., attached to beads), and ii) in a substantially liquid form (e.g., suspended in a fluid).

Figure 10:
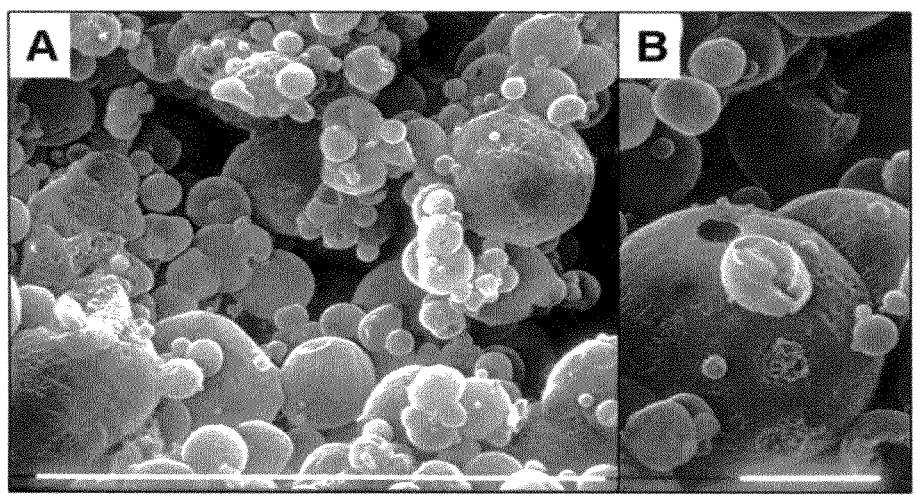
FIG. 10A-B. Morphology of gelatin beads. A—scanning electron microscopy image showing the overall morphology and size distribution of non-crosslinked gelatin beads (scale bar 1 mm). B—high magnification scanning electron microscopy image showing the porous, hollow structures of the beads (scale bar 100 µm).
Figure 15:
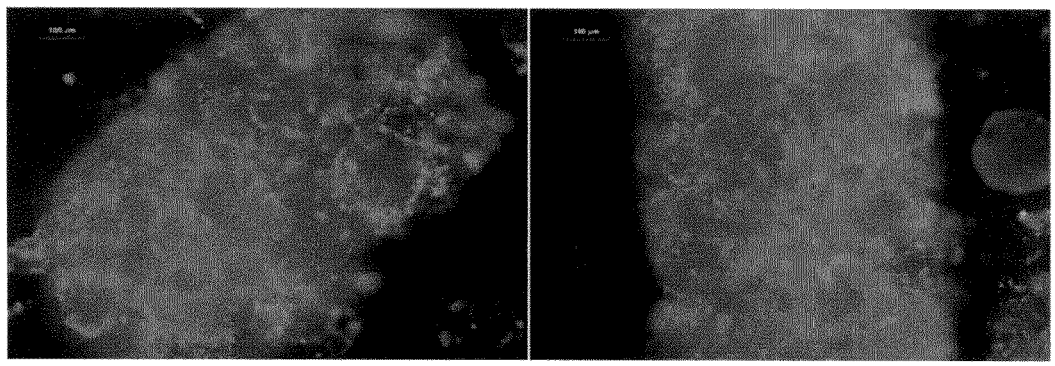
FIG. 15. Cytocompatibility of 10 mM EDC crosslinked beads showing cell attachment to the beads and cell viability (green=live; red=dead cells).

In one embodiment, the present invention provides cross-linked beads containing gelatin. Non-crosslinked gelatin beads are not suitable for a bioactive cell formulation because they rapidly lose integrity and cells dissipate from the injection site. In contrast, highly crosslinked gelatin beads may persist too long at the injection site and may hinder the de-novo ECM secretion, cell integration and tissue regeneration. The present invention allows for the in vivo residence time of the crosslinked beads to be finely tuned. In order to tailor the biodegradability of biomaterials, different crosslinker concentrations of carbodiimide are used while the overall reaction conditions were kept constant for all samples. For example, the enzymatic susceptibility of carbodiimide-crosslinked beads can be finely tuned by varying the concentration of crosslinking agent from about zero to about 1M. In some embodiments, the concentration is about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 46 mM, about 47 mM, about 48 mM, about 49 mM, about 50 mM, about 55 mM, about 60 mM, about 65 mM, about 70 mM, about 75 mM, about 80 mM, about 85 mM, about 90 mM, about 95 mM, or about 100 mM. The crosslinker concentration may also be about 0.15 M, about 0.2 M, about 0.25 M, about 0.3 M, about 0.35 M, about 0.4 M, about 0.45 M, about 0.5 M, about 0.55 M, about 0.6 M, about 0.65 M, about 0.7 M, about 0.75 M, about 0.8 M, about 0.85 M, about 0.9 M, about 0.95 M, or about 1 M. In another embodiment, the crosslinking agent is 1-Ethyl-3-[3-dimethylaminopropyl] carbodiimide hydrochloride (EDC). In one embodiment, the EDC-crosslinked beads are gelatin beads. FIG. 10 depicts a representative schematic for EDC-mediated crosslinking of gelatin beads and FIG. 15 illustrates how the % degradation of the beads can be finely tuned depending upon the concentration of crosslinking agent.

Cross-linked beads may have certain characteristics that favor the seeding, attachment, or encapsulation. For example, the beads may have a porous surface and/or may be substantially hollow. The presence of pores provides an increased cell attachment surface allowing for a greater number of cells to attach as compared to a non-porous or smooth surface. In addition, the pore structure can support host tissue integration with the porous beads supporting the formation of de novo tissue. The beads have a size distribution that can be fitted to a Weibull plot corresponding to the general particle distribution pattern. In one embodiment, the cross-linked beads have an average diameter of less than about 120 µm, about 115 µm, about 110 µm, about 109 µm, about 108 µm, about 107 µm, about 106 µm, about 105 µm, about 104 µm, about 103 µm, about 102 µm, about 101 µm, about 100 µm, about 99 µm, about 98 µm, about 97 µm, about 96 µm, about 95 µm, about 94 µm, about 93 µm, about 92 µm, about 91 µm, or about 90 µm. The characteristics of the cross-linked beads vary depending upon the casting process. For instance, a process in which a stream of air is used to aerosolize a liquid gelatin solution and spray it into liquid nitrogen with a thin layer chromatography reagent sprayer (ACE Glassware) is used to provide beads having the afore-mentioned characteristics. Those of skill in the art will appreciate that modulating the parameters of the casting process provides the opportunity to tailor different characteristics of the beads, e.g., different size distributions.

The cytocompatibility of the cross-linked beads is assessed in vitro prior to formulation using cell culture techniques in which beads are cultured with cells that correspond to the final bioactive cell formulation. For instance, the beads are cultured with primary renal cells prior to preparation of a bioactive renal cell formulation and live/dead cell assays are used to confirm cytocompatibility.

In certain formulations, the biocompatible cross-linked beads are combined with a temperature-sensitive biomaterial in solution at about 5% (w/w) to about 15% (w/w) of the volume of the solution. The cross-linked beads may be present at about 5% (w/w), about 5.5% (w/w), about 6% (w/w), about 6.5% (w/w), about 7% (w/w), about 7.5% (w/w), about 8% (w/w), about 8.5% (w/w), about 9% (w/w), about 9.5% (w/w), about 10% (w/w), about 10.5% (w/w), about 11% (w/w), about 11.5% (w/w), about 12% (w/w), about 12.5% (w/w), about 13% (w/w), about 13.5% (w/w), about 14% (w/w), about 14.5% (w/w), or about 15% (w/w) of the volume of the solution.

In another aspect, the present invention provides formulations that contain biomaterials which degrade over a period time on the order of minutes, hours, or days. This is in contrast to a large body or work focusing on the implantation of solid materials that then slowly degrade over days, weeks, or months.

In another aspect, the present invention provides formulations having biocompatible cross-linked beads seeded with bioactive cells together with a delivery matrix. In one embodiment, the delivery matrix has one or more of the following characteristics: biocompatibility, biodegradeable/bioresorbable, a substantially solid state prior to and during implantation into a subject, loss of structural integrity (substantially solid state) after implantation, and cytocompatible environment to support cellular viability. The delivery matrix's ability to keep implanted particles (e.g., crosslinked beads) spaced out during implantation enhances native tissue ingrowth. If the delivery matrix is absent, then compaction of cellularized beads during implantation can lead to inadequate room for sufficient tissue ingrowth. The delivery matrix facilitates implantation of solid formulations. In addition, the short duration of the structural integrity means that soon after implantation, the matrix does not provide a significant barrier to tissue ingrowth or integration of the delivered cells/materials with host tissue. The delivery matrix provides for localization of the formulation described herein since inserted of a solid unit helps prevent the delivered materials from dispersing within the tissue during implantation. For cell-based formulations, a solid delivery matrix improves stability and viability of anchorage dependent cells compared to cells suspended in a fluid.

In one embodiment, the delivery matrix is a population of biocompatible beads that is not seeded with cells. In another embodiment, the unseeded beads are dispersed throughout and in between the individual cell-seeded beads. The unseeded beads act as "spacer beads" between the cell-seeded beads prior to and immediately after transplantation. The spacer beads contain a temperature-sensitive biomaterial having a substantially solid state at a first temperature and a substantially liquid state at a second temperature, wherein the first temperature is lower than the second temperature. For example, the spacer beads contain a biomaterial having a substantially solid state at about ambient temperature or below and a substantially liquid state at about 37° C., such as that described herein. In one embodiment, the ambient temperature is about room temperature. In another embodiment, the biomaterial is a gelatin solution. The gelatin solution is present at about 4%, about 4.5%, about 5%, about 5.5%, about 6%, about 6.5%, about 7%, about 7.5%, about 8%, about 8.5%, about 9%, about 9.5%, about 10%, about 10.5%, or about 11%, (w/v). The gelatin solution may be provided in PBS, cell culture media (e.g., DMEM), or another suitable solvent.

In one aspect, the present invention provides formulations that contain biomaterials which are implanted in a substantially solid form (e.g., spacer beads) and then liquefy/melt or otherwise lose structural integrity following implantation into the body. This is in contrast to the significant body of work focusing on the use of materials that can be injected as a liquid, which then solidify in the body.

Figure 2:
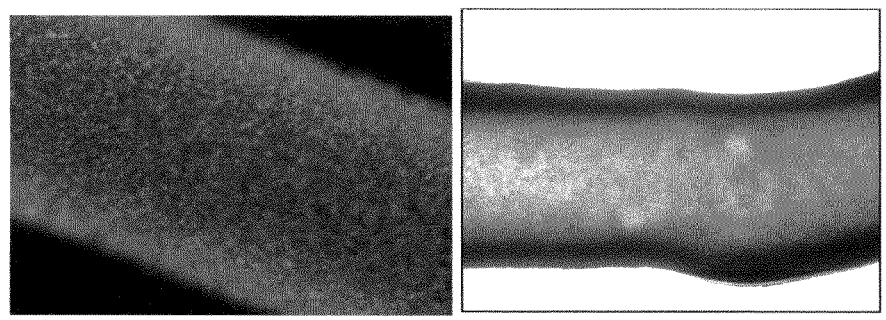
FIG. 2. Matrix containing individual kidney cells suspended.

The temperature-sensitivity of spacer beads can be assessed in vitro prior to formulation. Spacer beads can be labeled and mixed with unlabeled non-temperature-sensitive beads. The mixture is then incubated at 37° C. to observe changes in physical transition. The loss of shape of the labeled temperature-sensitive beads at the higher temperature is observed over time. For example, temperature-sensitive gelatin beads may be made with Alcian blue dye to serve as a marker of physical transition. The blue gelatin beads are mixed with Cultispher S beads (white), loaded into a catheter, then extruded and incubated in 1×PBS, pH 7.4, at 37° C. The loss of shape of the blue gelatin beads is followed microscopically at different time points. Changes in the physical state of the blue gelatin beads are visible after 30 min becoming more pronounced with prolonged incubation times. The beads do not completely dissipate because of the viscosity of the material. (FIG. 2).

The bioactive cell formulations described herein may be used to prepare renal cell-based formulations for injection into the kidney. However, those of ordinary skill in the art will appreciate that the formulations will be suitable for many other types of bioactive cell populations. For example, the present invention contemplates formulations for bioactive cells for injection into any solid organ or tissue.

In one aspect, the bioactive cell formulations described herein will contain a set number of cells. In one embodiment, the total number of cells for the formulation is about $10^4$, about $10^5$, about $10^6$, about $10^7$, about $10^8$, or about $10^9$. In one embodiment, the dosage of cells for a formulation described herein may be calculated based on the estimated mass or functional mass of the target organ or tissue. In certain embodiments, the bioactive cell formulations of the present invention contain a dosage corresponding to a number of cells based upon the weight of the host organ that will be the subject of treatment by the formulation. For example, a bioactive renal cell formulation is based upon an average weight of about 150 grams for a human kidney. In one embodiment, the number of cells per gram (g) of kidney is about 600 cells/g to about $7.0 \times 10^7$ cells/g. In some embodiments, the number of cells per gram of kidney is about 600 cells/g, about 1000 cells/g, about 1500 cells/g, about 2000 cells/g, about 2500 cells/g, about 3000 cells/g, about 3500 cells/g, about 4000 cells/g, about 4500 cells/g, about 5000 cells/g, about 5500 cells/g, about 6000 cells/g, about 6500 cells/g, about 7000 cells/g, about 7500 cells/g, about 8000 cells/g, about 8500 cells/g, about 9000 cells/g, about 9500 cells/g, or about 10,000 cells/g.

In other embodiments, the number of cells per gram of kidney is about $1.5 \times 10^4$ cells/g, about $2.0 \times 10^4$ cells/g, about $2.5 \times 10^4$ cells/g, about $3.0 \times 10^4$ cells/g, about $3.5 \times 10^4$ cells/g, about $4.0 \times 10^4$ cells/g, about $4.5 \times 10^4$ cells/g, about $5.0 \times 10^4$ cells/g, about $5.5 \times 10^4$ cells/g, about $6.0 \times 10^4$ cells/g, about $6.5 \times 10^4$ cells/g, about $7.0 \times 10^4$ cells/g, about $7.5 \times 10^4$ cells/g, about $8.0 \times 10^4$ cells/g, about $9.5 \times 10^4$ cells/g.

In other embodiments, the number of cells per gram of kidney is about $1.0 \times 10^5$ cells/g, about $1.5 \times 10^5$ cells/g, about $2.0 \times 10^5$ cells/g, about $2.5 \times 10^5$ cells/g, about $3.0 \times 10^5$ cells/g, about $3.5 \times 10^5$ cells/g, about $4.0 \times 10^5$ cells/g, about $4.5 \times 10^5$ cells/g, about $5.0 \times 10^5$ cells/g, about $5.5 \times 10^5$ cells/g, about $6.0 \times 10^5$ cells/g, about $6.5 \times 10^5$ cells/g, about $7.0 \times 10^5$ cells/g, about $7.5 \times 10^5$ cells/g, about $8.0 \times 10^5$ cells/g, about $8.5 \times 10^5$ cells/g, about $9.0 \times 10^5$ cells/g, or about $9.5 \times 10^5$ cells/g.

In other embodiments, the number of cells per gram of kidney is about $1.0 \times 10^6$ cells/g, about $1.5 \times 10^6$ cells/g, about $2.0 \times 10^6$ cells/g, about $2.5 \times 10^6$ cells/g, about $3.0 \times 10^6$ cells/g, about $3.5 \times 10^6$ cells/g, about $4.0 \times 10^6$ cells/g, about $4.5 \times 10^6$ cells/g, about $5.0 \times 10^6$ cells/g, about $5.5 \times 10^6$ cells/g, about $6.0 \times 10^6$ cells/g, about $6.5 \times 10^6$ cells/g, about $7.0 \times 10^6$ cells/g, about $7.5 \times 10^6$ cells/g, about $8.0 \times 10^6$ cells/g, about $8.5 \times 10^6$ cells/g, about $9.0 \times 10^6$ cells/g, about $9.5 \times 10^6$ cells/g, $1.0 \times 10^7$ cells/g, or about $1.5 \times 10^7$ cells/g.

A total number of cells may be selected for the formulation and the volume of the formulation may be adjusted to reach the proper dosage.

In some embodiments, the formulation may contain a dosage of cells to a subject that is a single dosage or a single dosage plus additional dosages. In other embodiments, the dosages may be provided by way of a construct as described herein. The therapeutically effective amount of the renal cell populations or admixtures of renal cell populations described herein can range from the maximum number of cells that is safely received by the subject to the minimum number of cells necessary for treatment of kidney disease, e.g., stabilization, reduced rate-of-decline, or improvement of one or more kidney functions.

The therapeutically effective amount of the renal cell populations or admixtures thereof described herein can be suspended in a pharmaceutically acceptable carrier or excipient. Such a carrier includes, but is not limited to basal culture medium plus 1% serum albumin, saline, buffered saline, dextrose, water, collagen, alginate, hyaluronic acid, fibrin glue, polyethyleneglycol, polyvinylalcohol, carboxymethylcellulose and combinations thereof. The formulation should suit the mode of administration.

Accordingly, the invention provides a use of a formulation containing renal cell populations or admixtures thereof, for example, the B2 cell population alone or admixed with the B3 and/or B4 or B4' cell population, for the manufacture of a medicament to treat kidney disease in a subject. In some embodiments, the medicament further comprises recombinant polypeptides, such as growth factors, chemokines or cytokines. In further embodiments, the medicaments comprise a human kidney-derived cell population. The cells used to manufacture the medicaments can be isolated, derived, or enriched using any of the variations provided for the methods described herein.

The renal cell preparation(s), or admixtures thereof, or compositions are formulated in accordance with routine procedures as a pharmaceutical composition adapted for administration to human beings. Typically, compositions for intravenous administration, intra-arterial administration or administration within the kidney capsule, for example, are solutions in sterile isotonic aqueous buffer. Where necessary, the composition can also include a local anesthetic to ameliorate any pain at the site of the injection. Generally, the ingredients are supplied either separately or mixed together in unit dosage form, for example, as a cryopreserved concentrate in a hermetically sealed container such as an ampoule indicating the quantity of active agent. When the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

Pharmaceutically acceptable carriers are determined in part by the particular composition being administered, as well as by the particular method used to administer the composition. Accordingly, there are a wide variety of suitable formulations of pharmaceutical compositions (see, e.g., Alfonso R Gennaro (ed), Remington: The Science and Practice of Pharmacy, formerly Remington's Pharmaceutical Sciences 20th ed., Lippincott, Williams & Wilkins, 2003, incorporated herein by reference in its entirety). The pharmaceutical compositions are generally formulated as sterile, substantially isotonic and in full compliance with all Good Manufacturing Practice (GMP) regulations of the U.S. Food and Drug Administration.

One aspect of the invention further provides a pharmaceutical formulation, comprising a renal cell preparation of the invention, for example, the B2 cell preparation alone or incombination with the B3 and/or B4 or B4' cell preparation, and a pharmaceutically acceptable carrier. In some embodiments, the formulation comprises from $10^4$ to $10^9$ mammalian kidney-derived cells.

Modified Release Formulations

In one aspect, the formulations of the present invention are provided as modified release formulations. In general, the modified release is characterized by an initial release of a first active agent upon administration following by at least one additional, subsequent release of a second active agent. The first and second active agents may be the same or they may be different. In one embodiment, the formulations provide modified release through multiple components in the same formulation. In another embodiment, the modified release formulation contains an active agent as part of a first component that allows the active agent to move freely throughout the volume of the formulation, thereby permitting immediate release at the target site upon administration. The first component may be a temperature-sensitive biomaterial having a substantially liquid phase and a substantially solid phase, wherein the first component is in a substantially liquid phase at the time of administration. In one embodiment, the active agent in the substantially liquid phase such that it is substantially free to move throughout the volume of the formulation, and therefore is immediately released to the target site upon administration.

In another embodiment, the modified release formulation has an active agent as part of a second component in which the active agent is attached to, deposited on, coated with, embedded in, seeded upon, or entrapped in the second component, which persists before and after administration to the target site. The second component contains structural elements with which the active agent is able to associate with, thereby preventing immediate release of the active agent from the second component at the time of administration. For example, the second component is provided in a substantially solid form, e.g., biocompatible beads, which may be crosslinked to prevent or delay in vivo enzymatic degradation. In one embodiment, the active agent in the substantially solid phase retains its structural integrity within the formulation before and after administration and therefore it does not immediately release the active agent to the target site upon administration. Suitable carriers for modified release formulations have been described herein but those of ordinary skill in the art will appreciate other carriers that are appropriate for use in the present invention.

In one embodiment, the formulation provides an initial rapid delivery/release of delivered elements, including cells, nanoparticles, therapeutic molecules, etc. followed by a later delayed release of elements. The formulations of the present invention can be designed for such biphasic release profile where the agent to be delivered is provided in both an unattached form (e.g., cells in a solution) and an attached form (e.g., cells together with beads or another suitable carrier). Upon initial administration, the unencumbered agent is provided immediately to the site of delivery while release of the encumbered agent is delayed until structural integrity of the carrier (e.g., beads) fails at which point the previously attached agent is released. As discussed below, other suitable mechanisms of release will be appreciated by those of ordinary skill in the art.

The time delay for release can be adjusted based upon the nature of the active agent. For example, the time delay for release in a bioactive cell formulation may be on the order of seconds, minutes, hours, or days. In some circumstances, a delay on the order of weeks may be appropriate. For other active agents, such as small or large molecules, the time delay for release in a formulation may be on the order of seconds, minutes, hours, days, weeks, or months. It is also possible for the formulation to contain different biomaterials that provide different time delay release profiles. For example, a first biomaterial with a first active agent may have a first release time and a second biomaterial with a second active agent may have a second release time. The first and second active agent may be the same or different.

As discussed herein, the time period of delayed release may generally correspond to the time period for loss of structural integrity of a biomaterial. However, those of ordinary skill in the art will appreciate other mechanisms of delayed release. For example, an active agent may be continually released over time independent of the degradation time of any particular biomaterial, e.g., diffusion of a drug from a polymeric matrix. In addition, bioactive cells can migrate away from a formulation containing a biomaterial and the bioactive cells to native tissue. In one embodiment, bioactive cells migrate off of a biomaterial, e.g., a bead, to the native tissue.

Biodegradable, biocompatible polymers can be used, such as ethylene vinyl acetate, polyanhydrides, polyglycolic acid, collagen, polyorthoesters, and polylactic acid. Prolonged absorption of injectable formulations can be brought about by including in the formulation an agent that delays absorption, for example, monostearate salts and gelatin. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978. Additional methods applicable to the controlled or extended release of polypeptide agents are described, for example, in U.S. Pat. Nos. 6,306,406 and 6,346,274, as well as, for example, in U.S. Patent Application Nos. US20020182254 and US20020051808, all of which are incorporated herein by reference.

9. Methods and Routes of Administration

The bioactive cell formulations of the present invention can be administered alone or in combination with other bioactive components. The formulations are suitable for injection or implantation of incorporated tissue engineering elements to the interior of solid organs to regenerate tissue. In addition, the formulations are used for the injection or implantation of tissue engineering elements to the wall of hollow organs to regenerate tissue.

In one aspect, the present invention provides methods of providing a bioactive cell formulation described herein to a subject in need. In one embodiment, the source of the bioactive cell may be autologous or allogeneic, syngeneic (autogeneic or isogeneic), and any combination thereof. In instances where the source is not autologous, the methods may include the administration of an immunosuppressant agent. Suitable immunosuppressant drugs include, without limitation, azathioprine, cyclophosphamide, mizoribine, ciclosporin, tacrolimus hydrate, chlorambucil, lobenzarit disodium, auranofin, alprostadil, gusperimus hydrochloride, biosynsorb, muromonab, alefacept, pentostatin, dacliximab, sirolimus, mycophenolate mofetil, leflonomide, basiliximab, dornase a, bindarid, cladribine, pimecrolimus, ilodecakin, cedelizumab, efalizumab, everolimus, anisperimus, gavilimomab, faralimomab, clofarabine, rapamycin, siplizumab, saireito, LDP-03, CD4, SR-43551, SK&F-106615, IDEC-114, IDEC-131, FTY-720, TSK-204, LF-080299, A-86281, A-802715, GVH-313, HMR-1279, ZD-7349, IPL-423323, CBP-1011, MT-1345, CNI-1493, CBP-2011, J-695, LIP-920, L-732531, ABX-RB2, AP-1903, IDPS, BMS-205820, BMS-224818, CTLA4-1g, ER-49890, ER-38925, ISAtx-247, RDP-58, PNU-156804, LJP-1082, TMC-95A, TV-4710, PTR-262-MG, and AGI-1096 (see U.S. Pat. No. 7,563,822). Those of ordinary skill in the art will appreciate other suitable immunosuppressant drugs.

The treatment methods of the subject invention involve the delivery of a bioactive cell formulation described herein. In one embodiment, direct administration of cells to the site of intended benefit is preferred. A subject in need may also be treated by in vivo contacting of a native kidney with a bioactive cell formulation described herein together with products secreted from one or more enriched renal cell populations, and/or an admixture or construct containing the same.

The step of contacting a native kidney in vivo with secreted products may be accomplished through the use/administration of a formulation containing a population of secreted products from cell culture media, e.g., conditioned media, or by implantation of an enriched cell population, and admixture, or a construct capable of secreting the products in vivo. The step of in vivo contacting provides a regenerative effect to the native kidney.

A variety of means for administering cells and/or secreted products to subjects will, in view of this specification, be apparent to those of skill in the art. Such methods include injection of the cells into a target site in a subject.

Cells and/or secreted products can be inserted into a delivery device or vehicle, which facilitates introduction by injection or implantation into the subjects. In certain embodiments, the delivery vehicle can include natural materials. In certain other embodiments, the delivery vehicle can include synthetic materials. In one embodiment, the delivery vehicle provides a structure to mimic or appropriately fit into the organ's architecture. In other embodiments, the delivery vehicle is fluid-like in nature. Such delivery devices can include tubes, e.g., catheters, for injecting cells and fluids into the body of a recipient subject. In a preferred embodiment, the tubes additionally have a needle, e.g., a syringe, through which the cells of the invention can be introduced into the subject at a desired location. In some embodiments, mammalian kidney-derived cell populations are formulated for administration into a blood vessel via a catheter (where the term "catheter" is intended to include any of the various tube-like systems for delivery of substances to a blood vessel). Alternatively, the cells can be inserted into or onto a biomaterial or scaffold, including but not limited to textiles, such as weaves, knits, braids, meshes, and non-wovens, perforated films, sponges and foams, and beads, such as solid or porous beads, microparticles, nanoparticles, and the like (e.g., Cultispher-S gelatin beads—Sigma). The cells can be prepared for delivery in a variety of different forms. For example, the cells can be suspended in a solution or gel. Cells can be mixed with a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid, and will often be isotonic. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. One of skill in the art will appreciate that the delivery vehicle used in the delivery of the cell populations and admixtures thereof of the instant invention can include combinations of the above-mentioned characteristics.

Modes of administration of the formulations containing isolated renal cell population(s), for example, the B2 cell population alone or admixed with B4' and/or B3, include, but are not limited to, systemic, intra-renal (e.g., parenchymal), intravenous or intra-arterial injection and injection directly into the tissue at the intended site of activity. Additional modes of administration to be used in accordance with the present invention include single or multiple injection(s) via direct laparotomy, via direct laparoscopy, transabdominal, or percutaneous. Still yet additional modes of administration to be used in accordance with the present invention include, for example, retrograde and ureteropelvic infusion. Surgical means of administration include one-step procedures such as, but not limited to, partial nephrectomy and construct implantation, partial nephrectomy, partial pyelectomy, vascularization with omentum±peritoneum, multifocal biopsy needle tracks, cone or pyramidal, to cylinder, and renal pole-like replacement, as well as two-step procedures including, for example, organoid-internal bioreactor for replanting. In one embodiment, the formulations containing admixtures of cells are delivered via the same route at the same time. In another embodiment, each of the cell compositions comprising the controlled admixture are delivered separately to specific locations or via specific methodologies, either simultaneously or in a temporally-controlled manner, by one or more of the methods described herein.

The appropriate cell implantation dosage in humans can be determined from existing information relating to either the activity of the cells, for example EPO production, or extrapolated from dosing studies conducted in preclinical studies. From in vitro culture and in vivo animal experiments, the amount of cells can be quantified and used in calculating an appropriate dosage of implanted material. Additionally, the patient can be monitored to determine if additional implantation can be made or implanted material reduced accordingly.

One or more other components can be added to the cell populations and admixtures thereof of the instant invention, including selected extracellular matrix components, such as one or more types of collagen or hyaluronic acid known in the art, and/or growth factors, platelet-rich plasma and drugs.

Those of ordinary skill in the art will appreciate the various formulations and methods of administration suitable for the secreted products described herein.

10. Articles of Manufacture and Kits

The instant invention further includes kits comprising the polymeric matrices and scaffolds of the invention and related materials, and/or cell culture media and instructions for use. The instructions for use may contain, for example, instructions for culture of the cells or administration of the cells and/or cell products. In one embodiment, the present invention provides a kit comprising a scaffold as described herein and instructions. In yet another embodiment, the kit includes an agent for detection of marker expression, reagents for use of the agent, and instructions for use. This kit may be used for the purpose of determining the regenerative prognosis of a native kidney in a subject following the implantation or administration of a cell population, an admixture, or a construct described herein. The kit may also be used to determine the biotherapeutic efficacy of a cell population, admixture, or construct described herein.

Another embodiment of the invention is an article of manufacture containing bioactive cells useful for treatment of subjects in need. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating a condition and may have a sterile access port (for example the container may be a solution bag or a vial having a stopper pierceable by an injection needle). At least one active agent in the formulation is a bioactive cell population of the invention. The label or package insert indicates that the formulation is used for treating the particular condition. The label or package insert will further comprise instructions for administering the formulation to the patient. Articles of manufacture and kits comprising combinatorial therapies described herein are also contemplated. Package insert refers to instructions customarily included in commercial packages of therapeutic products that contain information about the indications, usage, dosage, administration, contraindications and/or warnings concerning the use of such therapeutic products. In one embodiment, the package insert indicates that the formulation is used for treating a disease or disorder, such as, for example, a kidney disease or disorder. It may further include other materials desirable from a commercial and user standpoint, including other buffers, diluents, filters, needles, and syringes. Kits are also provided that are useful for various purposes, e.g., for assessment of regenerative outcome. Kits can be provided which contain detection agents for urine-derived vesicles and/or their contents, e.g., nucleic acids (such as miRNA), vesicles, exosomes, etc., as described herein. Detection agents include, without limitation, nucleic acid primers and probes, as well as antibodies for in vitro detection of the desired target. As with the article of manufacture, the kit comprises a container and a label or package insert on or associated with the container. The container holds a composition comprising at least one detection agent. Additional containers may be included that contain, e.g., diluents and buffers or control detection agents. The label or package insert may provide a description of the composition as well as instructions for the intended in vitro, prognostic, or diagnostic use.

11. Reports

The methods of this invention, when practiced for commercial purposes generally produce a report or summary of the regenerative prognosis. The methods of this invention will produce a report comprising a prediction of the probable course or outcome of regeneration before and after any administration or implantation of a formulation containing a cell population, an admixture, or a construct described herein. The report may include information on any indicator pertinent to the prognosis. The methods and reports of this invention can further include storing the report in a database. Alternatively, the method can further create a record in a database for the subject and populate the record with data. In one embodiment the report is a paper report, in another embodiment the report is an auditory report, in another embodiment the report is an electronic record. It is contemplated that the report is provided to a physician and/or the patient. The receiving of the report can further include establishing a network connection to a server computer that includes the data and report and requesting the data and report from the server computer. The methods provided by the present invention may also be automated in whole or in part.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. Thus, for an embodiment of the invention using one of the terms, the invention also includes another embodiment wherein one of these terms is replaced with another of these terms. In each embodiment, the terms have their established meaning. Thus, for example, one embodiment may encompass a formulation "comprising" a number of components, another embodiment would encompass a formulation "consisting essentially of" the same components, and a third embodiment would encompass a formulation "consisting of" the same components. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The foregoing written description is considered to be sufficient to enable one skilled in the art to practice the invention. The following Examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

All patents, patent applications, and literature references cited in the present specification are hereby incorporated by reference in their entirety.

EXAMPLES

Example 1: Use of a Delivery Matrix with Short Term Structural Integrity

In the process of investigating novel biomaterial/cell systems and assessing their performance in our rodent injection models, we designed and developed a method for producing thermally reversible beads based on gelatin, as well as a thermally reversible gelatin continuous phase Delivery Matrix that would create a biomimetic microenvironment around cellularized beads, cell aggregates or single cell suspension, permissive for cell-induced extracellular matrix remodeling, cell-cell interaction, cell migration, proliferation and tissue regeneration. We have specifically demonstrated the utility of the Delivery Matrix technology in the form of gelatin solutions that are solid at and below room temperature and liquid at body temperature. This thermally reversible injectable matrix has been used to implant free cells, cell aggregates, cells on microcarrier beads, and a mixture of free cells with cells on microcarriers into the parenchyma of rat kidneys.

Methods

Bead Fabrication.

A 10% w/v gelatin solution (Gelita, Inc., Sioux City, Iowa) was prepared in deionized water and then air sprayed into liquid nitrogen (LN2) with a thin layer chromatography reagent sprayer. LN2 was allowed to evaporate in a chemical fume hood and beads were collected.

Cytocompatibility and In Vivo Implantation Evaluation of Biomaterials.

The Live/Dead® mammalian cell viability/cytotoxicity kit (Invitrogen, Carlsbad, Calif.) was used in conjunction with fluorescent micrograph imaging to assess cytocompatibility. Histological analysis of kidney injected with spacer beads mixed with Cultispher S beads (1 week post implantation) was carried out to assess the biocompatibility of the beads and their space creating capacity. The histology slides were stained with either Masson's Trichrome (which stains collagen blue) or hematoxylin & eosin (H&E). The images were evaluated for both positive indicators (tissue ingrowth, minimal to no detectable biomaterial at 1 month and healthy tissue) & negative indicators (presence of macrophages, giant cells, and other inflammatory cells; biomaterial persistence that supports a fibrotic capsule formation and an increase in the size of collecting ducts).

Results

Thermally Reversible Beads

Beads were produced from a porcine gelatin solution at a concentration that allowed the material to gel/solidify at temperatures below 25° C. and liquefy above 30° C. Temperature responsiveness of uncrosslinked gelatin beads (blue) was observed. Alcian Blue dye was included in the initial gelatin solution to serve as a marker of physical transition. Blue gelatin beads were then mixed in with commercially available microcarrier beads (white), loaded into a catheter, then extruded and incubated in 1×PBS, pH 7.4, at 37° C. The loss of shape of the blue gelatin beads was followed microscopically at different time points. Changes in the physical state of the blue gelatin beads were visible after 30 min and became more pronounced with prolonged incubation times. The beads did not completely dissipate because of the viscosity of the material (FIG. 1).

Thermally Reversible Delivery Matrix

Figure 5:
FIG. 5. Matrix containing cells plus a soluble factor (hyaluronic acid).
Figure 6:
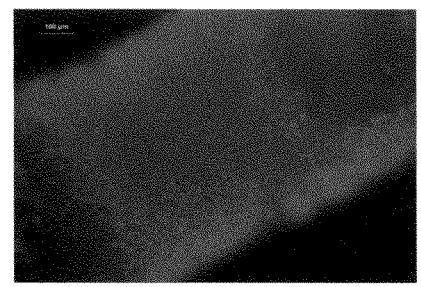
FIG. 6. Cell viability after 3 days at 4° C. in matrix.
Figure 7:
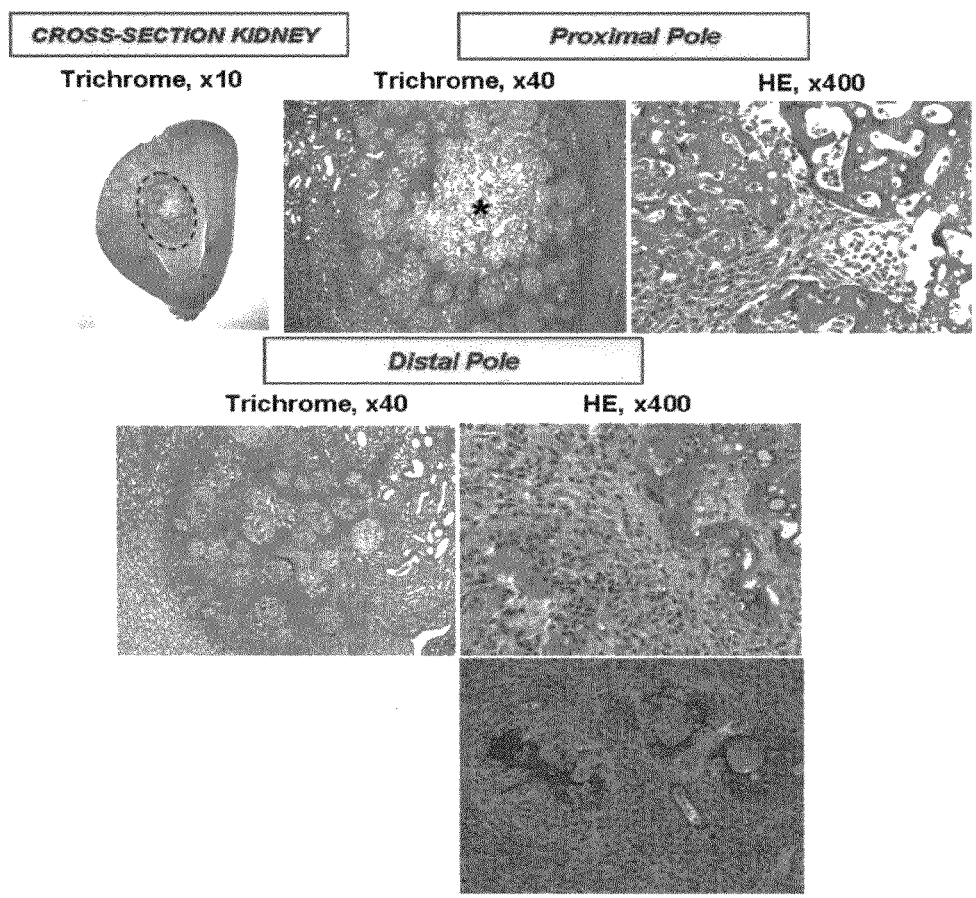
FIG. 7. Histology of kidney injected with spacer beads mixed with Cultispher S beads (1 week) illustrating the biocompatibility of the beads and their space creating capacity.

The thermally reversible injectable matrix was combined with the elements to be delivered in a fluid state, placed into a tubular catheter, and cooled below room temperature to gel the matrix. In the fluorescent micrograph images, a Live/Dead® mammalian cell viability/cytotoxicity kit (Invitrogen, Carlsbad, Calif.) stain was used that demonstrated live cells staining green and dead cells staining red (FIGS. 2-6). We find the cells embedded in thermally reversible injectable matrix remain viable after cooling to gel the matrix. Histological analyses of tissues where matrix containing microcarrier beads were implanted (1 week post implantation) revealed the microcarrier beads as dark purple structures. The matrix material was not visible on this slide, and there was no evidence that it was a barrier to tissue ingrowth (FIG. 7).

Figure 8:
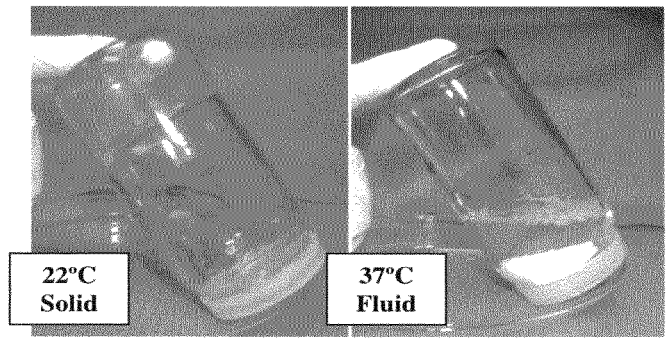
FIG. 8. Illustration of the loss of structural integrity of matrix (left panel: solid; right panel: fluid).

Illustration of the loss of structural integrity of matrix is depicted in FIG. 8. The matrix does not flow at room temperature, but flows at 37° C. The observed characteristics and features of the matrix material will allow for the delivery of incorporated elements in numerous tissue engineering and regenerative medicine applications. Specifically, the invention harnesses the benefits of both 1) the structural integrity before and during implantation, as well as 2) the loss of structure at some point shortly after implantation, to deliver the material to a target location in a tissue or organ with controlled handling, placement or dispersion without being a hindrance or barrier to the interaction of the incorporated elements with the tissue or organ into which it was placed.

Figure 9:
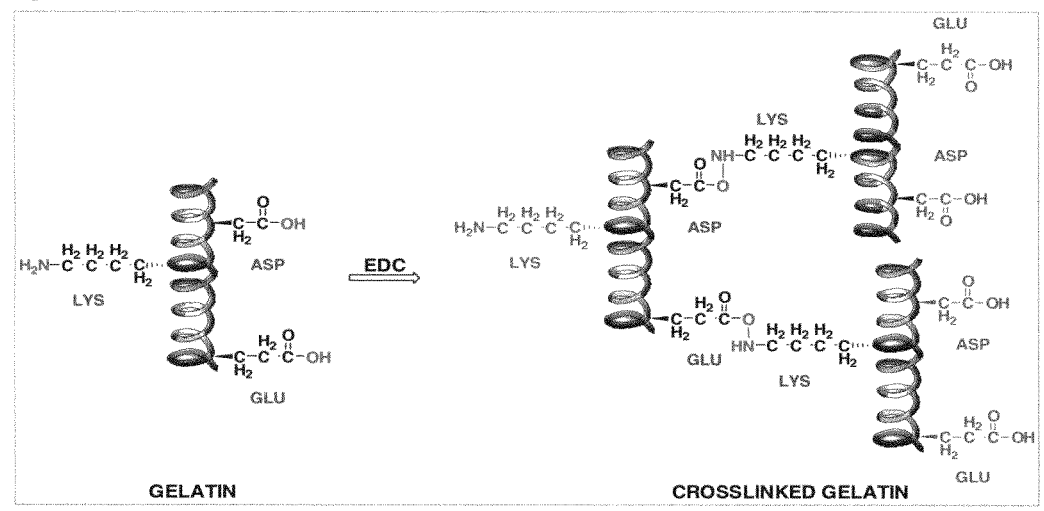
FIG. 9. Synthetic scheme for carbodiimide-mediated gelatin crosslinking indicating the amino acid residues involved in the reaction (in the non-crosslinked gelatin) and the amide bond they form (in the crosslinked gelatin).

Example 2: Tailoring the Enzymatic Susceptibility of Biomaterials Through Chemical Crosslinking To tailor the enzymatic susceptibility of the biomaterials to endogenous collagenases, the production of thermally reversible beads based on porcine gelatin (as described above in Example 1) can be further chemically crosslinked to different extents in order to modulate their in vivo residence times. This also allows the material to act as a spacer between discrete tissue regenerative constructs (such as cells seeded on carrier beads), facilitating tissue ingrowth and creating a biomimetic niche. In addition, this material has the potential to serve as cell, drug or other molecule delivery systems. For this, we chose to use a well characterized and widely used reagent, N-(3-Dimethylaminopropyl)-N'-ethylcarbodiimide hydrochloride (EDC). This zero-length crosslinker promotes the formation of an amide bond between spatially adjacent carboxyl and primary amine functionalities located either intra- or intermolecularly (FIG. 9).

Methods

Materials.

Low endotoxin gelatin was purchased from Gelita, Inc., Sioux City, Iowa. Picrylsulfonic acid solution (TNBS) and N-Ethyl-N'-(3-dimethylaminopropyl) carbodiimide hydrochloride (EDC) were from Sigma-Aldrich, St. Louis, Mo. The LIVE/DEAD® mammalian cell viability/cytotoxicity kit was from Invitrogen, Carlsbad, Calif. Sodium hydroxide (NaOH), calcium chloride ($CaCl_2$) and 2-[morpholino]ethanesulfonic acid, 0.9% NaCl, pH 4.7 (MES) buffer were from Fisher Scientific, Pittsburgh, Pa. Collagenase IV was from Worthington Biochemical Corp., Lakewood, N.J. and dispase I (4 U/ml) was from Stemcell Technologies, Vancouver, BC. Dulbecco's Modified Eagle Medium (DMEM), Keratinocyte-Serum Free Medium (Keratinocyte-SFM) and phosphate buffered saline (PBS) were from Invitrogen/Gibco, Carlsbad, Calif.

Chemical Crosslinking.

Lyophilized gelatin beads were suspended in 0.1M MES buffer, pH 4.7 (Thermo Fisher Scientific, Rockford, Ill.) (20 ml buffer/gram of beads) and rehydrated for 1-3 hours, preferably at 4° C. The buffer (chosen based on the pH and buffering requirements of the chemical reaction) was then removed and a 1:1 (v/v) suspension made with EDC (1-Ethyl-3-[3-dimethylaminopropyl]carbodiimide hydrochloride)/MES pH 7.4 solution equal to the volume of beads, where EDC concentrations ranged from 10-100 mM, and after brief vortexing the suspension was incubated overnight at room temperature under static conditions. Subsequently, beads were filtered and washed with deionized water (wash volume=20× bead volume), then frozen and lyophilized.

In Vitro Enzymatic Degradation Assay.

Degradation rates for beads crosslinked with varying concentrations of EDC were assayed by their susceptibility to collagenase/dispase digestion and compared to commercially available CULTISPHER® beads. CULTISPHER® and Crosslinked beads were weighed out and suspended in PBS, pH 7.4 to a concentration of ~20 mg/ml. To a volume of 0.5 ml bead suspension 50 µl of 30 U/ml collagenase/dispase mix (Thermo Fisher Scientific) with 0.5 mM $CaCl_2$ was added, then samples were vortexed and incubated for 1 h at 37° C. on a rocker (n=3 for each crosslinker concentration used). Subsequently, 20 µl supernatant from the partially digested samples were collected and evaluated for soluble protein content using a modified Bradford assay in which the ratio of the dye to protein solution was set to 1:9 v/v in order to increase its sensitivity. The remaining digestion mix was incubated overnight as described above, and assayed similarly for total protein content determination. These values were used to normalize the partially digested sample values. The amounts of total protein in the samples were calculated from a gelatin standard curve obtained by plotting the $A_{595}$ values for solutions made from known amounts of gelatin that were fully digested then assayed with Bradford reagent. The amounts of total protein in the samples were considered to be 100% and the protein amounts obtained by partial digestion were normalized relative to 100%. Degradation was calculated as the ratio of soluble protein at 1 hr/total soluble protein as measured by a Bradford assay.

Amine Quantification.

The pH of fully digested crosslinked beads solutions (obtained as described above) (n=3) was raised by adding 5 µl of 1M NaOH to each vial (final pH value was ~8.5). Subsequently, TNBS was added to each sample to a final concentration of 0.25% w/v and vials were incubated at 37° C. for 2 hours on a rocker. The $A_{335}$ values were then determined with a plate reader and values were normalized per milligram protein in each sample as determined previously (described above). The amounts of total protein in the samples were calculated from a gelatin standard curve obtained by plotting the $A_{595}$ values for solutions made from known amounts of gelatin that were fully digested then assayed with Bradford reagent.

Bead Sizing.

To narrow the size distribution, crosslinked beads are suspended in 70% v/v ethanol and sized to 64-250 µm by sequential filtering through nylon meshes of defined pore sizes.

Morphology and Size Distribution.

Lyophilized beads were applied onto carbon taped stubs, sputter-coated and imaged with a Philips 515 scanning electron microscope (SEM). The size distribution of the beads was determined by analyzing ten SEM images and compiling the measurements for 500 beads (n=500).

Results

Gelatin-based, chemically crosslinked porous beads were obtained by spraying a concentrated gelatin solution into liquid nitrogen, lyophilizing the resulting beads then allowing them to react with carbodiimide. By varying the concentration of the crosslinking solution (from 0 to 1 M EDC), we were able to control the degree of crosslinking and synthesize beads with finely tunable enzymatic susceptibility.

Figure 11:
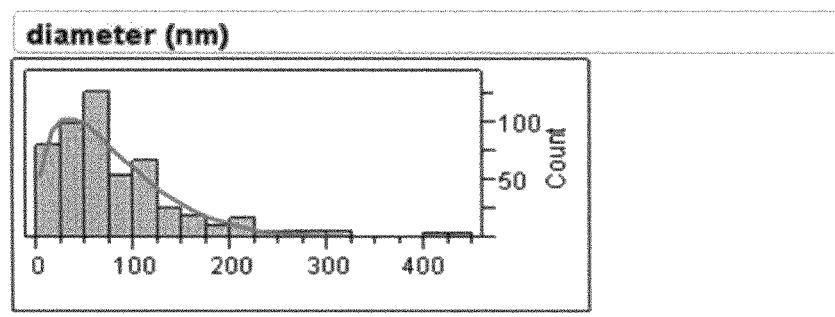
FIG. 11. Size distribution profile of beads.

The morphology and size distribution of the sprayed beads were analyzed by SEM (FIG. 10A-B). The beads appeared spherical with porous surfaces and mainly hollow cores. Hydration or crosslinking did not affect the physical features of the beads (results not shown). The size distribution of the overall population followed a Weibull distribution profile, specific for particles, with the majority of bead diameters smaller than 100 µm and typically ranging between 50-75 µm (FIG. 11). This morphology and size range is in agreement with our previous renal tissue engineering-targeted biomaterial screening studies (Basu supra 2011).

Figure 12:
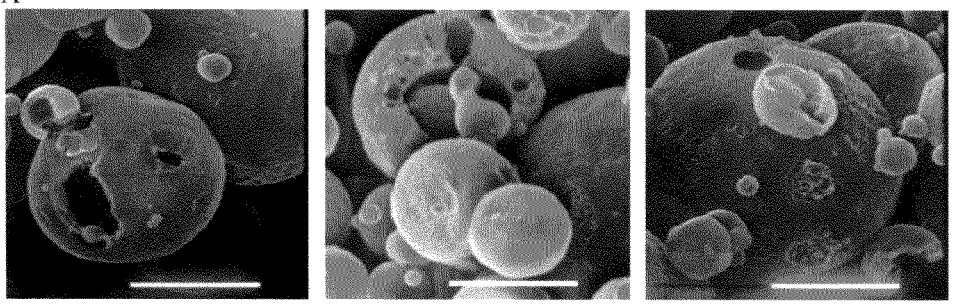
FIG. 12A-B. Surface topography of beads. Upper row (A)—SEM images of dry beads. Bottom row (B)—bright field microscope images of wet beads. Both sets of images illustrate the porous surface of the beads. The SEM images also illustrate the hollow interiors.
Figure 12:
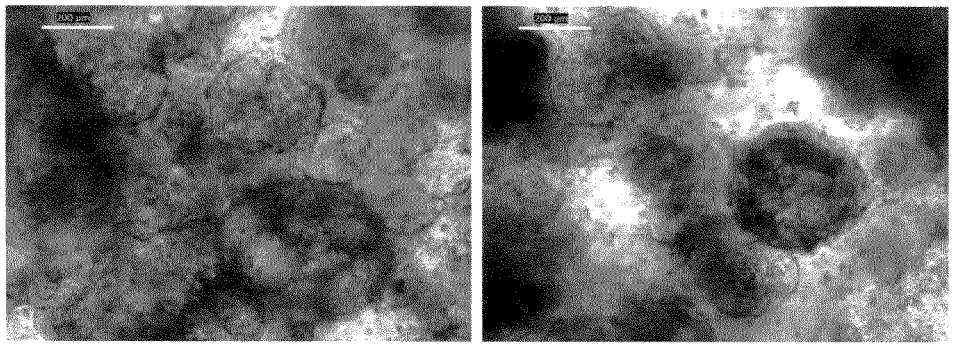

Moreover, the interior of the beads was hollow which would make them suitable for various applications as microcarriers. The overall surface of the beads had a porous appearance that was more pronounced in the wet state, due to hydration (FIG. 12A-B). The presence of the pores translates to increased cell attachment surface that would allow for a higher number of cells to attach compared to smooth surfaced counterparts. The aforementioned physical features, especially the bead sizes, are highly dependent on the casting process. In this case, the beads were obtained by using a stream of air to aerosolize the liquid gelatin solution and spray it into liquid nitrogen with a thin layer chromatography reagent sprayer (ACE Glassware). Modulation of the parameters associated with this process can result in different size distributions.

Figure 13:
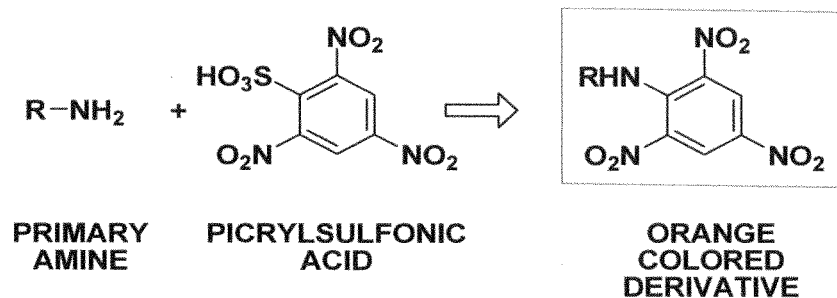
FIG. 13A-B. Amine quantification in crosslinked gelatins. A—Reaction scheme illustrating the formation of the orange adduct between primary amines and picryllsulfonic acid. B—Quantification of primary amine groups present in enzymatically digested differentially crosslinked gelatin beads (n=3). ANOVA statistical analysis P=0.007.
Figure 13:
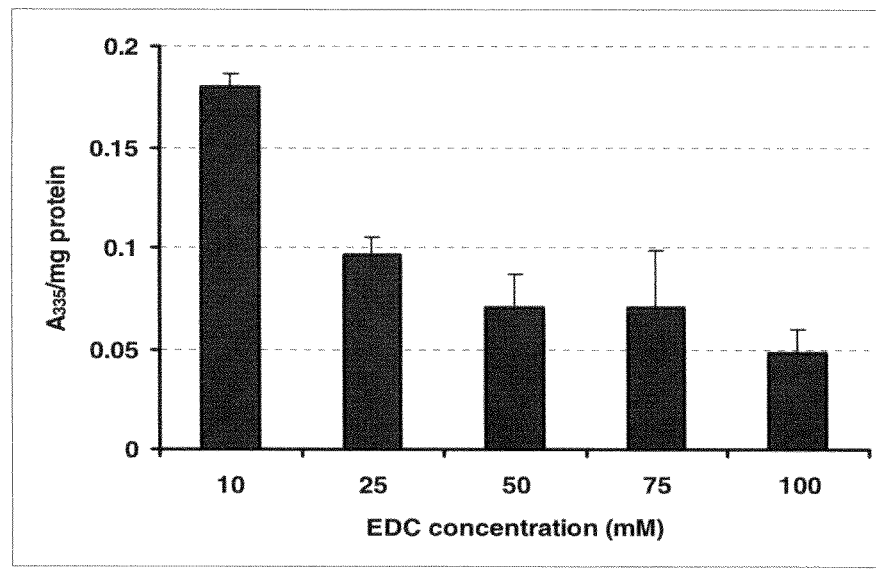

Under physiological conditions, non-crosslinked gelatin beads lose their integrity within minutes which limits their applicability spectrum as carriers. The goal was to develop a carrier system that would deliver cells to the desired site while also keeping them in place until they began integrating in the new environment. Moreover the carrier would mediate the tissue regeneration process through the localized, concerted interaction of the exogenous and endogenous cells. To this end, gelatin was covalently crosslinked by using a range of carbodiimide concentrations. The extent of crosslinking was determined by colorimetrically quantifying the number of primary amines still present in gelatin after reaction completion (FIG. 13A-B).

Beads treated with lower concentration of EDC were expected to have a higher number of free primary amines, while samples treated with high concentrations of crosslinker would have most of the primary amines engaged in amide bonds. The intensity of the orange color developed by the covalent bonding between the primary amine and picrylsulfonic acid, detectable spectrophotometrically at 335 nm, is proportional to the number of primary amines present in the sample. When normalized per milligram of protein present in the sample, our results showed a good inverse correlation between the number of free amines present and the initial concentration of EDC used for crosslinking. This result is indicative of differential bead crosslinking, dictated by the amount of carbodiimide used in the reaction.

Figure 14:
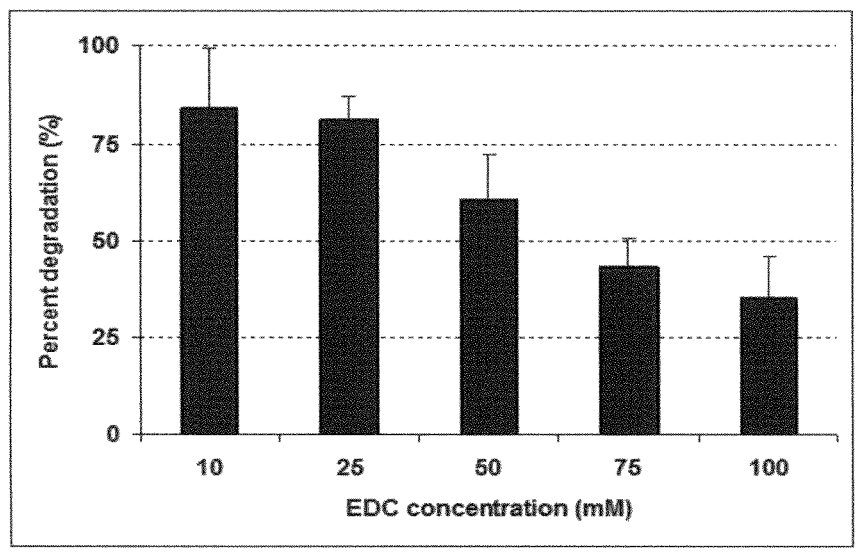
FIG. 14A-B. Enzymatic degradation profile of differentially crosslinked gelatin beads (A) and compared with Cultispher S beads (B).
Figure 14:
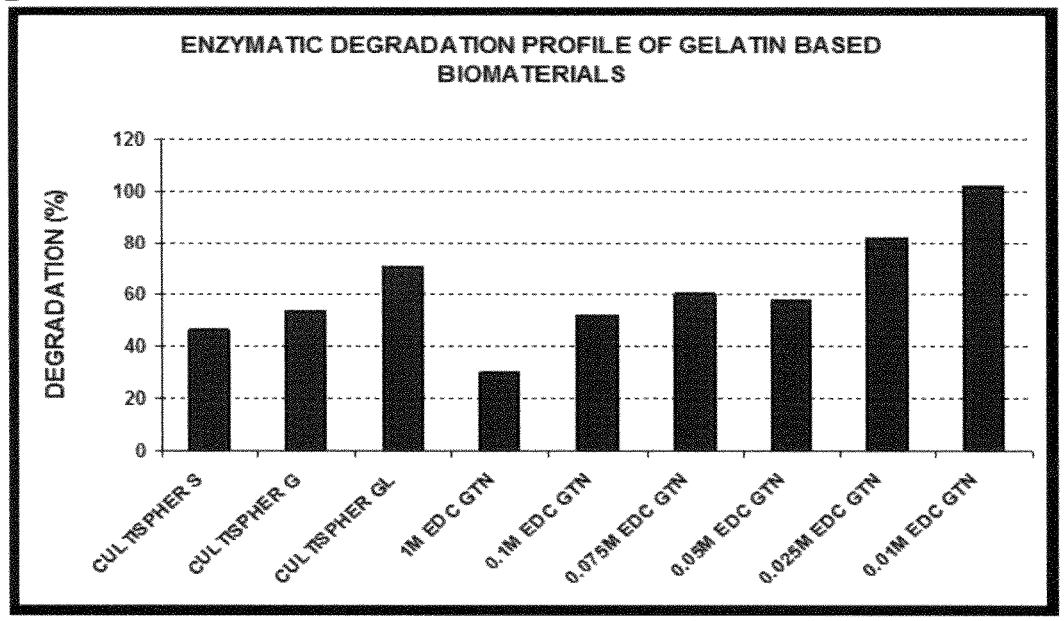

We hypothesized that the susceptibility of crosslinked gelatin beads to physiological parameters such as enzymatic degradation will be altered proportionally to the extent of chemical crosslinking. To test this, differentially crosslinked beads were partially degraded enzymatically and the data were normalized per total sample amount. Tunable enzymatic susceptibility was assessed in vitro by developing a screening test based on an optimized Bradford reagent assay. Samples were incubated for 1 h with 30 U of collagenase/dispase mix and assayed for degradation (n=3). Values were normalized to the total amount of gelatin in the sample as determined after complete enzymatic degradation (overnight). ANOVA statistical analysis P=0.0008. Exposure to collagenase/dispase released varying amounts of soluble protein from both Cultispher and crosslinked gelatin beads. For the gelatin beads, these in vitro degradation rates correlated well with the EDC concentrations used for crosslinking. Degradation rate of crosslinked gelatin beads was roughly proportional to concentration of EDC crosslinker after 1 hr exposure to collagenase/dispase enzyme mixture. Our results indicated that, in agreement with our hypothesis, samples with the highest crosslinking degree were the least susceptible to enzymatic degradation and the digestion rates correlated well ($R^2$=0.97) with the EDC concentration used in the reaction (FIG. 14A-B). The results suggest that the in vivo residence time of crosslinked beads would correlate with the extent of crosslinking.

Example 3—Validation of Cellularized Crosslinked Beads

The biodegradability of crosslinked beads was assessed both in vitro and in vivo after direct microinjection of the biomaterial into kidneys of healthy adult rats. To address the cytocompatibility of the crosslinked beads, primary rat kidney cells were cultured on crosslinked beads under dynamic conditions. After 24 hours, beads were assayed for cell viability. Uncrosslinked beads were not included in this assay as they liquefy under culturing conditions (temperature of 37° C.).

Methods

Selected Renal Cell (SRC) Preparation.

Biopsies are washed with Hanks Balanced Salt Solution (HESS) and minced, weighed, and dissociated in buffer comprised of 4 Units of Dispase 1 in HBSS, 300 Units/ml of Collagenase type IV with 5 mM $CaCl_2$. The resulting cell suspension is washed in a 1:1 mixture of high-glucose (4.5 g/L) DMEM:KSFM containing 5% (v/v) FBS before resuspending in a 1:1 mixture of high-glucose (4.5 g/L) DMEM:KSFM containing 5% (v/v) FBS, 2.5 μg human recombinant Epidermal Growth Factor 1-53 (rEGF 1-53), 25 mg Bovine Pituitary Extract (BPE), 1×ITS (insulin/transferrin/selenium), and with 1× antibiotic/antimycotic for plating. Incubation is carried out at 37° C./5% $CO_2$. Cells are detached for passage with 0.25% Trypsin with EDTA. Viability is assessed via Trypan Blue exclusion and enumeration was performed manually using a hemacytometer.

Prior to post-culture separation, cultures are transferred from near atmospheric oxygen conditions (16-21%) to a more physiologically relevant low-oxygen (2%) environment overnight. Cells are detached for harvest with 0.25% Trypsin containing EDTA. Viability is assessed via Trypan Blue exclusion and enumeration is performed manually using a hemacytometer. Cell suspensions are prepared as 60–75×$10^6$ cells in 2 mL unsupplemented KSFM (uKSFM) and separated on a two-step iodixanol (OptiPrep®; 60% w/v in uKSFM) density gradient (16%, 7%) in 15 mL conical polypropylene tubes by centrifugation at 800×g for 20 minutes at room temperature (without brake). Cell band at the interface between the 16% and 7% iodixanol layers are collected and washed 3× in sterile saline prior to formulation.

Formulation.

After banding, the Selected Renal Cells (SRC) are pelleted, counted, washed in saline, and a final wash in gelatin. Following the final centrifugation, gelatin solution supernatant is removed and sufficient volume of 0.75% gelatin containing 100 uM trolox equivalent is added to targeted volume/cell concentration.

Alternatively, SRC are first seeded onto crosslinked beads in a ratio of 2.5×$10^6$ cells/35 μl of beads (packed volume) and incubated overnight at 37° C./5% $CO_2$ with 1.5 ml basal medium/million cells in a tube in a rotating device set at 1 rpm. The basal medium consists of DMEM-HG (Invitrogen) mixed with Keratinocyte-SFM (Invitrogen) in a 1:1 volume ratio. These cell seeded beads are then gently pelleted by centrifugation, the supernatant removed, and then further formulated by resuspending in 10% gelatin solution in PBS. The 10% gelatin is a gel at ambient temperature, but liquid at 37° C. The gelatin:bead ratio was 1:5 by volume.

Cytocompatibility.

Formulated cells were assayed for viability 24 hours later by using a LIVE/DEAD® cell viability/cytotoxicity kit (Invitrogen, Carlsbad, Calif.).

In Vivo Implantation and Evaluation of Biomaterials.

Crosslinked beads were seeded with cells and formulated as described above. All experimental procedures were performed under PHS and IACUC guidelines of the Carolinas Medical Center. Under isoflurane anesthesia, female Lewis rats underwent a midline incision, and the left kidney was exposed. Formulated biomaterials (35 µl) were introduced by microinjection into the renal parenchyma (Basu supra 2011). Rats were sacrificed at 1 or 4 weeks post-injection. No early deaths occurred.

Statistical Analysis.

For the size distribution profile, bead diameter values were fitted with a two parameter Weibull equation. For the amine quantification and enzymatic digestion data, values were compared with single-factor ANOVA.

Results

Figure 16:
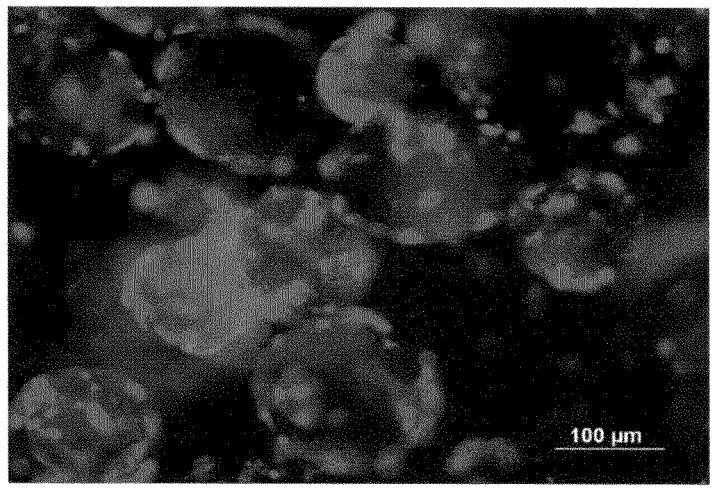
FIG. 16. Cytocompatibility of crosslinked beads. LIVE/DEAD® staining of primary rat kidney cells on crosslinked gelatin beads.

As anticipated, the beads sustained high cell attachment and viability (FIG. 15). The cytocompatibility of crosslinked beads were assessed by LIVE/DEAD® staining of primary rat kidney cells on crosslinked gelatin beads crosslinked with 25 mM EDC, after 24 h incubation under dynamic conditions (FIG. 16). The image of stained rat kidney cells on 25 mM EDC crosslinked beads was selected as representative for the series. By microscopic assessment both cell attachment and viability were found consistent with previously published data on the cytocompatibility of EDC crosslinked biomaterials (Lai et al. supra 2010; Lv et al. J Biomed Mater Res A 2008; 84: 198-207).

To further validate our in vitro observations, representative cellularized crosslinked beads (25, 50 and 100 mM EDC) were orthotopically injected into female Lewis rat kidneys and histologically evaluated after 1 week and 4 weeks. At 1 week, all injection sites for the crosslinked materials were characterized by an increased hypercellular response consisting predominantly of chronic inflammatory infiltrate (macrophages, plasma cells, lyphocytes and giant cells) with focal, mild tubular dilatation/atrophy and mild fibrogenic reaction. Overall, at this time point, we noted moderate degradation of biomaterials, and modest tissue in-growth and neovascularization. Importantly, already at 1 week post-injection the degradation pattern observed appeared to correlate well with the trends indicated by the in vitro data.

Figure 17:
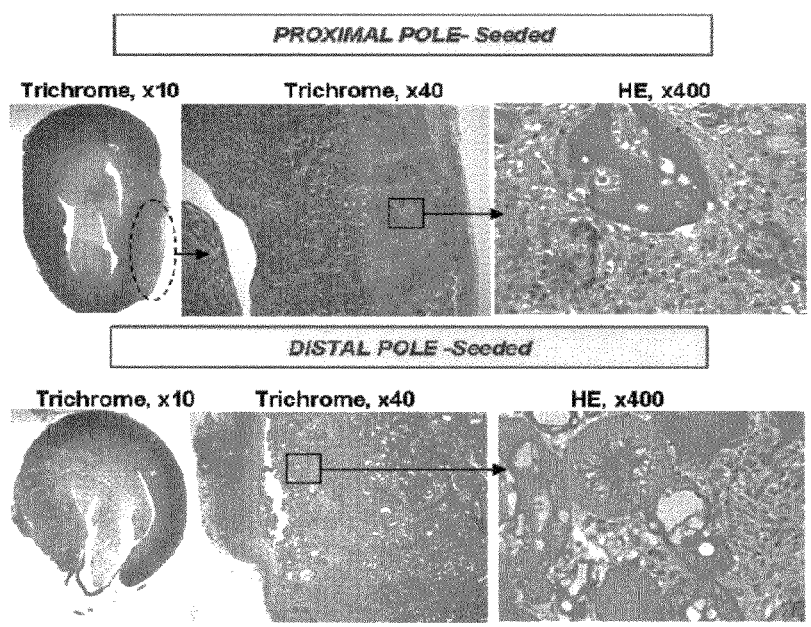
FIG. 17. Histology of kidney injected with 0.1M EDC crosslinked gelatin beads (1 week) illustrating the biocompatibility of the beads.
Figure 18:
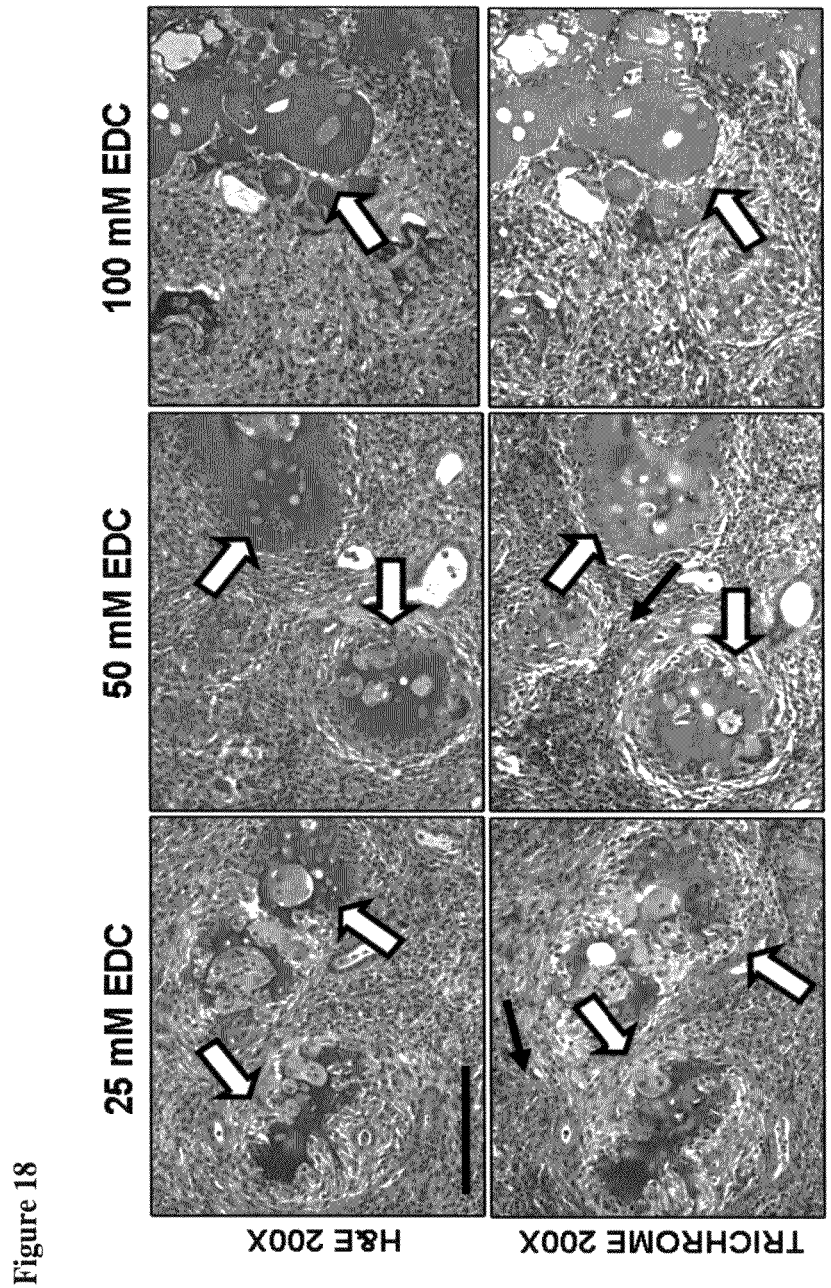
FIG. 18. Histological evaluation of kidney sections showing the degradation of crosslinked gelatin beads at 1 week post-injection.
Figure 19:
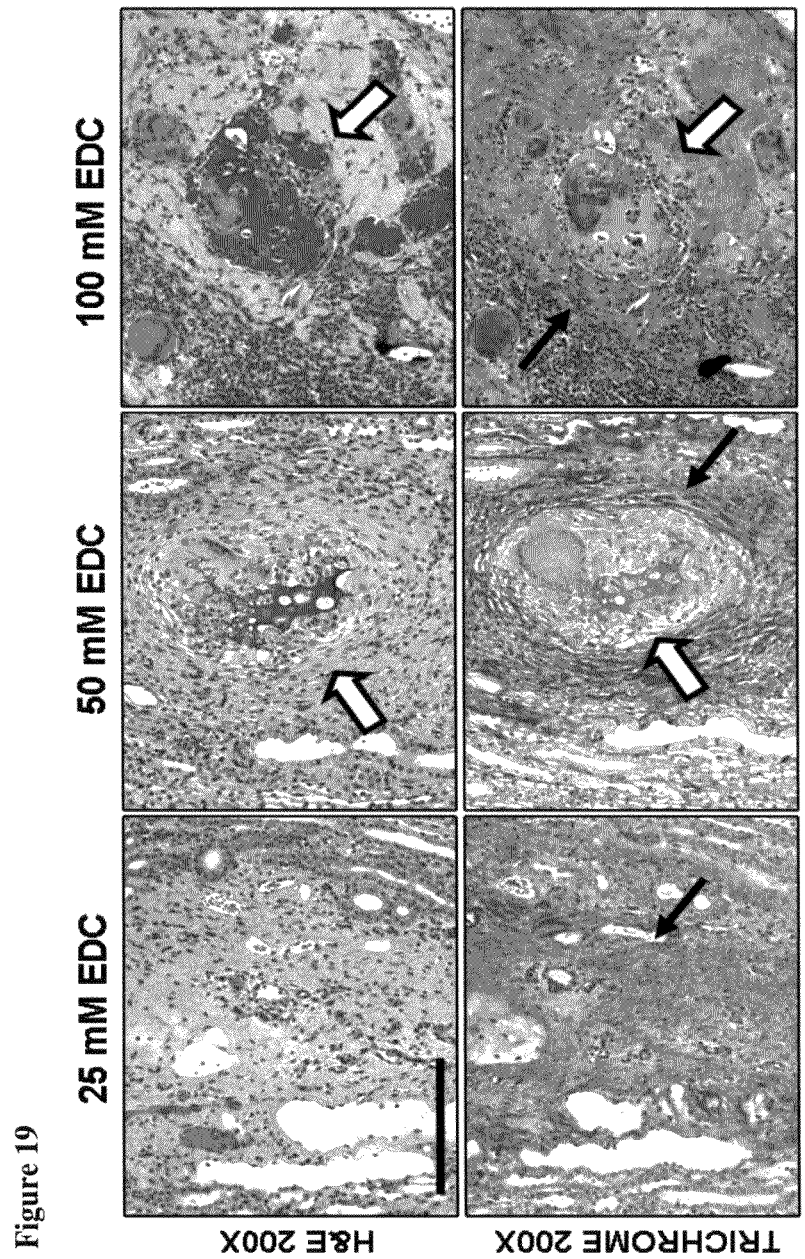
FIG. 19. Histological evaluation of kidney sections showing the degradation of crosslinked gelatin beads at 4 weeks post-injection.

The assessment of the in vivo performance of these biomaterials in rodents (kidney injections), confirmed that beads were biocompatible and able to confer a cytocompatible niche in which cells can function physiologically (FIG. 17). Moreover, the tunable degradation patterns of the crosslinked beads correlated with our in vitro observations (FIG. 18). FIG. 18 and FIG. 19 depict histological images of gelatin beads with rat cells seeded on them. The histology slides were stained with either Masson's Trichrome (which stains collagen blue) or hematoxylin & eosin (H&E). The images were evaluated for both positive indicators (tissue ingrowth, minimal to no detectable biomaterial at 1 month and healthy tissue) and negative indicators (presence of macrophages, giant cells, and other inflammatory cells; biomaterial persistence that supports a fibrotic capsule formation and an increase in the size of collecting ducts). These images show a robust tissue ingrowth into the biomaterials with minimal inflammatory response and a mild fibrotic capsule formation. In addition a well-vascularized tissue was formed in relation to the implant.

FIG. 18 shows histological evaluation of kidney sections showing the degradation of crosslinked gelatin beads at 1 week post-injection. White arrows indicate the crosslinked beads both in the H&E and Trichrome stained sections. Trichrome stains gelatin blue and allows the visualization of both the beads (white arrows) and gelatin traces (black arrows) resulting from bead degradation (scale bar for all images is 200 µm). At 4 weeks, all injection sites showed moderate fibro-cellular response and chronic interstitial inflammation (monocytic).

FIG. 19 shows histological evaluation of kidney sections showing the degradation of crosslinked gelatin beads at 4 weeks post-injection. White arrows indicate the crosslinked beads both in the H&E and Trichrome stained sections. Trichrome stains gelatin blue and allows the visualization of both the beads (white arrows) and gelatin traces (black arrows) resulting from bead degradation (scale bar for all images is 200 µm). The degradation of the biomaterial was ranked from moderate (100 mM EDC crosslinked) to marked (25 mM EDC crosslinked) (FIG. 19, beads are indicated by while arrows; black arrows indicate the degraded material). For the mM EDC crosslinked beads there was minimal residual biomaterial (beads), surrounded by mild chronic inflammation (macrophages and giant cells) with moderate to marked tissue in-growth and moderate neovascularization. Moderate to significant degradation was noted for the 50 mM EDC crosslinked beads, while the 100 mM EDC counterparts appeared as a partially (mildly) degraded amorphous aggregate of beads surrounded by moderate chronic inflammation consisting predominantly of macrophages and giant cell, some plasma cells and lymphocytes. Also, for this sample, moderate to marked fibrocellular response at the periphery with adequate tissue/cellular in-growth was noted (FIG. 19). Overall, our histological observations for both time points were consistent with the degradation patterns observed in our in vitro tests. In addition, the differentially crosslinked beads were well tolerated in vivo, did not induce the formation of fibrotic encapsulation of biomaterial and integrated well in the surrounding tissue.

The in vitro enzymatic degradation rate of gelatin-based beads can be controlled at synthesis with the concentration of ECD used for crosslinking. The fabrication process presented herein could represent a straightforward and cost-efficient process for producing biodegradable scaffolds with tunable enzymatic susceptibility using a reagent that is currently used in the production of clinical products. The translation of tunable in vitro degradation to tunable in vivo degradation is under active study and could potentially represent a useful platform technology for producing biomaterials where the temporal persistence of the spatial and structural characteristics could be optimized to the specific needs of the organ and/or tissue being regenerated.

The control over the physicochemical and biological properties of biomaterials is important for the success of any tissue engineering application. In our case, one requirement was for a biomaterial with a specific in vivo residence time that would deliver viable cells to the desired site, provide space for regenerative changes from cellular infiltration and proliferation, then gradually resorb while allowing cells to adapt to the new environmental conditions and differentiate into appropriate tissues and organs. We showed here that by using EDC (a carbodiimide widely employed in the manufacturing of collagen-based FDA-approved devices) and a water-based chemical crosslinking process we could obtain gelatin beads with biodegradation rates spanning across a significant range. Moreover, the process is highly reproducible. Overall this approach offers an effective and efficient means for producing tissue engineering biomaterials with organ specific biodegradation rates.

Overall, we were able to manufacture gelatin-based microbeads that can serve as spacers, cell delivery systems or microcarriers for various molecules. This design explores the concentration dependent melting temperature of gelatin and applies this feature to yield temperature responsive spacer beads. Furthermore, by using simple, well characterized chemistry, these beads can be tailored to follow a desired enzymatic degradation rate, both in vivo and in vitro. Previously reported similarly crosslinked systems did not have the physical features reported here, which makes our system more suitable for microcarrier or cell delivery applications.

Example 4—Bio-Response of a Rodent Hemi-Nephrectomy Model to Implantation of Neo-Kidney Augment Prototypes Composed of Selected Renal Cells and Biomaterials Towards addressing the need for new treatments to restore renal function, a unique integrated regenerative medicine technology platform capable of catalyzing regeneration of tissues and organs has been developed.

The Neo-Kidney Augment (NKA) product prototype, comprised of biomaterials and selected regenerative renal cells (SRC), is one such platform capable of facilitating regeneration of kidney tissue. SRC are obtained from enzymatic digestion of a kidney biopsy and density gradient separation of cells. Gelatin based hydrogels (GBH) were used as biomaterial. Bio-response of mammalian kidney towards implantation of NKA prototypes has previously been evaluated in healthy adult rodents (Basu et al., 2011, Cell Transplantation, in press). However, removal of single kidney from rodents (hemi-nephrectomy) increases sensitivity of the model, permitting detection of systemically acting toxicological effects. In this study, 15 hemi-nephrectomized rodents were injected with NKA prototypes within the renal parenchyma of the remnant kidney and evaluated for key renal physiological indices.

Methods

Figure 20:
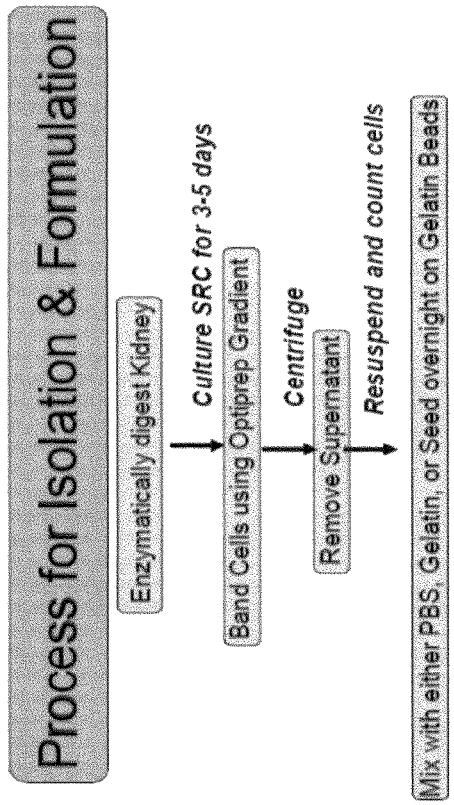
FIG. 20: Outline for strategy for creation of NKA prototypes

Neo-Kidney Augment prototypes were made by combining selected renal cells with biomaterials as shown in Table 1. Cell/biomaterial constructs were prepared as shown in FIG. 20 (outline for strategy for creation of NKA constructs).

Gelatin Solution Preparation:

The quantities of powdered gelatin and trolox equivalent/PBS needed to make a 0.75% or 1.0% w/v gelatin/100 μM trolox equivalent solution are calculated. The PBS is placed in a beaker with a magnetic stir bar and warmed on a stirring hot plate set to 50° C. for 15 minutes. The gelatin is slowly added and the mixture is allowed to stir at 50° C. for 1 hour. The resulting gelatin solution is filtered using a pre-warmed sterile filter assembly. The sterile gelatin solution is then aliquotted into smaller volumes (10 ml in 15 ml tubes) and stored at 4° C. until use.

A preferred approach is to make a 0.76% or 1.01% gelatin solution in PBS, then add a sufficient volume of 100× (10 mM) trolox equivalent when mixing with the SRC to yield the desired 0.75% (or 1.0%) gelatin/100 μM trolox equivalent solution.

TABLE 1

Summary of biomaterials delivery to hemi-nephrectomized rodent groups.

| Group | Animal | Materials | # Injections/kidney | Injection volume (per pole (ul)) | Cells (B2, B3, B4)/Injection | Delivery System |
|---|---|---|---|---|---|---|
| A | HN07 | Cells in PBS | 2 | 150 | 2.5 × 10e6 | 18 gauge |
| A | HN11 | PBS + Trolox | 2 | 150 | 7.5 × 10e6 | 18 gauge |
| A | HN15 | Cells in PBS + Trolox | 2 | 150 | 7.5 × 10e6 | 18 gauge |
| A | HN21 | PBS No Trolox + Cells | 2 | 150 | 7.5 × 10e6 (15 million per kidney) | 18 gauge |
| B | HN08 | Gelatin (1.0%) + Cells in PBS | 2 | 150 | 2.5 × 10e6 | 18 gauge |
| B | HN12 | Gelatin (1.0%) + Cells in PBS + Trolox | 2 | 150 | 7.5 × 10e6 | 18 gauge |
| B | HN16 | Gelatin (0.75%) in PBS + Trolox | 2 | 150 | 7.5 × 10e6 | 18 gauge |
| B | HN23 | Gelatin (0.75%) + Trolox + Cells | 2 | 150 | 7.5 × 10e6 (15 million per kidney) | 18 gauge |
| C | HN09 | Gelatin (1.0%) + 10% Tng Beads (0.50M) in PBS | 2 | 50 | 2.5 × 10e6 | 18 gauge |
| C | HN10 | Gelatin (1.0%) + 10% Tng Beads (25 mM) in PBS + Trolox | 2 | 150 | 7.5 × 10e6 | 18 gauge |
| C | HN13 | Gelatin (1.0%) + 10% Tng Beads (25 mM) in PBS + Trolox | 2 | 50 | 2.5 × 10e6 | 18 gauge |
| C | HN14 | Gelatin (1.0%) + 10% Tng Beads (25 mM) in PBS + Trolox | 2 | 150 | 7.5 × 10e6 | 18 gauge |

TABLE 1-continued

Summary of biomaterials delivery to hemi-nephrectomized rodent groups.

| Group | Animal | Materials | # Injections/ kidney | Injection volume (per pole (ul)) | Cells (B2, B3, B4)/ Injection | Delivery System |
|---|---|---|---|---|---|---|
| C | HN18 | Gelatin (0.75%) + 10% Tng Beads (25 mM) in Basal Media + | 2 | 50 | 2.5 × 10e6 | 18 gauge |
| C | HN24 | Gelatin (0.75%) + Trolox + 10% TNG Beads + Cells | 2 | 150 | 7.5 × 10e6 (15 million per kidney) | 18 gauge |
| C | HN25 | Gelatin (0.75%) + Trolox + 10% TNG Beads + Cells | 2 | 150 | 7.5 × 10e6 (15 million per kidney) | 18 gauge |

Figure 21:
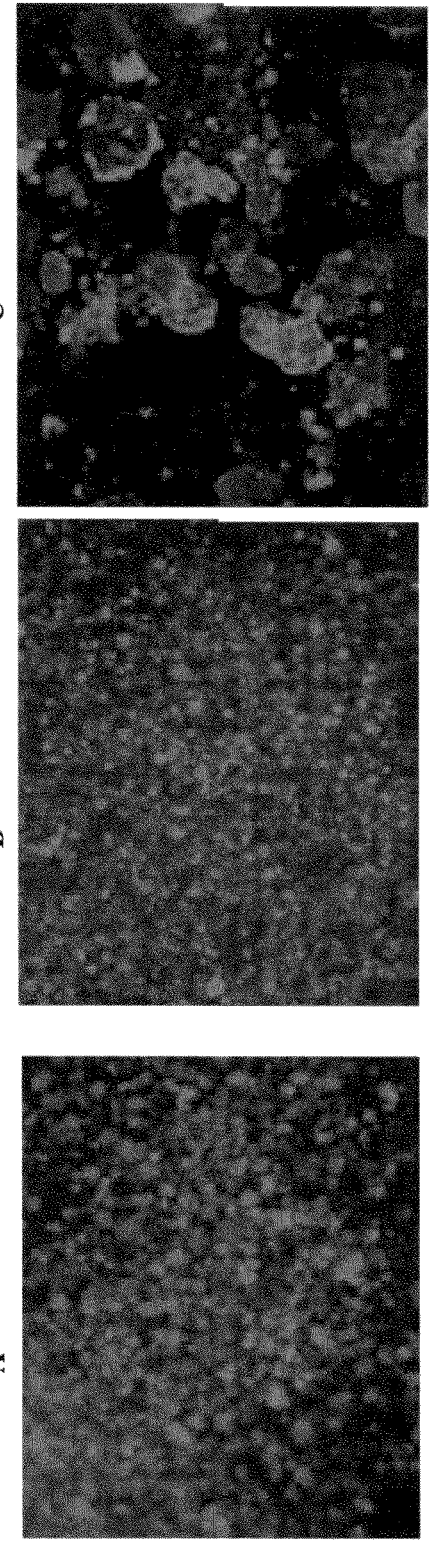
FIG. 21A-C: Representative live/dead staining of selected rodent regenerative renal cell biomaterial constructs (A: Cells/PBS; B: Cells/GBH; C: Cells/beads).

Results:

FIG. 21A-C shows representative live/dead staining of selected rodent regenerative renal cell biomaterial constructs. The constructs were delivered to remnant kidney of hemi-nephrectomized Lewis rats (2 months old) through 18 gauge needle. Physiological indices derived from whole blood, serum and urine chemistries were evaluated either prior to implantation or at 4 week time points post-implantation. Animals were sacrificed at 4 weeks post-injection and remnant kidneys were examined histologically for evidence of inflammatory or fibrotic bioresponse.

Implantation of NKA prototypes did not significantly affect key renal physiological indices, and presented minimal evidence of inflammatory, necrotic or fibrotic bioresponse. Therefore, NKA prototypes based on SRC in GBH are well tolerated by remnant kidney in the rodent heminephrectomy model.

Figure 22:
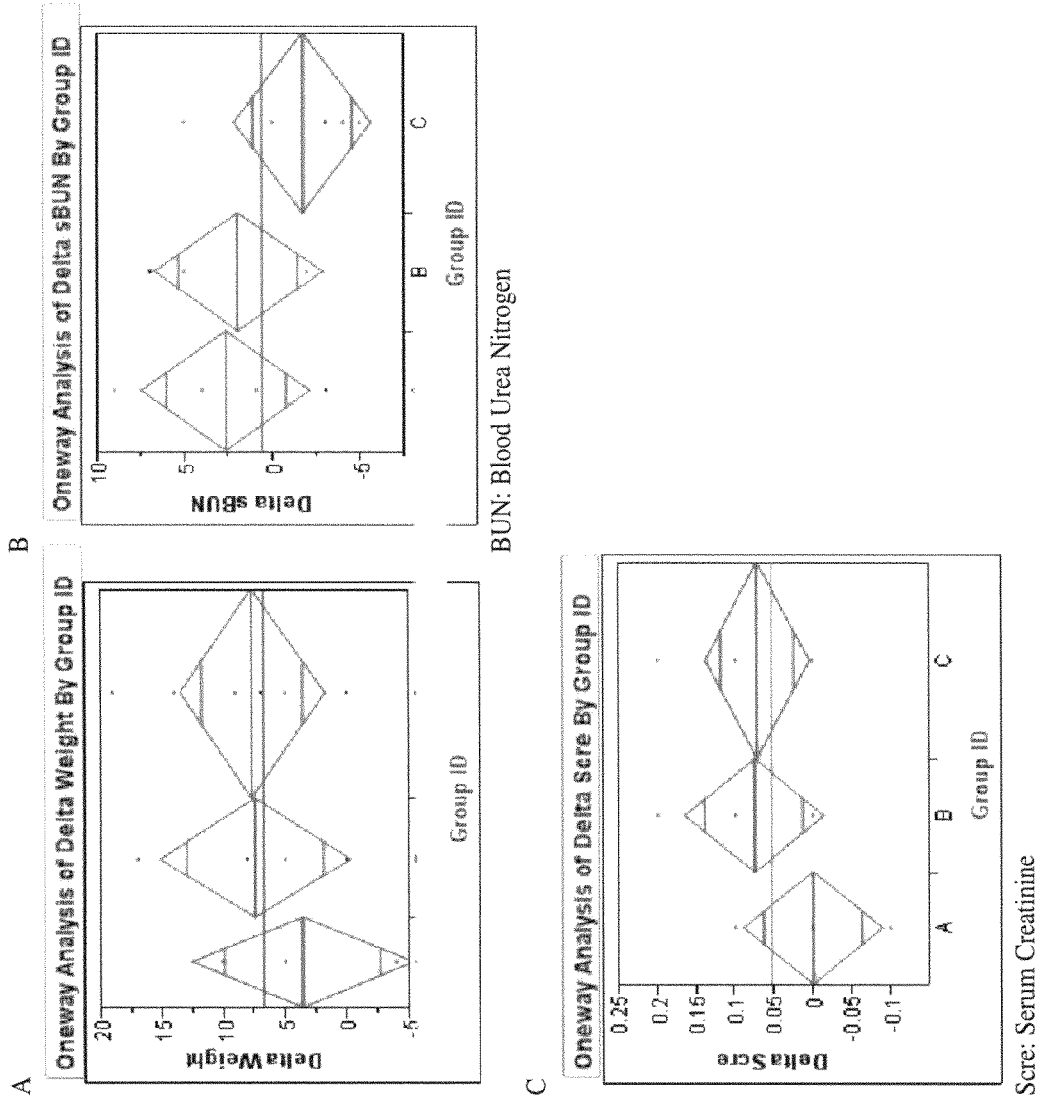
FIG. 22A-C: Summary of key renal physiological indices in 4 weeks post-implantation (ANOVA analysis). (A) body weight; (B) Blood Urea Nitrogen (BUN); (C) Serum Creatinine (Scre)

FIG. 22 shows a summary of the change in body weight (A), blood urea nitrogen levels (B) and serum creatine levels (C) by group 4 weeks post-implantation (ANOVA analysis)—A: Oneway Analysis of Delta Weight by Group ID; B: Oneway Analysis of Delta sBUN by Group ID (BUN: Blood Urea Nitrogen); C: Oneway Analysis of Delta Scre by Group ID (Scre: serum creatinine).

Figure 23:
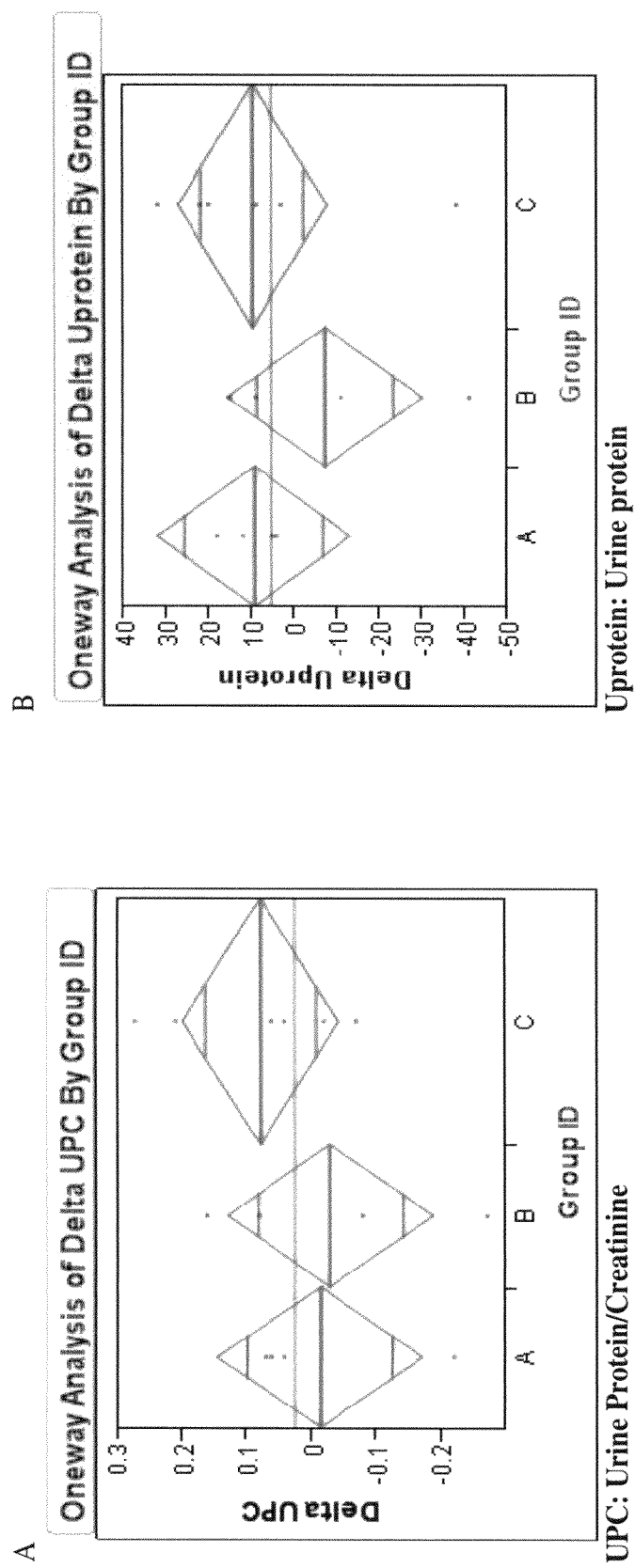
FIG. 23A-B: Summary of (A) Urine Protein/Creatinine (UPC) and (B) Urine protein (Uprotein) as renal physiological indices 4 weeks post-implantation (ANOVA analysis)

FIG. 23 shows a summary of the change in urine protein/ creatinine (A) and urine protein (B) by group 4 weeks post-implantation (ANOVA analysis)—A: Oneway Analysis of Delta UPC by Group ID (UPC: Urine Protein/Creatinine); B: Oneway Analysis of Delta Uprotein by Group ID (Uprotein: Urine protein).

Figure 24:
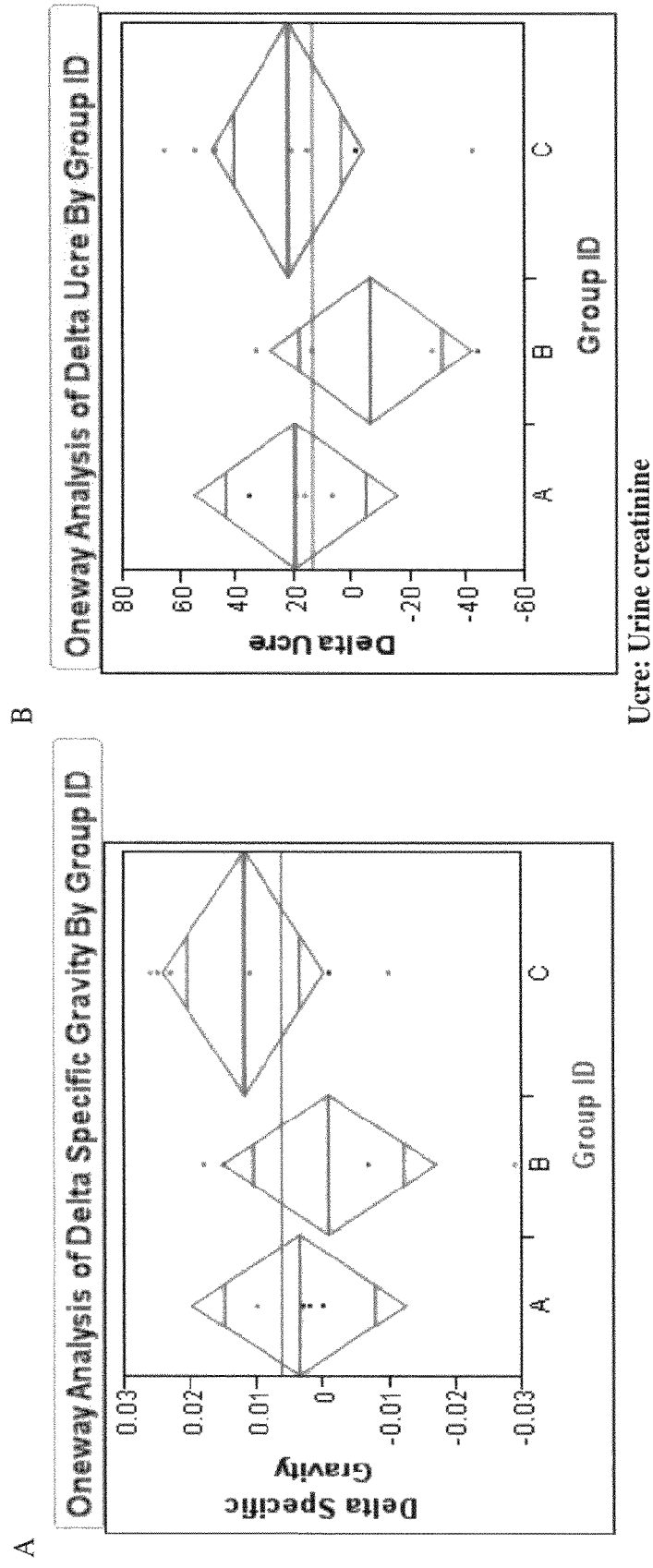
FIG. 24A-B: Summary of (A) Specific Gravity and (B) Urine creatinine (Ucre) as renal physiological indices 4 weeks post-implantation (ANOVA analysis)

FIG. 24 shows a summary of the change in specific gravity (A) and urine creatinine (B) by group 4 weeks post-implantation (ANOVA analysis)—A: Oneway Analysis of Delta Specific Gravity by Group ID; B: Oneway Analysis of Delta Ucre by Group ID (Ucre: Urine creatinine). Overall, introduction of cell/biomaterial constructs within hemi-nephrectomy rodent model did not impact key indicators of renal physiology over a one month period of time as compared to SRC.

Introduction of cell/biomaterial constructs within the hemi-nephrectomy rodent model also did not significantly impact histology of remnant kidney.

Figure 25:
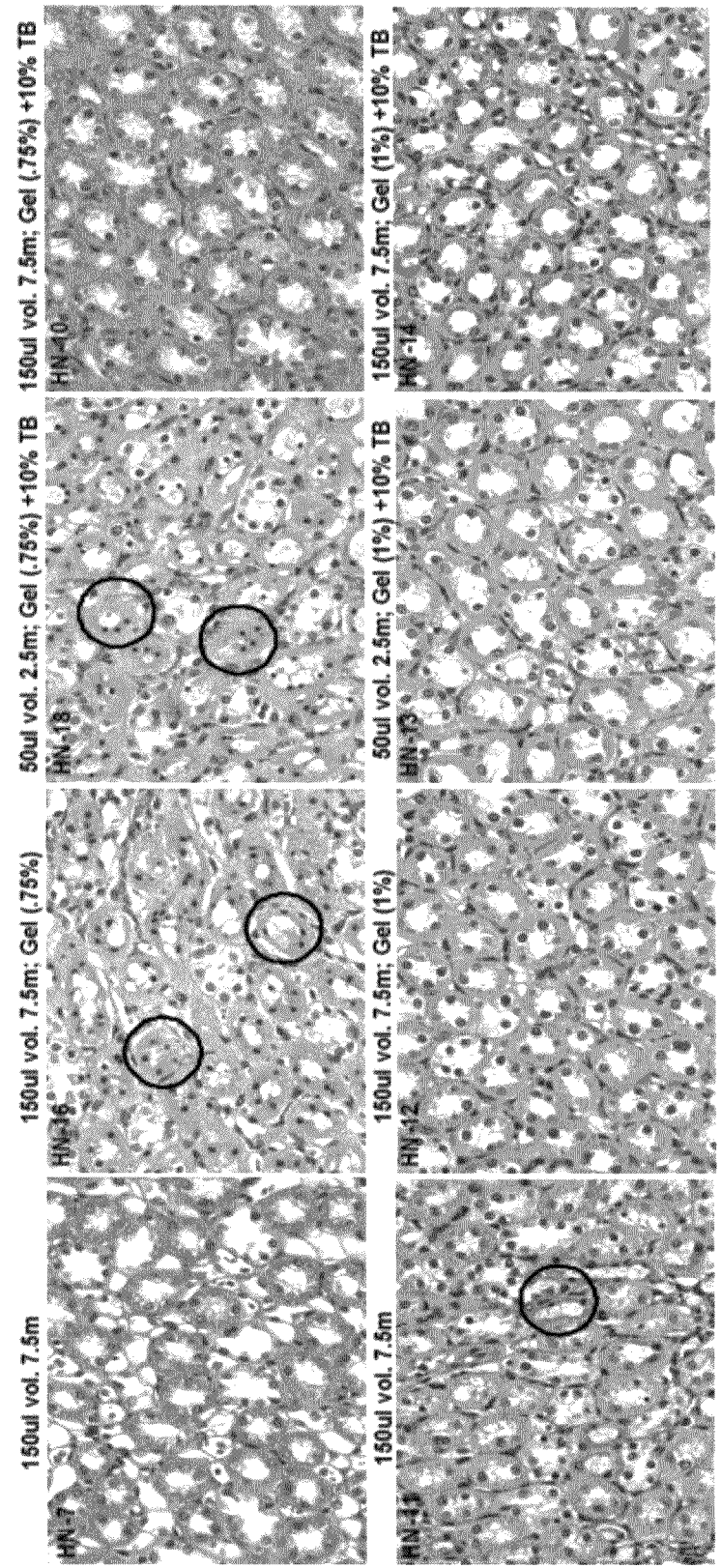
FIG. 25: Representative histological outcomes associated with implantation of cell/biomaterial constructs within rodent kidney in hemi-nephrectomy model.

FIG. 25 shows 4-Wks Post hemi-nephrectomized Rats; kidney Outer Medulla (inner stripe); HE, x400. Batch A (top row of FIG. 25), tubular necrosis characterized by piknotic nuclei (described in batch 1) were also observed in rat nos. (HN-16 and HN-18) but not in HN-7 and HN-10, which showed no significant lesions within the kidney parenchyma. Batch B (bottom row of FIG. 25); minimal, focal tubular necrosis showing piknotic nuclei in the inner stripe of outer medulla were observed one rat (HN11) but not observed in the remaining animals (HN-12, HN-13 and HN-14), and thus considered within normal limits.

In summary, implantation of selected renal cell/biomaterial Neo-Kidney Augment prototypes into rodent hemi-nephrectomy model does not impact remnant kidney physiology or histology.

Example 5—Isolation & Characterization of Bioresponsive Renal Cells

Figure 3:
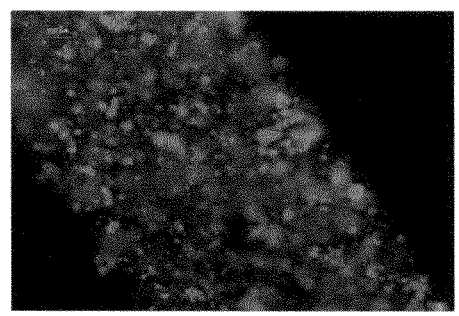
FIG. 3. Matrix containing cell aggregates.
Figure 4:
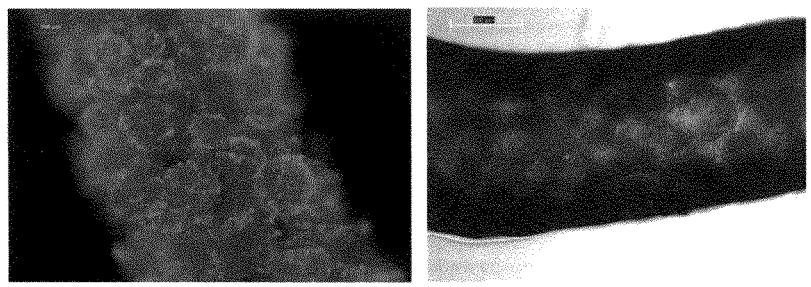
FIG. 4. Matrix containing cells attached to microcarrier beads.

A case of idiopathic progressive chronic kidney disease (CKD) with anemia in an adult male swine (Sus scrofa) provided fresh diseased kidney tissue for the assessment of cellular composition and characterization with direct comparison to age-matched normal swine kidney tissue. Histological examination of the kidney tissue at the time of harvest confirmed renal disease characterized by severe diffuse chronic interstitial fibrosis and crescentic glomerulonephritis with multifocal fibrosis. Clinical chemistry confirmed azotemia (elevation of blood urea nitrogen and serum creatinine), and mild anemia (mild reduction in hematocrit and depressed hemoglobin levels). Cells were isolated, expanded, and characterized from both diseased and normal kidney tissue. As shown in FIG. 1 of Presnell et al. WO/2010/056328 (incorporated herein by reference in its entirety), a Gomori's Trichrome stain highlighs the fibrosis (blue staining indicated by arrows) in the diseased kidney tissue compared to the normal kidney tissue. Functional tubular cells, expressing cubulin:megalin and capable of receptor-mediated albumin transport, were propagated from both normal and diseased kidney tissue. Erythropoietin (EPO)-expressing cells were also present in the cultures and were retained through multiple passages and freeze/thaw cycles. Furthermore, molecular analyses confirmed that the EPO-expressing cells from both normal and diseased tissue responded to hypoxic conditions in vitro with HIF1α-driven induction of EPO and other hypoxia-regulated gene targets, including vEGF. Cells were isolated from the porcine kidney tissue via enzymatic digestion with collagenase+dispase, and were also isolated in separate experiments by performing simple mechanical digestion and explant culture. At passage two, explant-derived cell cultures containing epo-expressing cells were subjected to both atmospheric (21%) and varying hypoxic (<5%) culture conditions to determine whether exposure to hypoxia culminated in upregulation of EPO gene expression. As noted with rodent cultures (see Example 3), the normal pig displayed oxygen-dependent expression and regulation of the EPO gene. Surprisingly, despite the uremic/anemic state of the CKD pig (Hematocrit <34, Creatinine >9.0) EPO expressing cells were easily isolated and propagated from the tissue and expression of the EPO gene remained hypoxia regulated, as shown in FIG. 2 of Presnell et al. WO/2010/056328 (incorporated herein by reference in its entirety). As shown in FIG. 3 of Presnell et al. WO/2010/056328 (incorporated herein by reference in its entirety), cells in the propagated cultures demonstrated the ability to self-organize into tubule-like structures. As shown in FIG. 4 of Presnell et al. WO/2010/056328 (incorporated herein by reference in its entirety), the presence of functional tubular cells in the culture (at passage 3) was confirmed by observing receptor-mediated uptake of FITC-conjugated Albumin by the cultured cells. The green dots (indicated by thin white arrows) represent endocytosed fluorescein-conjugated albumin which is mediated by tubular cell-specific receptors, Megalin and Cubilin, indicating protein reabosroption by functional tubular cells. The blue staining (indicated by thick white arrows) is Hoescht-stained nuclei. Taken together, these data suggest that functional tubular and endocrine cells can be isolated and propagated from porcine renal tissues, even in renal tissues that have been severely compromised with CKD. Furthermore, these findings support the advancement of autologous cell-based therapeutic products for the treatment of CKD.

In addition, EPO-producing cells were isolated enzymatically from normal adult human kidney (as described above in Example 1). As shown in FIG. 5 of Presnell et al. WO/2010/056328 (incorporated herein by reference in its entirety), the isolation procedure resulted in more relative EPO expression after isolation than in the initial tissue. As shown in FIG. 6 of Presnell et al. WO/2010/056328 (incorporated herein by reference in its entirety), it is possible to maintain the human EPO producing cells in culture with retention of EPO gene expression. Human cells were cultured/propagated on plain tissue-culture treated plastic or plastic that had been coated with some extracellular matrix, such as, for instance, fibronectin or collagen, and all were found to support EPO expression over time.

Example 6—Isolation & Enrichment of Specific Bioreactive Renal Cells

Kidney Cell Isolation:

Briefly, batches of 10, 2-week-old male Lewis rat kidneys were obtained from a commercial supplier (Hilltop Lab Animals Inc.) and shipped overnight in Viaspan preservation medium at a temperature around 4° C. All steps described herein were carried out in a biological safety cabinet (BSC) to preserve sterility. The kidneys were washed in Hank's balanced salt solution (HBSS) 3 times to rinse out the Viaspan preservation medium. After the third wash the remaining kidney capsules were removed as well as any remaining stromaltissue. The major calyx was also removed using micro dissection techniques. The kidneys were then finely minced into a slurry using a sterile scalpel. The slurry was then transferred into a 50 ml conical centrifuge tube and weighed. A small sample was collected for RNA and placed into an RNAse-free sterile 1.5 ml micro-centrifuge tube and snap frozen in liquid nitrogen. Once frozen, it was then transferred to the −80 degree freezer until analysis. The tissue weight of 10 juvenile kidneys equaled approximately 1 gram. Based on the weight of the batch, the digestion medium was adjusted to deliver 20 mls of digestion medium per 1 gram of tissue. Digestion buffer for this procedure contained 4 Units of Dispase 1 (Stem Cell Tech) in HBSS, 300 Units/ml of Collagenase type IV (Worthington) with 5 mM $CaCl_2$ (Sigma).

The appropriate volume of pre-warmed digestion buffer was added to the tube, which was then sealed and placed on a rocker in a 37° C. incubator for 20 minutes. This first digestion step removes many red blood cells and enhances the digestion of the remaining tissue. After 20 minutes, the tube was removed and placed in the BSC. The tissue was allowed to settle at the bottom of the tube and then the supernatant was removed. The remaining tissue was then supplemented with fresh digestion buffer equaling the starting volume. The tube was again placed on a rocker in a 37° C. incubator for an additional 30 minutes.

After 30 minutes the digestion mixture was pipetted through a 70 µm cell strainer (BD Falcon) into an equal volume of neutralization buffer (DMEM w/10% FBS) to stop the digestion reaction. The cell suspension was then washed by centrifugation at 300×g for 5 min. After centrifugation, the pellet was then re-suspended in 20 mls KSFM medium and a sample acquired for cell counting and viability assessment using trypan blue exclusion. Once the cell count was calculated, 1 million cells were collected for RNA, washed in PBS, and snap frozen in liquid nitrogen. The remaining cell suspension was brought up to 50 mls with KSFM medium and washed again by centrifugation at 300×g for 5 minutes. After washing, the cell pellet was re-suspended in a concentration of 15 million cells per ml of KSFM.

Five milliliters of kidney cell suspension were then added to 5 mls of 30% (w/v) Optiprep® in 15 ml conical centrifuge tubes (BD Falcon) and mixed by inversion 6 times. This formed a final mixture of 15% (w/v) of Optiprep®. Post inversion, tubes were carefully layered with 1 mL PBS. The tubes were centrifuged at 800×g for 15 minutes without brake. After centrifugation, the tubes were removed and a cell band was formed at the top of the mixing gradient. There was also a pellet containing red blood cells, dead cells, and a small population of live cells that included some small less granular cells, some epo-producing cells, some tubular cells, and some endothelial cells. The band was carefully removed using a pipette and transferred to another 15 ml conical tube. The gradient medium was removed by aspiration and the pellet was collected by re-suspension in 1 ml KSFM. The band cells and pellet cells were then recombined and re-suspended in at least 3 dilutions of the collected band volume using KSFM and washed by centrifugation at 300×g for 5 minutes. Post washing, the cells were re-suspended in 20 mls of KSFM and a sample for cell counting was collected. Once the cell count was calculated using trypan blue exclusion, 1 million cells were collected for an RNA sample, washed in PBS, and snap frozen in liquid nitrogen.

Pre-Culture 'Clean-Up' to Enhance Viability and Culture Performance of Specific Bioactive Renal Cells Using Density Gradient Separation:

To yield a clean, viable population of cells for culture, a cell suspension was first generated as described above in "Kidney Cell Isolation". As an optional step and as a means of cleaning up the initial preparation, up to 100 million total cells, suspended in sterile isotonic buffer were mixed thoroughly 1:1 with an equal volume of 30% Optiprep® prepared at room temperature from stock 60% (w/v) iodixanol (thus yielding a final 15% w/v Optiprep solution) and mixed thoroughly by inversion six times. After mixing, 1 ml PBS buffer was carefully layered on top of the mixed cell suspension. The gradient tubes were then carefully loaded into the centrifuge, ensuring appropriate balance. The gradient tubes were centrifuged at 800×g for 15 minutes at 25° C. without brake. The cleaned-up cell population (containing viable and functional collecting duct, tubular, endocrine, glomerular, and vascular cells) segmented between 6% and 8% (w/v) Optiprep®, corresponding to a density between 1.025-1.045 g/mL. Other cells and debris pelleted to the bottom of the tube.

Kidney Cell Culture:

The combined cell band and pellet were then plated in tissue culture treated triple flasks (Nunc T500) or equivalent at a cell concentration of 30,000 cells per cm2 in 150 mls of a 50:50 mixture of DMEM (high glucose)/KSFM containing 5% (v/v) FBS, 2.5 µg EGF, 25 mg BPE, 1×ITS (insulin/transferrin/sodium selenite medium supplement) with antibiotic/antimycotic. The cells were cultured in a humidified 5% CO2 incubator for 2-3 days, providing a 21% atmospheric oxygen level for the cells. After two days, the medium was changed and the cultures were placed in 2% oxygen-level environment provided by a CO2/Nitrogen gas multigas humidified incubator (Sanyo) for 24 hrs. Following the 24 hr incubation, the cells were washed with 60 mls of 1×PBS and then removed using 40 mls 0.25% (w/v) trypsin/EDTA (Gibco). Upon removal, the cell suspension was neutralized with an equal volume of KSFM containing 10% FBS. The cells were then washed by centrifugation 300×g for 10 minutes. After washing, the cells were re-suspended in 20 mls of KSFM and transferred to a 50 ml conical tube and a sample was collected for cell counting. Once the viable cell count was determined using trypan blue exclusion, 1 million cells were collected for an RNA sample, washed in PBS, and snap frozen in liquid nitrogen. The cells were washed again in PBS and collected by centrifugation at 300×g for 5 minutes. The washed cell pellet was re-suspended in KSFM at a concentration of 37.5 million cells/ml.

Enriching for Specific Bioactive Renal Cells Using Density Step Gradient Separation:

Cultured kidney cells, predominantly composed of renal tubular cells but containing small subpopulations of other cell types (collecting duct, glomerular, vascular, and endocrine) were separated into their component subpopulations using a density step gradient made from multiple concentrations w/v of iodixanol (Optiprep). The cultures were placed into a hypoxic environment for up to 24 hours prior to harvest and application to the gradient. A stepped gradient was created by layering four different density mediums on top of each other in a sterile 15 mL conical tube, placing the solution with the highest density on the bottom and layering to the least dense solution on the top. Cells were applied to the top of the step gradient and centrifuged, which resulted in segregation of the population into multiple bands based on size and granularity.

Briefly, densities of 7, 11, 13, and 16% Optiprep® (60% w/v Iodixanol) were made using KFSM medium as diluents. For example: for 50 mls of 7% (w/v) Optiprep®, 5.83 mls of stock 60% (w/v) Iodixanol was added to 44.17 mls of KSFM medium and mixed well by inversion. A peristaltic pump (Master Flex US) loaded with sterile L/S 16 Tygon tubing connected to sterile capillary tubes was set to a flow rate of 2 ml per minute, and 2 mL of each of the four solutions was loaded into a sterile conical 15 mL tube, beginning with the 16% solution, followed by the 13% solution, the 11% solution, and the 7% solution. Finally, 2 mL of cell suspension containing 75 million cultured rodent kidney cells was loaded atop the step gradient (suspensions having been generated as described above in 'Kidney cell Culture'). Importantly, as the pump was started to deliver the gradient solutions to the tube, care was taken to allow the fluid to flow slowly down the side of the tube at a 45° angle to insure that a proper interface formed between each layer of the gradient. The step gradients, loaded with cells, were then centrifuged at 800×g for 20 minutes without brake. After centrifugation, the tubes were carefully removed so as not to disturb each interface. Five distinct cell fractions resulted (4 bands and a pellet) (B1-B4, +Pellet) (see FIG. 26, left conical tube). Each fraction was collected using either a sterile disposable bulb pipette or a 5 ml pipette and characterized phenotypically and functionally (See Example 10 of Presnell et al. WO/2010/056328). When rodent kidney cell suspensions are subjected to step-gradient fractionation immediately after isolation, the fraction enriched for tubular cells (and containing some cells from the collecting duct) segments to a density between 1.062-1.088 g/mL. In contrast, when density gradient separation was performed after ex vivo culture, the fraction enriched for tubular cells (and containing some cells from the collecting duct) segmented to a density between 1.051-1.062 g/mL. Similarly, when rodent kidney cell suspensions are subjected to step-gradient fractionation immediately after isolation, the fraction enriched for epo-producing cells, glomerular podocytes, and vascular cells ("B4") segregates at a density between 1.025-1.035 g/mL. In contrast, when density gradient separation was performed after ex vivo culture, the fraction enriched for epo-producing cells, glomerular podocytes, and vascular cells ("B4") segregated at a density between 1.073-1.091 g/mL. Importantly, the post-culture distribution of cells into both the "B2" and the "B4" fractions was enhanced by exposure (for a period of about 1 hour to a period of about 24 hours) of the cultures to a hypoxic culture environment (hypoxia being defined as <21% (atmospheric) oxygen levels prior to harvest and step-gradient procedures (additional details regarding hypoxia-effects on band distribution are provided in Example 7).

Each band was washed by diluting with 3× the volume of KSFM, mixed well, and centrifuged for 5 minutes at 300×g. Pellets were re-suspended in 2 mls of KSFM and viable cells were counted using trypan blue exclusion and a hemacytometer. 1 million cells were collected for an RNA sample, washed in PBS, and snap frozen in liquid nitrogen. The cells from B2 and B4 were used for transplantation studies into uremic and anemic female rats, generated via a two-step 5/6 nephrectomy procedure at Charles River Laboratories. Characteristics of B4 were confirmed by quantitative real-time PCR, including oxygen-regulated expression of erythropoietin and vEGF, expression of glomerular markers (nephrin, podocin), and expression of vascular markers (PECAM). Phenotype of the 'B2' fraction was confirmed via expression of E-Cadherin, N-Cadherin, and Aquaporin-2. See FIGS. 49a and 49b of Presnell et al. WO/2010/056328.

Thus, use of the step gradient strategy allows not only the enrichment for a rare population of epo-producing cells (B4), but also a means to generate relatively enriched fractions of functional tubular cells (B2) (see FIGS. 50 & 51 of Presnell et al. WO/2010/056328). The step gradient strategy also allows EPO-producing and tubular cells to be separated from red blood cells, cellular debris, and other potentially undesirable cell types, such as large cell aggregates and certain types of immune cells.

The step gradient procedure may require tuning with regard to specific densities employed to provide good separation of cellular components. The preferred approach to tuning the gradient involves 1) running a continuous density gradient where from a high density at the bottom of the gradient (16-21% Optiprep, for example) to a relatively low density at the top of the gradient (5-10%, for example). Continuous gradients can be prepared with any standard density gradient solution (Ficoll, Percoll, Sucrose, iodixanol) according to standard methods (Axis Shield). Cells of interest are loaded onto the continuous gradient and centrifuged at 800×G for 20 minutes without brake. Cells of similar size and granularity tend to segregate together in the gradients, such that the relative position in the gradient can be measured, and the specific gravity of the solution at that position also measured. Thus, subsequently, a defined step gradient can be derived that focuses isolation of particular cell populations based on their ability to transverse the density gradient under specific conditions. Such optimization may need to be employed when isolating cells from unhealthy vs. healthy tissue, or when isolating specific cells from different species. For example, optimization was conducted on both canine and human renal cell cultures, to insure that the specific B2 and B4 subpopulations that were identified in the rat were isolatable from the other species. The optimal gradient for isolation of rodent B2 and B4 subpopulations consists of (w/v) of 7%, 11%, 13%, and 16% Optiprep. The optimal gradient for isolation of canine B2 and B4 subpopulations consists of (w/v) of 7%, 10%, 11%, and 16% Optiprep. The optimal gradient for isolation of human B2 and B4 subpopulations consists of (w/v) 7%, 9%, 11%, 16%. Thus, the density range for localization of B2 and B4 from cultured rodent, canine, and human renal cells is provided in Table 2.

TABLE 2

Species Density Ranges.

| Step Gradient Band | Species Density Ranges g/ml | | |
|---|---|---|---|
| | Rodent | Canine | Human |
| B2 | 1.045-1.063 g/ml | 1.045-1.058 g/ml | 1.045-1.052 g/ml |
| B4 | 1.073-1.091 g/ml | 1.063-1.091 g/ml | 1.063-1.091 g/ml |

Figure 27:
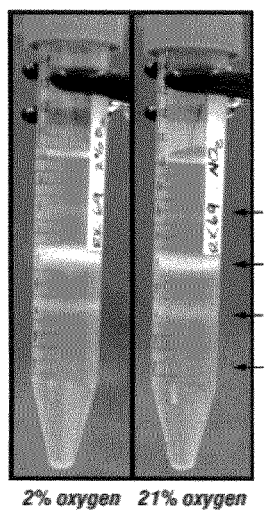
FIG. 27: shows step gradients of "normoxic" (21% oxygen) and "hypoxic" (2% oxygen) rodent cultures that were harvested separately and applied side-by-side to identical step gradients.

Example 7—Low-Oxygen Culture Prior to Gradient Affects Band Distribution, Composition, and Gene Expression To determine the effect of oxygen conditions on distribution and composition of prototypes B2 and B4, neokidney cell preparations from different species were exposed to different oxygen conditions prior to the gradient step. A rodent neo-kidney augmentation (NKA) cell preparation (RK069) was established using standard procedures for rat cell isolation and culture initiation, as described supra. All flasks were cultured for 2-3 days in 21% (atmospheric) oxygen conditions. Media was changed and half of the flasks were then relocated to an oxygen-controlled incubator set to 2% oxygen, while the remaining flasks were kept at the 21% oxygen conditions, for an additional 24 hours. Cells were then harvested from each set of conditions using standard enzymatic harvesting procedures described supra. Step gradients were prepared according to standard procedures and the "normoxic" (21% oxygen) and "hypoxic" (2% oxygen) cultures were harvested separately and applied side-by-side to identical step gradients. (FIG. 27). While 4 bands and a pellet were generated in both conditions, the distribution of the cells throughout the gradient was different in 21% and 2% oxygen-cultured batches (Table 3). Specifically, the yield of B2 was increased with hypoxia, with a concomitant decrease in B3. Furthermore, the expression of B4-specific genes (such as erythropoietin) was enhanced in the resulting gradient generated from the hypoxic-cultured cells (FIG. 73 of Presnell et al. WO/2010/056328).

Figure 28:
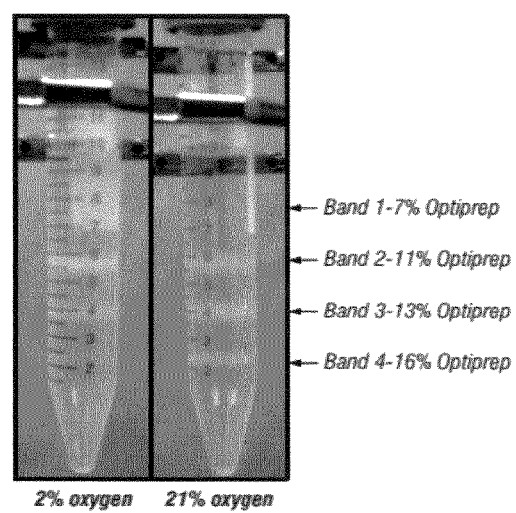
FIG. 28: shows step gradients of "normoxic" (21% oxygen) and "hypoxic" (2% oxygen) canine cultures that were harvested separately and applied side-by-side to identical step gradients.

A canine NKA cell preparation (DK008) was established using standard procedures for dog cell isolation and culture (analogous to rodent isolation and culture procedures), as described supra. All flasks were cultured for 4 days in 21% (atmospheric) oxygen conditions, then a subset of flasks were transferred to hypoxia (2%) for 24 hours while a subset of the flasks were maintained at 21%. Subsequently, each set of flasks was harvested and subjected to identical step gradients (FIG. 28). Similar to the rat results (Example 6), the hypoxic-cultured dog cells distributed throughout the gradient differently than the atmospheric oxygen-cultured dog cells (Table 3). Again, the yield of B2 was increased with hypoxic exposure prior to gradient, along with a concomitant decrease in distribution into B3.

TABLE 3

| | Rat (RK069) | | Dog (DK008) | |
|---|---|---|---|---|
| | 2% O2 | 21% O2 | 2% O2 | 21% O2 |
| B1 | 0.77% | 0.24% | 1.20% | 0.70% |
| B2 | 88.50% | 79.90% | 64.80% | 36.70% |
| B3 | 10.50% | 19.80% | 29.10% | 40.20% |
| B4 | 0.23% | 0.17% | 4.40% | 21.90% |

The above data show that pre-gradient exposure to hypoxia enhances composition of B2 as well as the distribution of specific specialized cells (erythropoietin-producing cells, vascular cells, and glomerular cells) into B4. Thus, hypoxic culture, followed by density-gradient separation as described supra, is an effective way to generate 'B2' and 'B4' cell populations, across species.

Example 8—Isolation of Tubular/Glomerular Cells from Human Kidney

Tubular and glomerular cells were isolated and propagated from normal human kidney tissue by the enzymatic isolation methods described throughout. By the gradient method described above, the tubular cell fraction was enriched ex vivo and after culture. As shown in FIG. 68 of Presnell et al. WO/2010/056328 (incorporated herein by reference in its entirety), phenotypic attributes were maintained in isolation and propagation. Tubular cell function, assessed via uptake of labeled albumin, was also retained after repeated passage and cryopreservation. FIG. 69 of Presnell et al. WO/2010/056328 (incorporated herein by reference in its entirety) shows that when tubular-enriched and tubular-depleted populations were cultured in 3D dynamic culture, a marked increase in expression of tubular marker, cadherin, was expressed in the tubular-enriched population. This confirms that the enrichment of tubular cells can be maintained beyond the initial enrichment when the cells are cultured in a 3D dynamic environment. The same cultured population of kidney cells described above in Example 7 was subjected to flow cytometric analysis to examine forward scatter and side scatter. The small, less granular EPO-producing cell population was discernable (8.15%) and was separated via positive selection of the small, less granular population using the sorting capability of a flow cytometer (see FIG. 70 of Presnell et al. WO/2010/056328 (incorporated herein by reference in its entirety)).

Example 9—Characterization of an Unfractionated Mixture of Renal Cells Isolated from an Autoimmune Glomerulonephritis Patient Sample An unfractionated mixture of renal cells was isolated, as described above, from an autoimmune glomerulonephritis patient sample. To determine the unbiased genotypic composition of specific subpopulations of renal cells isolated and expanded from kidney tissue, quantitative real time PCR (qRTPCR) analysis (Brunskill et al., supra 2008) was employed to identify differential cell-type-specific and pathway-specific gene expression patterns among the cell subfractions. As shown in Table 6.1 of Ilagan et al. PCT/US2011/036347, HK20 is an autoimmune glomerulonephritis patient sample. As shown in Table 6.2 of Hagan et al. PCT/US2011/036347, cells generated from HK20 are lacking glomerular cells, as determined by qRT-PCR.

Example 10—Genetic Profiling of Therapeutically Relevant Renal Bioactive Cell Populations Isolated from a Case of Focal Segmental Glomerulosclerosis To determine the unbiased genotypic composition of specific subpopulations of renal cells isolated and expanded from kidney tissue, quantitative real time PCR (qRTPCR) analysis (Brunskill et al., supra 2008) was employed to identify differential cell-type-specific and pathway-specific gene expression patterns among the cell subfractions. Human preparation HK023, derived from a case of focal segmental glomerulosclerosis (FSGS) in which a large portion of glomeruli had been destroyed, was evaluated for presence of glomerular cells in the B4 fraction at the time of harvest. In brief, unfractionated (UNFX) cultures were generated (Aboushwareb et al., supra 2008) and maintained independently from each of (4) core biopsies taken from the kidney using standard biopsy procedures. After (2) passages of UNFX ex vivo, cells were harvested and subjected to density gradient methods (as in Example 6) to generate subfractions, including subfraction B4, which is known to be enriched for endocrine, vascular, and glomerular cells based on work conducted in rodent, dog, and other human specimens.

The B4 fractions were collected separately from each independent UNFX sample of HK023, appearing as distinct bands of cells with buoyant density between 1.063-1.091 g/mL. RNA was isolated from each sample and examined for expression of Podocin (glomerular cell marker) and PECAM (endothelial cell marker) by quantitative real-time PCR. As expected from a biopsy-generated sample from a case of severe FSGS, the presence of podocin(+) glomerular cells in B4 fractions was inconsistent, with podocin undetectable in 2/4 of the samples. In contrast, PECAM+ vascular cells were consistently present in the B4 fractions of 4/4 of the biopsy-initiated cultures. Thus, the B4 fraction can be isolated at the 1.063-1.091 g/mL density range, even from human kidneys with severe disease states.

TABLE 4

Expression of Podocin and PECAM for detection of glomerular and vascular cells in subfraction B4 isolated from a case of FSGS.

| HK023/Biopsy | RQ (Podocin)/B4 | RQ (PECAM)/B4 |
| --- | --- | --- |
| #1/p2 | 0.188 | 0.003 |
| #2/p2 | ND | 0.02 |
| #3/p2 | 40.1 | 0.001 |
| #4/p2 | ND | 0.003 |

Further, as shown in Table 7.2 of Hagan et al. PCT/US2011/036347, human sample (HK018) displayed undetected Podocin (glomerular marker) by qRTPCR after density gradient centrifugation.

Example 11—Enrichment/Depletion of Viable Kidney Cell Types Using Fluorescent Activated Cell Sorting (FACS)

One or more isolated kidney cells may be enriched, and/or one or more specific kidney cell types may be depleted from isolated primary kidney tissue using fluorescent activated cell sorting (FACS).

Reagents:

70% ethanol; Wash buffer (PBS); 50:50 Kidney cell medium (50% DMEM high glucose): 50% Keratinocyte-SFM; Trypan Blue 0.4%; Primary antibodies to target kidney cell population such as CD31 for kidney endothelial cells and Nephrin for kidney glomerular cells. Matched isotype specific fluorescent secondary antibodies; Staining buffer (0.05% BSA in PBS)

Procedure:

Following standard procedures for cleaning the biological safety cabinet (BSC), a single cell suspension of kidney cells from either primary isolation or cultured cells may be obtained from a T500 T/C treated flask and resuspend in kidney cell medium and place on ice. Cell count and viability is then determined using trypan blue exclusion method. For kidney cell enrichment/depletion of, for example, glomerular cells or endothelial cells from a heterogeneous population, between 10 and 50e6 live cells with a viability of at least 70% are obtained. The heterogeneous population of kidney cells is then stained with primary antibody specific for target cell type at a starting concentration of 1 µg/0.1 ml of staining buffer/1×10$^6$ cells (titer if necessary). Target antibody can be conjugated such as CD31 PE (specific for kidney endothelial cells) or un-conjugated such as Nephrin (specific for kidney glomerular cells).

Cells are then stained for 30 minutes on ice or at 4° C. protected from light. After 30 minutes of incubation, cells are washed by centrifugation at 300×g for 5 min. The pellet is then resuspended in either PBS or staining buffer depending on whether a conjugated isotype specific secondary antibody is required. If cells are labeled with a fluorochrome conjugated primary antibody, cells are resuspended in 2 mls of PBS per 10e7 cells and proceed to FACS aria or equivalent cell sorter. If cells are not labeled with a fluorochrome conjugated antibody, then cells are labeled with an isotype specific fluorochrome conjugated secondary antibody at a starting concentration of 1 ug/0.1 ml/0.1 ml/1e6 cells.

Cells are then stained for 30 min. on ice or at 4° C. protected from light. After 30 minutes of incubation, cells are washed by centrifugation at 300×g for 5 min. After centrifugation, the pellet is resuspended in PBS at a concentration of 5e6/ml of PBS and then 4 mls per 12×75 mm is transferred to a sterile tube.

FACs Aria is prepared for live cell sterile sorting per manufacturer's instructions (BD FACs Aria User Manual). The sample tube is loaded into the FACs Aria and PMT voltages are adjusted after acquisition begins. The gates are drawn to select kidney specific cells types using fluorescent intensity using a specific wavelength. Another gate is drawn to select the negative population. Once the desired gates have been drawn to encapsulate the positive target population and the negative population, the cells are sorted using manufacturer's instructions.

The positive target population is collected in one 15 ml conical tube and the negative population in another 15 ml conical tube filled with 1 ml of kidney cell medium. After collection, a sample from each tube is analyzed by flow cytometry to determine purity. Collected cells are washed by centrifugation at 300×g for 5 min. and the pellet is resuspended in kidney cell medium for further analysis and experimentation.

Example 12—Enrichment/Depletion of Kidney Cell Types Using Magnetic Cell Sorting One or more isolated kidney cells may be enriched and/or one or more specific kidney cell types may be depleted from isolated primary kidney tissue.

Reagents:

70% ethanol, Wash buffer (PBS), 50:50 Kidney cell medium (50% DMEM high glucose): 50% Keratinocyte-SFM, Trypan Blue 0.4%, Running Buffer (PBS, 2 mM EDTA, 0.5% BSA), Rinsing Buffer (PBS, 2 mM EDTA), Cleaning Solution (70% v/v ethanol), Miltenyi FCR Blocking reagent, Miltenyi microbeads specific for either IgG isotype, target antibody such as CD31(PECAM) or Nephrin, or secondary antibody.

Procedure:

Following standard procedures for cleaning the biological safety cabinet (BSC), a single cell suspension of kidney cells from either primary isolation or culture is obtained and resuspended in kidney cell medium. Cell count and viability is determined using trypan blue exclusion method. For kidney cell enrichment/depletion of, for example, glomerular cells or endothelial cells from a heterogeneous population, at least 10e6 up to 4e9 live cells with a viability of at least 70% is obtained.

The best separation for enrichment/depletion approach is determined based on target cell of interest. For enrichment of a target frequency of less than 10%, for example, glomerular cells using Nephrin antibody, the Miltenyi autoMACS, or equivalent, instrument program POSSELDS (double positive selection in sensitive mode) is used. For depletion of a target frequency of greater than 10%, the Miltenyi autoMACS, or equivalent, instrument program DEPLETES (depletion in sensitive mode) is used.

Live cells are labeled with target specific primary antibody, for example, Nephrin rb polyclonal antibody for glomerular cells, by adding 1 µg/10e6 cells/0.1 ml of PBS with 0.05% BSA in a 15 ml conical centrifuge tube, followed by incubation for 15 minutes at 4° C.

After labeling, cells are washed to remove unbound primary antibody by adding 1-2 ml of buffer per 10e7 cells followed by centrifugation at 300×g for 5 min. After washing, isotype specific secondary antibody, such as chicken anti-rabbit PE at 1 ug/10e6/0.1 ml of PBS with 0.05% BSA, is added, followed by incubation for 15 minutes at 4° C.

After incubation, cells are washed to remove unbound secondary antibody by adding 1-2 ml of buffer per 10e7 cells followed by centrifugation at 300×g for 5 min. The supernatant is removed, and the cell pellet is resuspended in 60 µl of buffer per 10e7 total cells followed by addition of 20 µl of FCR blocking reagent per 10e7 total cells, which is then mixed well. Add 20 µl of direct MACS microbeads (such as anti-PE microbeads) and mix and then incubate for 15 min at 4° C.

After incubation, cells are washed by adding 10-20× the labeling volume of buffer and centrifuging the cell suspension at 300×g for 5 min. and resuspending the cell pellet in 500 µl-2 mls of buffer per 10e8 cells.

Per manufacturer's instructions, the autoMACS system is cleaned and primed in preparation for magnetic cell separation using autoMACS. New sterile collection tubes are placed under the outlet ports. The autoMACS cell separation program is chosen. For selection the POSSELDS program is chosen. For depletion the DEPLETES program is chosen.

The labeled cells are inserted at uptake port, then beginning the program. After cell selection or depletion, samples are collected and placed on ice until use. Purity of the depleted or selected sample is verified by flow cytometry.

Example 13—Cells with Therapeutic Potential can be Isolated and Propagated from Normal and Chronically-Diseased Kidney Tissue The objective of the present study was to determine the functional characterization of human NKA cells through high content analysis (HCA). High-content imaging (HCI) provides simultaneous imaging of multiple sub-cellular events using two or more fluorescent probes (multiplexing) across a number of samples. High-content Analysis (HCA) provides simultaneous quantitative measurement of multiple cellular parameters captured in High-Content Images. In brief, unfractionated (UNFX) cultures were generated (Aboushwareb et al., supra 2008) and maintained independently from core biopsies taken from five human kidneys with advanced chronic kidney disease (CKD) and three non-CKD human kidneys using standard biopsy procedures. After (2) passages of UNFX ex vivo, cells were harvested and subjected to density gradient methods (as in Example 2) to generate subfractions, including subfractions B2, B3, and/or B4.

Human kidney tissues were procured from non-CKD and CKD human donors as summarized in Table 10.1 of Hagan et al. PCT/US2011/036347. FIG. 4 of Hagan et al. PCT/US2011/036347 shows histopathologic features of the HK17 and HK19 samples. Ex vivo cultures were established from all non-CKD (3/3) and CKD (5/5) kidneys. High content analysis (HCA) of albumin transport in human NKA cells defining regions of interest (ROI) is shown in FIG. 5 (HCA of albumin transport in human NKA cells) of Ilagan et al. PCT/US2011/036347. Quantitative comparison of albumin transport in NKA cells derived from non-CKD and CKD kidney is shown in FIG. 6 of Hagan et al. PCT/US2011/036347. As shown in FIG. 6 of Hagan et al. PCT/US2011/036347, albumin transport is not compromised in CKD-derived NKA cultures. Comparative analysis of marker expression between tubular-enriched B2 and tubular cell-depleted B4 subfractions is shown in FIG. 7 (CK8/18/19) of Ilagan et al. PCT/US2011/036347.

Comparative functional analysis of albumin transport between tubular-enriched B2 and tubular cell-depleted B4 subfractions is shown in FIG. 8 of Hagan et al. PCT/US2011/036347. Subfraction B2 is enriched in proximal tubule cells and thus exhibits increased albumin-transport function.

Albumin Uptake:

Culture media of cells grown to confluency in 24-well, collagen IV plates (BD Biocoat™) was replaced for 18-24 hours with phenol red-free, serum-free, low-glucose DMEM (pr-/s-/lg DMEM) containing 1× antimycotic/antibiotic and 2 mM glutamine. Immediately prior to assay, cells were washed and incubated for 30 minutes with pr-/s-/lg DMEM+ 10 mM HEPES, 2 mM glutamine, 1.8 mM $CaCl_2$, and 1 mM MgCl2. Cells were exposed to 25 µm/mL rhodamine-conjugated bovine albumin (Invitrogen) for 30 min, washed with ice cold PBS to stop endocytosis and fixed immediately with 2% paraformaldehyde containing 25 µg/mL Hoechst nuclear dye. For inhibition experiments, 1 µM receptor-associated protein (RAP) (Ray Biotech, Inc., Norcross Ga.) was added 10 minutes prior to albumin addition. Microscopic imaging and analysis was performed with a BD Pathway™ 855 High-Content BioImager (Becton Dickinson) (see Kelley et al. Am J Physiol Renal Physiol. 2010 November; 299(5):F1026-39. Epub Sep. 8, 2010).

In conclusion, HCA yields cellular level data and can reveal populations dynamics that are undetectable by other assays, i.e., gene or protein expression. A quantifiable ex-vivo HCA assay for measuring albumin transport (HCA-AT) function can be utilized to characterize human renal tubular cells as components of human NKA prototypes. HCA-AT enabled comparative evaluation of cellular function, showing that albumin transport-competent cells were retained in NKA cultures derived from human CKD kidneys. It was also shown that specific subfractions of NKA cultures, B2 and B4, were distinct in phenotype and function, with B2 representing a tubular cell-enriched fraction with enhanced albumin transport activity. The B2 cell subpopulation from human CKD are phenotypically and functionally analogous to rodent B2 cells that demonstrated efficacy in vivo (as shown above).

Example 14—Exosomes Derived from Primary Renal Cells Contain microRNAs

We sought to correlate specific exosome-derived miRNAs with functionally-relevant outcomes in target cells in vitro to inform the design of in vivo studies for elucidating mechanisms that yield regenerative outcomes.

Figure 29:
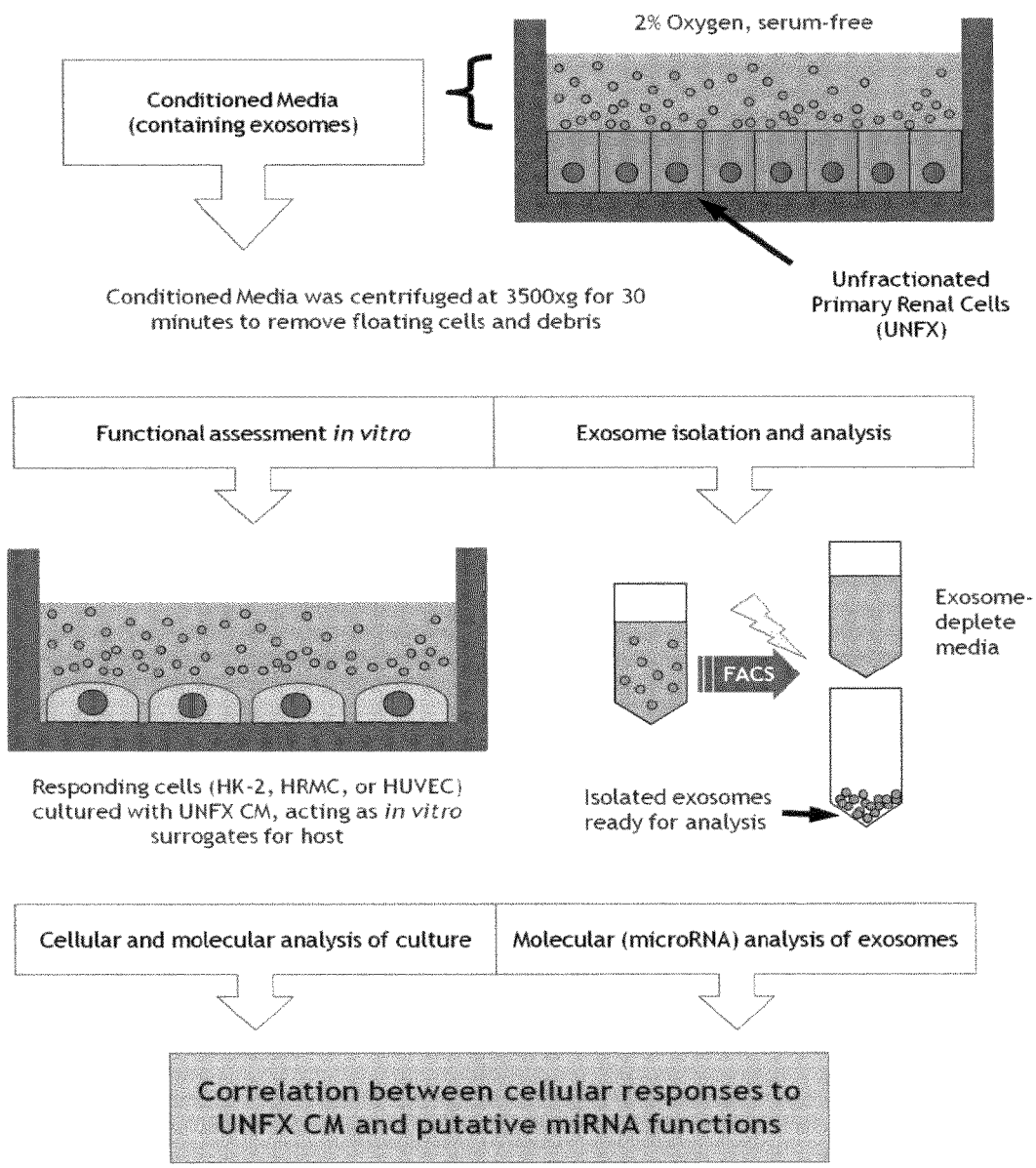
FIG. 29: provides a schematic for the preparation and analysis of UNFX conditioned media.

METHODS: The effect of conditioned media on signaling pathways associated with regenerative healing responses was investigated using commercially available cells: HK-2 (human proximal tubule cell line), primary human renal mesangial cells (HRMC), and human umbilical cord endothelial cells (HUVEC). RNA content from exosomes in conditioned media from human and rat primary renal cell cultures (UNFX) was screened by PCR-based array designed to detect known miRNAs. Low oxygen has been reported to affect exosome shedding; therefore, a group of cultures was exposed to low oxygen (2% $O_2$) for 24 hours prior to media collection. Exosomes were separated from cellular debris by FACS. FIG. 29 provides a schematic for the preparation and analysis of UNFX conditioned media.

RESULTS: UNFX-conditioned media was found to affect signaling pathways associated with regenerative healing responses; these responses were not observed in controls using non-conditioned media. Specifically, NFκB (immune response) and epithelial-to-mesenchymal transition (fibrotic response) was attenuated in HK-2 cells, PAI-1 (fibrotic response) was attenuated in HRMC cells, and angiogenesis was promoted in HUVEC. Preliminary data from PCR array screening of exosome content from UNFX-conditioned media indicates that UNFX produces exosomes containing miRNA sequences consistent with the observed responses to UNFX-conditioned media.

FIG. 13A-C of Ilagan et al. PCT/US2011/036347 shows that conditioned media from UNFX cultures affects multiple cellular processes in vitro that are potentially associated with regenerative outcomes. NFkB signaling is proposed as a key mediator of inflammatory processes in kidney diseases (Rangan et al., 2009. Front Biosci 12:3496-3522; Sanz et al., 2010. J Am Soc Nephrol 21:1254-1262), and can be activated by Tumor Necrosis Factors (TNF). HK-2 cells were preincubated with unconditioned media (left) or UNFX conditioned media (right) for 1 hour at 37° C., then activated with or without 10 ng/ml TNFa.

FIG. 13A of Ilagan et al. PCT/US2011/036347 shows that UNFX-conditioned media attenuates TNF-a mediated activation of NF-kB. NFκB activation was measured by RelA/p65 immunofluorescence staining (green). Hoechst-counterstained nuclei (blue) and phalloidin-stained filamentous actin (red) facilitate assessment of RelA/p65 nuclear localization (white arrows).

FIG. 13B of Ilagan et al. PCT/US2011/036347 shows that UNFX-conditioned media increases proangiogenic behavior of HUVEC cell cultures. HUVEC cells (100,000 per well) were overlaid onto polymerized Matrigel in Media 200 plus 0.5% BSA. Unconditioned media (left) or UNFX-conditioned medium (right) was added and cellular organizational response was monitored visually for 3-6 hours with image capture. Cellular organization was scored for cell migration (white arrowheads), alignment (black arrowheads), tubule formation (red arrowheads), and formation of closed polygons (asterisks). UNFX conditioned media induced more tubules and closed polygons compared to unconditioned media, suggesting that proangiogenic factors are present in the media.

FIG. 13C Ilagan et al. PCT/US2011/036347 shows that UNFX-conditioned media attenuates fibrosis pathways in epithelial cells. HK-2 cells lose epithelial characteristics, and acquire a mesenchymal phenotype when exposed to Transforming Growth Factors (TGF) in vitro, replicating the epithelial-to-mesenchymal transition (EMT) that is associated with progression of renal fibrosis (Zeisberg et al. 2003 Nat Med 9:964-968). HK-2 cells were cultured in unconditioned media (CTRL), unconditioned media containing 10 ng/ml TGFβ1 (TGFβ1), or UNFX conditioned media containing 10 ng/ml TGFβ1 (TGFβ1+CM) for 72 hours. Cells were assayed by quantitative RT-PCR for CDH1 (epithelial marker), CNN1 (mesenchymal marker) and MYH11 (mesenchymal marker). Conditioned media reduces the degree of TGFβ1-induced EMT as measured by CDH1, CNN1, and MYH11 gene expression. Error bars represent the standard error of the mean (SEM) of three experimental replicates.

FIG. 13D of Ilagan et al. PCT/US2011/036347 depicts the positive feedback loop established by TGFβ1 and Plasminogen Activator Inhibitor-1 (PAI-1) that, when left unchecked, can lead to the progressive accumulation of extracellular matrix proteins (Seo et al., 2009. Am J Nephrol 30:481-490).

FIG. 14A-B of Hagan et al. PCT/US2011/036347 shows the attenuation of fibrosis pathways in mesangial cells. HRMC were cultured for 24 hours in control (CTRL) or UNFX conditioned media (UNFX CM) with (+) or without (−) the addition of 5 ng/ml TGFβ1. Western blot analysis for PAI-1 demonstrates that UNFX CM attenuates the TGFβ1-induced increase in PAI-1 protein levels. bActin is shown as a loading control. Human renal mesangial cells (HRMC) express increased levels of PAI-1 in the presence (+) of 5 ng/ml TGFb1. Co-culture with conditioned media (CM) derived from human bioactive kidney cells attenuates TGFb1-induced PAI-1 protein expression. PAI-1 expression at the mRNA level was unaltered by CM (data not shown).

FIG. 14B of Ilagan et al. PCT/US2011/036347 shows that CM from rat bioactive kidney cells had similar effect on cultured HRMC induced (+) and uninduced (−) with TGFb1. CM supernatant (Deplete Rat CM) collected after centrifugation was less effective at attenuating PAI-1 expression, suggesting that the CM component responsible for the observed attenuation of PAI-1 protein might be associated with vesicles secreted by the rat bioactive kidney cells.

FIG. 15 of Ilagan et al. PCT/US2011/036347 shows that the conditioned media from UNFX contains secreted vesicles. FIG. 15A of Ilagan et al. PCT/US2011/036347 depicts secreted vesicles (including exosomes), which are bilipid structures (red) that encompass cytoplasm-derived internal components (green). Phosphatidylserines (blue triangles) are components of the membrane that are exposed to the extracellular space during vesicle biogenesis (Thery et al., 2010. *Nat Rev Immunol* 9:581-593).

PKH26 and CFSE label the lipid membrane and cytoplasm of secreted vesicles (Aliotta et al., 2010. *Exp Hematol* 38:233-245), respectively, while Annexin V binds phosphatidylserines.

FIG. 15B-C of Ilagan et al. PCT/US2011/036347 shows FACS sorting. UNFX conditioned media was labeled with PKH26, CFSE, and APC-conjugated Annexin V, then sorted by fluorescence-assisted cell sorting (FACS). Triple-positive particles, representing secreted vesicles, were collected and total RNA was extracted using TRIZol reagent. microRNA content was screened for known sequences using commercially available RT-PCR-based arrays.

Table 5 shows that secreted vesicles contain microRNAs with predicted therapeutic outcomes. UNFX cells shed exosomes that contain known miRNA sequences. UNFX-conditioned media affects functionally-relevant regenerative responses in human cell lines. The cause and effect relationship between detected miRNAs and observed regenerative responses is under active investigation; however, the results achieved to date suggest that UNFX cells have the potential to produce therapeutically-relevant paracrine effects via exosome-mediated transfer of miRNAs to target cells and tissues.

TABLE 5

| miRNA in exosomes | Gene targets | Predicted effects |
|---|---|---|
| miR-146a | TRAF6, IRAK1* | Inhibits NFkB |
| miR-130a | GAX, HOXA5** | Promotes angiogenesis |
| miR-23b | Smad 3/4/5*** | Inhibits TGFβ signal transduction (anti-fibrotic) |

*Taganov et al, 2006. Proc Natl Acad Sci USA 103: 12481-12486.
**Chen and Gorski, 2008. Blood 111: 1217-1226.
***Rogler et al., 2009. Hepatology 50: 575-584.

The data support the conclusion that excreted vesicles from bioactive renal cell cultures contain components that attenuate PAI-1 induced by the TGFb1/PAI-1 feedback loop.

Microarray and RT-PCR Analysis.

Unfractionated (UNFX) bioactive renal cells from Lewis rats were cultured in basal media (50:50 mix of DMEM and KSFM without serum or supplements) for 24 hours under low oxygen conditions (2% O2). Conditioned media was collected and ultracentrifuged at 100,000×g for 2 hours at 4 C to pellet secreted vesicles (e.g. microvesicles, exosomes). Total RNA was extracted from the resulting pellet, and assayed for known microRNA species by real time RT-PCR (Rat MicroRNA Genome V2.0 PCR Array; Qiagen #MAR-100A). The miRNAs miRNAs listed on line 26 on page 74 to line 67 on page 77 in Eagan et al. PCT/US2011/036347 were detectable.

Example 15—Paracrine Factors Derived from Bioactive Kidney Cells

In the present study, we employed in vitro cell-based assays to investigate potential paracrine mechanism(s) by which bioactive kidney cells could modulate fibrosis through mediators such as Plasminogen Activator Inhibitor-1 (PAI-1).

Materials and Methods:

Conditioned media was collected from rat and human cultures of bioactive kidney cells (Aboushwareb et al., *World J Urol* 26, 295, 2008; Presnell et al. 2010 supra) under serum- and supplement-free conditions and utilized for in vitro assays. Commercially available rat- and human-derived mesangial cells were used as surrogates for host-response tissues in the in vitro assays because mesangial cells are a source of PAI-1 production in injured or diseased kidneys (Rerolle et al., *Kidney Int* 58, 1841, 2000.). PAI-1 gene and protein expression were assayed by quantitative RT-PCR and Western blot, respectively. Vesicular particles shed by cells into the culture media (e.g., exosomes) were collected by high-speed centrifugation (Wang et al., *Nuc Acids Res* 2010, 1-12 doi:10.1093/nar/gkq601, Jul. 7, 2010) and total RNA extracted from the pellet with TRIzol reagent (Invitrogen). RNA content of the vesicles was screened using PCR-based arrays of known microRNA sequences (Qiagen).

Results:

Conditioned media from bioactive kidney cell cultures attenuated the TGFβ1-induced increase in PAI-1 steady-state protein levels in mesangial cells, but did not affect steady state mRNA levels; an observation that is consistent with the mechanism by which microRNAs modulate target genes. Based on the hypothesis that microRNAs can be transferred between cells through extracellular vesicle trafficking (Wang et al., supra 2010), we analyzed the conditioned media for microRNA content and confirmed the presence of microRNA 30b-5p (miR-30b-5p), a putative inhibitor of PAI-1.

The data presented here suggest that bioactive kidney cells may modulate fibrosis directly through cell-to-cell transfer of miR-30b-5p to target mesangial cells via exosomes. As a result of miR-30b-5p uptake by mesangial cells, TGFβ1-induced increases in steady-state PAI-1 protein levels are attenuated, a response that, in renal tissue, could ultimately reduce deposition of extracellular matrix within the glomerular space. Current work is underway to confirm that PAI-1 is indeed a direct target of miR-30b-5p.

FIG. 14A-B of Hagan et al. PCT/US2011/036347 shows a western blot of PAI-1 and α-Actin (control) protein expression in human mesangial cells cultured for 24 hour in control (CTRL) or bioactive kidney cell conditioned media (CM) with (+) or without (−) TGFβ1 addition to the culture media. In CTRL cultures, TGFβ1 increased PAI-1 protein expression. In CM cultures, the TGFβ1-induced response was attenuated.

Secreted vesicles were analyzed for microRNAs that may be putative repressors of PAI-1. Secreted vesicles from human and rat bioactive kidney cell CM were collected by high-speed centrifugation and assayed for microRNA content using PCR-based arrays of known sequences. miR-449a, a putative regulator of PAI-1 (6), was identified. HRMC were transiently transfected with miR-449a or not (CTRL). 24 hours post-transfection cells were either exposed to 5 ng/ml TGFb1 (+) or not (−) for an additional 24 hours.

FIG. 16A of Ilagan et al. PCT/US2011/036347 shows a Western blot in which total protein was prepared and assayed for PAI-1 and bActin. miR-449a reduced steady-state PAI-1 protein levels (compare lane 1 to lane 3) and induced levels of PAI-1 protein were also lower in miR-449a transfected cultures (compare lane 2 to lane 4). The data support the conclusion that excreted vesicles contain miR-449a and uptake of miR-449a into mesangial cells reduces PAI-1 expression.

FIG. 16B of Ilagan et al. PCT/US2011/036347 depicts the microRNA, miR-30b-5p, which was also identified in the PCR-based array and is a putative regulator of PAI-1 based on predictive algorithms (http://mirbase.org—miRBase is hosted and maintained in the Faculty of Life Sciences at the University of Manchester).

PAI-1 protein levels in glomeruli were examined in vivo after treatment of CKD induced by 5/6 nephrectomy with bioactive renal cells.

FIG. 17A-C of Ilagan et al. PCT/US2011/036347 shows representative immunohistochemistry images of PAI-1 (A-C) in Lewis rat kidneys that have undergone unilateral nephrectomy (A), 5/6 nephrectomy (B), or 5/6 nephrectomy with intra-renal delivery of bioactive kidney cells (C). Accumulation of PAI-1 in the glomerulus (arrowheads) as a result of the 5/6 nephrectomy procedure (B) was reduced as a result of treatment (C).

In a separate study, qRT-PCR was conducted on kidney tissue harvested at necropsy and the relative gene expression values were plotted against days on study.

FIG. 17D of Ilagan et al. PCT/US2011/036347 shows that 5/6 nephrectomized rats (red squares) demonstrated more robust expression of PAI-1 relative to those treated with bioactive renal cells (blue diamonds) and sham-operated controls (green triangles).

FIG. 17E of Hagan et al. PCT/US2011/036347 shows representative Western blot analysis on kidney samples taken at 3 and 6 months post-treatment. Treated tissues (Nx+Tx) of 5/6 nephrectomized rats (Nx) had reduced the accumulation of PAI-1 and Fibronectin (FN) protein (Kelley et al. 2010 supra).

The data support the conclusion that in vivo PAI-1 protein levels in glomeruli decrease after treatment of CKD induced by 5/6 nephrectomy with bioactive renal cells. When taken together, Examples 15-16 support the hypothesis that one mechanism by which intra-renal delivery of bioactive kidney cells improves renal function might be via cell-cell transfer of components that modulate fibrotic pathways in resident kidney cells.

Example 16—Secreted Factors from Bioactive Kidney Cells Attenuate NFκB Signaling Pathways In this study, we investigated the role of NFκB pathways in the NKA-mediated attenuation of disease progression in the 5/6 nephrectomy model and to identify properties of the bioactive kidney cells that may contribute to regenerative outcomes through direct modulation of NFκB activation. FIG. 17G of Ilagan et al. PCT/US2011/036347 depicts the canonical activation of the NFκB pathway by TNFα.

Materials and Methods:

Remnant kidneys were harvested from Lewis rats in which a two-step 5/6 nephrectomy procedure was performed 6 weeks prior to being treated with B2+B4 in PBS (NKA prototype). NKA-treated (TX) or untreated (UNTX) tissues were assayed for NFκB activation by immunohistochemistry, RT-PCR, Western blot analysis, and electrophoresis mobility shift assays (EMSA). Conditioned media (CM) collected from ex vivo NKA cell cultures grown in serum- and supplement-free media was used for in vitro functional assays. The human proximal tubule cell line (HK-2) was used as target cell type for molecular and immunofluorsence-based assay readouts. Vesicular particles shed by cells into the culture media (exosomes) were collected by high-speed centrifugation. Total RNA isolated from exosomes was screened using PCR-based arrays of known microRNA sequences (Qiagen).

Results:

Nuclear localization of the NFκB subunit, RelA/p65, was observed in remnant kidneys from 5/6 nephrectomized rats, suggesting activation of inflammatory pathways in UNTX tissues. Preliminary comparison with TX tissues by RT-PCR showed a decrease in RelA gene expression, suggesting that NKA treatment may influence NFκB pathway activation through inhibition of RelA/p65 expression. This hypothesis is supported by the observation that CM attenuates TNFα-induced NFκB activation in vitro, as evidenced by the reduced nuclear localization of RelA/p65 in CM-exposed HK-2 cells (FIG. 17F of Ilagan et al. PCT/US2011/036347) relative to that seen in response to Tumor Necrosis Factor-α (TNF α). Ongoing RT-PCR analyses of NKA exosome microRNAs are investigating whether sequences known to influence NFκB pathways are present.

FIG. 17F of Ilagan et al. PCT/US2011/036347 shows a 2-hour exposure to NKA CM reduces nuclear localization of NFκB p65 (green) in HK-2 compared to that observed in control cultures pretreated with TNFα in immunofluorescent assays. In HK-2, NFκB p65 (green) localizes to the nucleus after a 30 minute exposure to TNFα (Control Media). However, pre-treatment of HK-2 cells with NKA Conditioned Media for 2 hours prior to TNFα addition attenuated the NFκB p65 nuclear localization response. Nuclei are stained with DAPI (blue) and filamentous actin is stained with Alexa594-phalloidin (red) to assist in qualitatively assessing the robustness of NFκB nuclear localization (note the slightly diminished phalloidin borders in TNFα-treated control cells in the merged panels in the bottom row). The counterstaining provide reference for the NFkB localization in the merged images.

Immunohistochemistry for the NFκB p65 subunit in kidney tissues of Lewis rats reveals that animals with progressive CKD initiated by 5/6 nephrectomy (panel B) have more robust nuclear localization of NFkB p65 subunit, particularly in tubular epithelial cells (black arrowheads) relative to the non-progressive renal insufficiency initiated by unilateral nephrectomy in control animals (panel A). Tissues harvested six weeks post-nephrectomy. Magnification at 200×.

Panel C: Western blot analysis for NFkB p65 in the cytoplasmic ('C') and nuclear ('N') protein extracts of Lewis rat kidney tissue that have undergone the 5/6 nephrectomy. Comparing weeks 1 and 13, where gtubulin levels (loading control) are relatively consistent, nuclear NFkB p65 increases over time, consistent with the immunohistochemistry results.

Panel D: Electrophoretic mobility shift assay (EMSA) on nuclear extracts confirms that the NFkB that localizes to the nucleus following 5/6 nephrectomy is activated for DNA binding. Lanes represent nuclear extracts prepared from two animals at each time point.

The NFkB pathway is progressively activated in the 5/6 nephrectomy model of chronic kidney disease. Immunohistochemistry for the NFkB p65 subunit in kidney tissues of Lewis rats was performed.

FIG. 18A-D of Ilagan et al. PCT/US2011/036347 reveals that animals with progressive CKD initiated by 5/6 nephrectomy (panel B) have more robust nuclear localization of NFkB p65 subunit, particularly in tubular epithelial cells (black arrowheads) relative to the non-progressive renal insufficiency initiated by unilateral nephrectomy in control animals (panel A). Tissues harvested six weeks post-nephrectomy. Magnification at 200×.

FIG. 18C of Hagan et al. PCT/US2011/036347 shows Western blot analysis for NFkB p65 in the cytoplasmic ('C') and nuclear ('N') protein extracts of Lewis rat kidney tissue that have undergone the 5/6 nephrectomy. Comparing weeks 1 and 13, where gtubulin levels (loading control) are relatively consistent, nuclear NFkB p65 increases over time, consistent with the immunohistochemistry results.

FIG. 18D of Ilagan et al. PCT/US2011/036347 shows an electrophoretic mobility shift assay (EMSA) on nuclear extracts and confirms that the NFkB that localizes to the nucleus following 5/6 nephrectomy is activated for DNA binding. Lanes represent nuclear extracts prepared from two animals at each time point. 1 mg of nuclear protein was incubated with 5 ng of NFkB DNA binding site, electrophoresed on a 6% DNA retardation gel, then subsequently stained with ethidium bromide.

Intra-Renal Delivery of NKA Cells Reduces NFkB Nuclear Localization.

Multiple defined subpopulations of renal cells have been isolated and assayed in vivo for bioactivity in improving renal function in the 5/6 nephrectomy model of CKD (Presnell et al. 2010 supra). NKA cells demonstrated bioactivity whereas other subpopulations did not (Kelley et al. 2010 supra).

FIG. 18E of Ilagan et al. PCT/US2011/036347 shows that Lewis rats with established CKD that received intra-renal injection of NKA (A) or non-bioactive renal cells (B). Lewis rats with established CKD received intra-renal injection of NKA (A) or non-bioactive renal cells (B). At 6 months post-treatment, tissues were harvested and assayed by immunohistochemistry for the NFkB p65 subunit. Tissues from NKA-treated animals exhibited less nuclear localization of NFkB p65, particularly in the proximal tubules, compared to tissues from animals treated with non-bioactive renal cells, suggesting that the NKA treatment participated in attenuating the NFkB pathway activity in vivo.

Analysis of microRNA content of secreted vesicles isolated from human and rat NKA conditioned media by high-speed centrifugation using PCR-based arrays of known sequences identified several microRNA species that may influence immune responses via NFkB based on literature reports (Marquez R T et al. (2010) *Am J Physiol Gastrointest Liver Physiol* 298:G535; Taganov K D et al. (2006) *Proc Natl Acad Sci USA* 103:12481) or predictive algorithms (http://mirbase.org—miRBase is hosted and maintained in the Faculty of Life Sciences at the University of Manchester).

| microRNA in vesicles | Target mRNA |
| --- | --- |
| miR-21 | Pellino-1 (Marquez et al.) |
| miR-146a | IRAK1, TRAF6 (Taganov et al.) |
| miR-124, miR-151 | NFKB/RelA (miRBase) |

The in vivo and in vitro findings provide insight on how bioactive kidney cells (NKA) might improve renal function in chronically-diseased kidneys by modulating immune response pathways such as those affected by NFkB activation. Activated NFkB (p65 nuclear localization, particularly in proximal tubule cells) is associated with the establishment of chronic kidney disease in the 5/6 nephrectomy rodent model and was attenuated by NKA treatment. The in vitro response of proximal tubule cells (HK-2) to NKA conditioned medium mimics the in vivo attenuation of NFkB nuclear localization in response to NKA treatment. Putative mediators of cell-cell inhibition of NFkB activation (microRNAs) were identified in NKA conditioned medium. Taken together, these data support the hypothesis that one mechanism by which intra-renal delivery of bioactive kidney cells improves renal function might be via cell-cell transfer of components, e.g., RNA, that modulate immune responses in resident kidney cells.

Example 17—Functional Evaluation of NKA Constructs

Renal cell populations seeded onto gelatin or HA-based hydrogels were viable and maintained a tubular epithelial functional phenotype during an in vitro maturation of 3 days as measured by transcriptomic, proteomic, secretomic and confocal immunofluorescence assays. To investigate a potential mechanism by which NKA Constructs could impact a disease state, the effect of conditioned media on TGF-β signaling pathways related to tubulo-interstitial fibrosis associated with CKD progression was evaluated. Conditioned medium was observed to attenuate TGF-β-induced epithelial-mesenchymal transition (EMT) in vitro in a human proximal tubular cell line (HK2). The materials and methods are described in Hagan et al. PCT/US2011/036347 (Example 15)

Analysis of TGF-β Mediated EMT in HK2 Cells.

HK2 cells (ATCC) were cultured in 50:50 media in fibronectin or collagen (IV) coated culture dishes (BD Biosciences). For EMT assays, HK2 cells were seeded in 24-well collagen (IV) coated plates at 70-80% confluency with 50:50 media or conditioned media collected from either two dimensional (2D) human UNFX cultures or NKA Constructs made with human UNFX that were matured for 3 days prior to media collection. TGF-β induction was initiated by adding 10 ng/ml to the culture media 3 days prior to isolating RNA from the cells for the EMT assay. EMT was monitored by qRT-PCR by analyzing the relative expression of E-cadherin (an epithelial marker) and calponin (mesenchymal marker) at the end of the three day incubation period. RNA was prepared from harvested HK2 cells for TaqMan qRT-PCR analysis as described above. Statistical analysis was done using standard two tailed Student's t-test assuming equal variance for each sample. Confidence intervals of 95% (p-value <0.05) and 99% (p-value <0.01) were used to determine statistical significance.

Results:

Effect of conditioned media from NKA Constructs on TGF-β induced EMT in HK2 cells. The development of tubulo-interstitial fibrosis during the progression of CKD is associated with TGF-β mediated EMT of tubular epithelial cells (Zeisberg et al. Am J Pathol 160(6):2001-2008; 2002). Also, attenuation of TGF-β pathways was observed in vivo in a rodent model of progressive CKD where survival was extended and renal function improved by treatment with UNFX and B2 cells (Presnell et al. WO/2010/056328). The human proximal tubular cell line HK2 has been well established as an in vitro model system to test the stimulatory or inhibitory effects of small molecules or proteins on TGF-β induced EMT (Dudas et al. Nephrol Dial Transplant 24(5): 1406-1416; 2009; Hills et al. Am J Physiol Renal Physiol 296(3):F614-621; 2009). To investigate a potential mechanism by which NKA Constructs might affect renal tissue responses post-implantation, conditioned medium collected from NKA Constructs produced with UNFX cells and hydrogel was evaluated in the HK2 EMT assay system.

Figure 26:
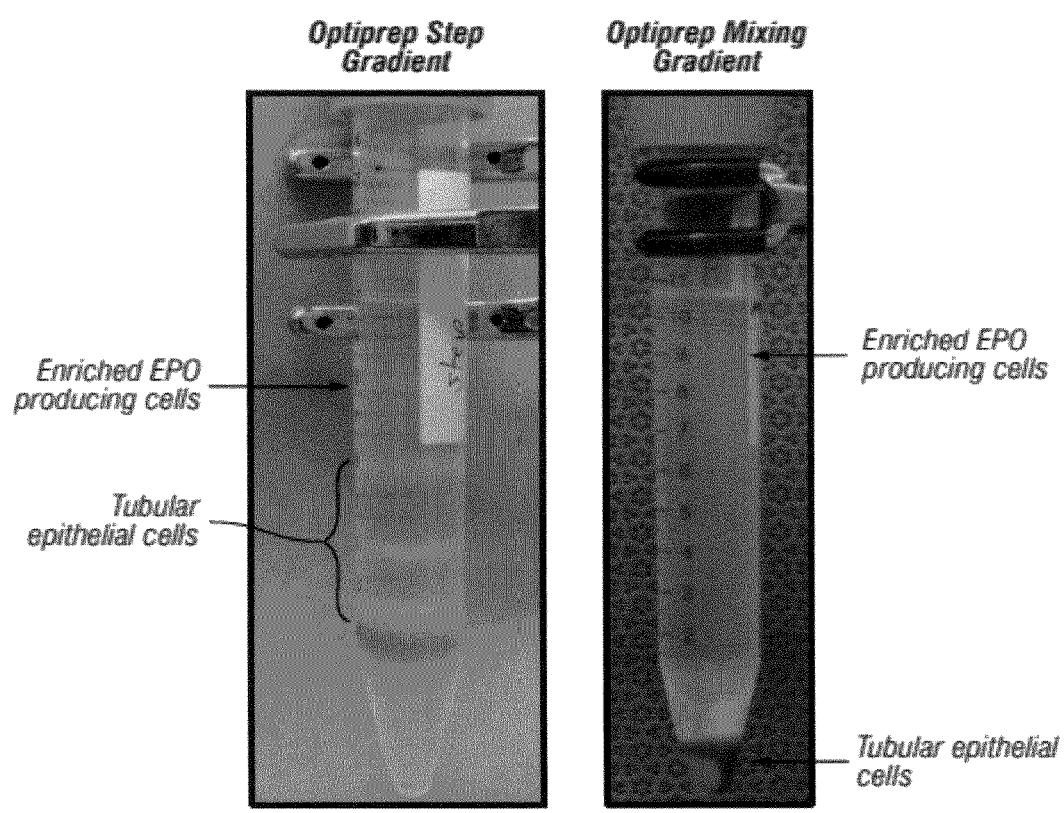
FIG. 26: shows enrichment of epo-producing cell fraction from freshly-dissociated kidney tissue using a multi-layered step gradient technique (left panel) or a single-layer mixing gradient technique (right panel). Both methods result in the partial depletion of non epo-producing cell components (predominantly tubular cells) from the epo band, which appears between 1.025 g/mL and 1.035 g/mL.

FIG. 26 of Hagan et al. PCT/US2011/036347 shows conditioned medium from NKA Constructs attenuates TGF-β induced EMT in HK2 cells in vitro. EMT is monitored by quantitating the relative expression of ECAD (epithelial) and CNN1 (mesenchymal) markers. HK2 cells were cultured in 50:50 media (Control and TGFB Control samples) or conditioned medium (CM) from 2D cultures of human UNFX cells (TC) or NKA Constructs produced from human UNFX cells and either Gelatin or HA/Gelatin as indicated. To induce EMT, 10 ng/ml TGF-β was added to each sample (except Control) for 3 days prior to assay. When HK2 cells were cultured in 50:50 media (Control), ECAD (epithelial marker) was expressed at higher levels than CNN1 (mesenchymal marker). When TGF-β is added to the media for 3 days (TGFB Control), ECAD expression was significantly down-regulated with a concomitant up-regulation of CNN1, consistent with induction of an EMT event. Conditioned medium from 2D UNFX cell cultures significantly ($p<0.05$ for both ECAD and CNN1) attenuated the EMT response of HK2 cells to TGF-β (TC CM). Conditioned medium from NKA Constructs (Gelatin CM and HA/Gelatin CM) also attenuated the EMT response to TGF-β; however the overall effect was less than that observed with conditioned medium from 2D UNFX cell cultures (significant—$p<0.05$—for ECAD with both NKA Constructs and trending toward control though not statistically significant for CNN1). Additional mesenchymal markers were screened and yielded similar results (data not shown). These data suggest that NKA Constructs could potentially affect TGF-β pathways associated with tubulointerstitial fibrosis in vivo in a manner similar to that observed with cell-based treatment (Presnell et al. WO/2010/056328). These data also suggest that the in vitro EMT assay has potential application for screening/optimizing/monitoring the biotherapeutic efficacy of NKA Constructs if in vivo responses can be demonstrated to have a statistically significant association with in vitro EMT responses, thereby potentially reducing the need for time consuming and expensive in vivo assays.

Example 18—Hypoxic Exposure of Cultured Human Renal Cells Induces Mediators of Cell Migration and Attachment and Facilitates the Repair of Tubular Cell Monolayers In Vitro The role of oxygen tension in the isolation and function of a selected population of renal epithelial cells (B2) with demonstrated therapeutic function in models of chronic kidney disease (CKD) was investigated. This study examined whether low oxygen exposure during processing alters composition and function of selected human selected renal cells (SRCs) or bioactive renal cells (BRCs). Upon exposure to 2% Oxygen, the following was observed: an alteration of the distribution of cells across a density gradient (see Presnell et al. WO 10/056,328 incorporated herein by reference in its entirety), improvement in overall post-gradient yield, modulation of oxygen-regulated gene expression (previously reported in Kelley et al. supra (2010)), increased expression of erythropoietin, VEGF, HIF1-alpha, and KDR (VEGFR2). In-process exposure to low oxygen enhances the ability of selected bioactive renal cells to repair/regenerate damaged renal tubules.

FIG. 27 of Eagan et al. PCT/US2011/036347 depicts the procedure for exposing cells to low oxygen during processing. FIG. 28 of Ilagan et al. PCT/US2011/036347 shows that upon exposure to 2% Oxygen, the following was observed: alters distribution of cells across a density gradient, improves overall post-gradient yield. Hypoxic exposure (<3%) increased recovery of cultured human CKD-derived renal cells from iodixanol-based density gradients relative to atmospheric oxygen tension (21%) (96% vs. 74%) and increased the relative distribution of selected cells (B2) into high-density (>9% iodixanol) fractions (21.6% vs. 11.2%).

Competitive in vitro assays demonstrated that B2 cells pre-exposed for 24 hours to hypoxic conditions were more proficient in repairing damaged renal proximal tubular monolayer cultures than B2 cells cultured at 21% oxygen tension, with 58.6%±3% of the repair occurring within two hours of injury.

FIG. 29A of Ilagan et al. PCT/US2011/036347 depicts an assay developed to observe repair of tubular monolayers in vitro. 1. Cells are labeled with fluorescent dyes (2% oxygen, 21% oxygen, and HK2 tubular cells). 2. The tubular cell monolayer was established and wounded. 3. Oxygen-exposed labeled cells are added (2% and 21% exposed cells). They are seeded equally at 20,000/cm2. Culturing is in serum-free media at 5% O2 for 24 hrs. 4. Cells that repair wounding are quantified. FIG. 29B—Quantitative Image Analysis (BD Pathway 855 BioImager)—red circles=cells cultured 2% O2, blue circles=21% O2. FIG. 29C—it was observed that 2% oxygen-induced cells attached more rapidly (2 hrs) and sustained a mild advantage for 24 hrs. Cells induced with 2% oxygen were more proficient at repair of tubular epithelial monolayers.

Figure 30:
FIG. 30A-B methods of preparing cellular aggregates. A—Orbital Roatator with low bind plates; B—spinner flasks with cells.
Figure 30:

FIG. 30A of Ilagan et al. PCT/US2011/036347 depicts an assay developed to observe repair of tubular monolayers in vitro. 1. Cells were labeled with fluorescent dyes. 2. The tubular cell monolayer was established on the bottom of 8 μm pore size transwell inserts and wounded. 3. The inserts are flipped and oxygen-exposed labeled cells are added (2% and 21% exposed cells). They are seeded equally at 50,000/cm2. Culturing is in serum-free media at 5% O2 for 24 hrs. 4. Cells that repair wounding are quantified.

FIG. 30B of Ilagan et al. PCT/US2011/036347 shows that the induction of cells with 2% Oxygen enhanced the migration and wound repair compared to un-induced (21% oxygen). FIG. 30C plots the % of migrated cells against the migration time. The average number of cells and average percentage of cells are provided in Table 6.

Hypoxia also induced mRNA expression of CXCR4, MMP9, ICAM1, and dystroglycan; genes that mediate cell migration and attachment. Focal accumulation of MMP9 and an increase in Connexin 43 aggregates on the cells' plasma membrane was confirmed by immunocytochemistry.

FIG. 31A of Hagan et al. PCT/US2011/036347 shows that osteopontin is secreted by tubular cells and is upregulated in response to injury (Osteopontin Immunocytochemistry: Hoechst nuclear stain (blue), Osteopontin (Red), 10×). Osteopontin is a secreted phosphorylated glycoprotein (Kelly et al. J Am Soc Soc Nephrol, 1999). Osteopontin is expressed in kidney tubules and is involved in adhesion and migration. Osteopontin is upregulated by injury in established tubular cell monolayers as shown by immunofluorescence (FIG. 31A of Hagan et al. PCT/US2011/036347) and ELISA (FIG. 31B of Hagan et al. PCT/US2011/036347).

TABLE 6

|  | 3 hr | | 24 hr | |
| --- | --- | --- | --- | --- |
| N = 3 | Average # cells | Average % | Average # cells | Average % |
| 2% O$_2$ | 26.33 | 61.51% | 117.67 | 60.35% |
| 21% O$_2$ | 16.67 | 38.49% | 76.33 | 39.65% |

Quantitative image analysis using Simple PCI

Figure 32:
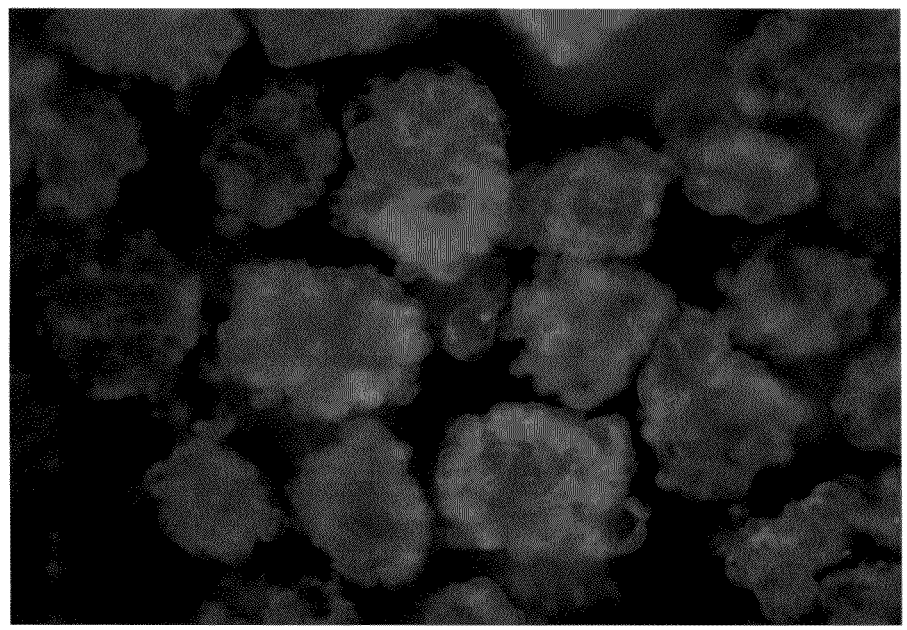
FIG. 32 depicts cellular aggregates—NKCC2 green; nucleus—blue.

FIG. 32A of Ilagan et al. PCT/US2011/036347 shows that the migratory response of cells is mediated in part by osteopontin (Green=migrated cells (5×)). FIG. 32B of Ilagan et al. PCT/US2011/036347 shows that neutralizing antibodies (NAb) to osteopontin reduce renal cell migration response by 50%.

Figure 33:
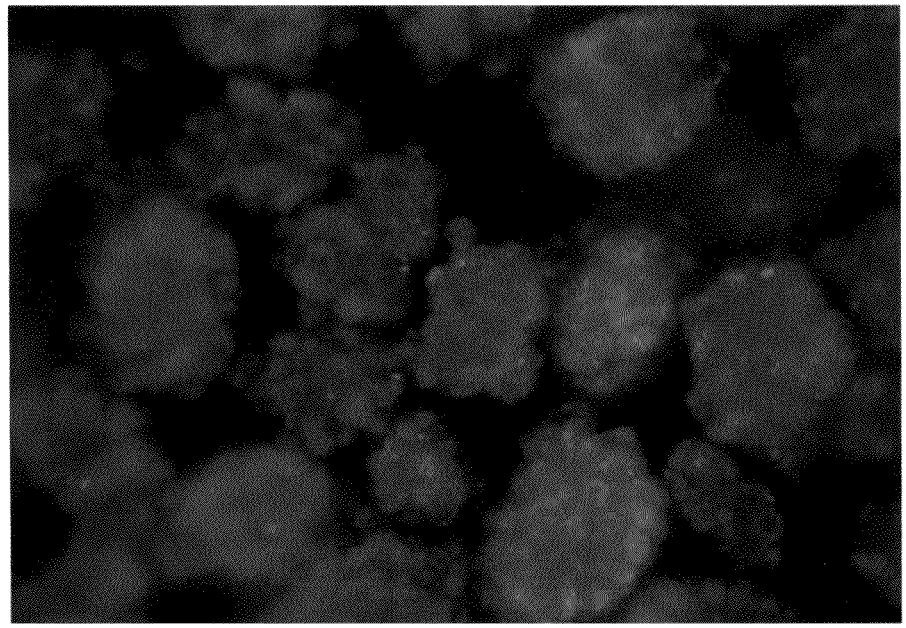
FIG. 33 depicts cellular aggregates—GGT-1 green; nucleus—blue.

FIG. 33 of Hagan et al. PCT/US2011/036347 shows that low-oxygen induction of cells modulates expression of tissue remodeling genes. Caveolin 1 is a scaffolding protein involved in modulation of integrin signaling. MMP9 is a metalloproteinase that facilitates migration through extracellular matrix degradation. ICAM1 is an intercellular adhesion molecule associated with epithelial cell motility. CXCR4 is a chemokine surface receptor that mediates cell migration.

Figure 34:
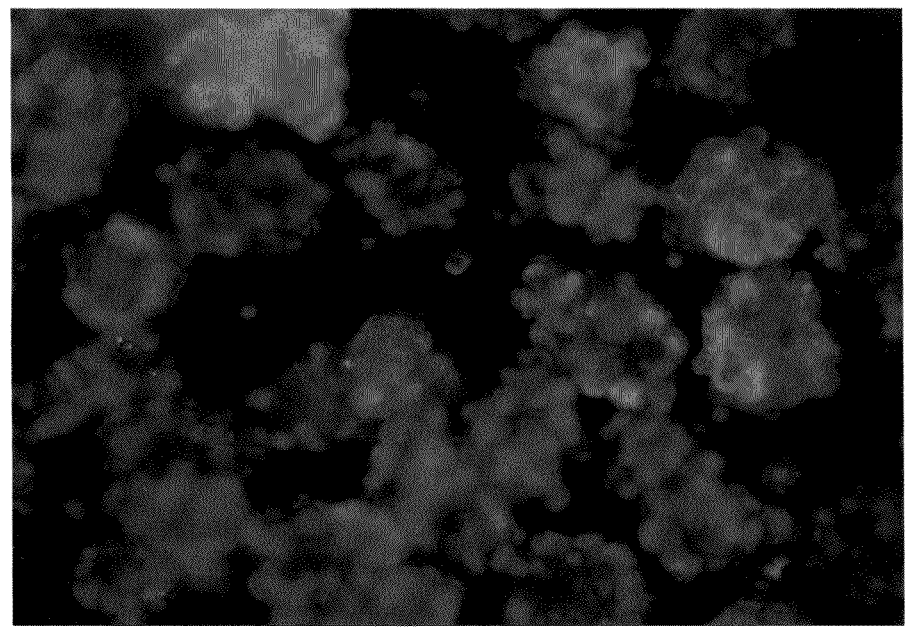
FIG. 34 depicts cellular aggregates—Aquaporin1 green; nucleus—blue.

FIG. 34 of Ilagan et al. PCT/US2011/036347 depicts a putative mechanism for low oxygen augmentation of bioactivity of cells leading to renal regeneration.

Taken together, these results suggest that hypoxic exposure facilitates the isolation of a specific renal cell subpopulation with demonstrated bioactivity for repair of tubular injury in vitro, and thus may potentially enhance the ability of these cells to migrate and engraft into diseased tissue after in vivo delivery. The SRCs demonstrated the ability to stabilize renal function and enhance survival in a rodent model of progressive CKD. The low oxygen levels (2% O2) provided the following: enhanced post-culture recovery of selected regenerative cells; enhanced cellular attachment and monolayer repair in response to tubular injury; and stimulated cellular migration in response to tubular injury. In addition, cellular migration and attachment were mediated in part by osteopontin in vitro, low-oxygen upregulated integrins, secreted proteins, and cell adhesion molecules which mediate tissue remodeling, migration, and cell-cell communication.

Example 19—Urine-Derived Microvesicles

An analysis of the miRNAs and proteins contained within the luminal contents of kidney derived microvesicles shed into the urine was performed to determine whether they might be used as biomarkers for assessing regenerative outcome. As excess microvesicles are shed into the extracellular space, some fuse with neighboring cells while others are excreted into the urine (Thou et al. 2008. Kidney Int. 74(5):613-621). These urinary microvesicles now become excellent biomarkers for assay development in order to better understand treatment outcomes.

Figure 35:
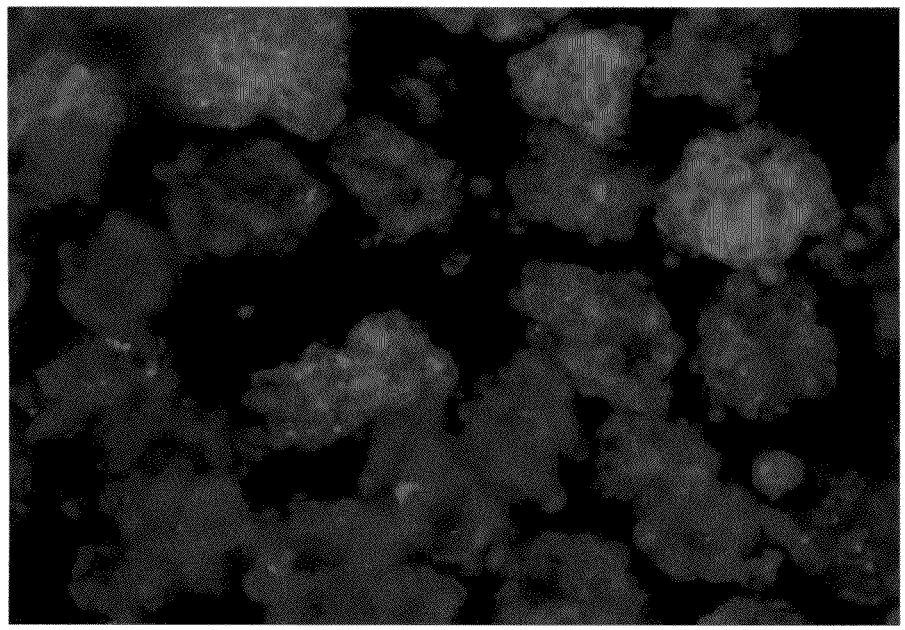
FIG. 35 depicts cellular aggregates—Leucine Aminopeptidase 3 red; nucleus blue.

The ZSF1 rodent model of metabolic disease with chronic progressive renal failure was used. B2+B4 cells were injected into the renal parenchyma of ZSF1 animals. Healthy animals and PBS vehicle were used as controls. Urine-derived vesicles were analyzed at different time points as summarized below.
1: ZSF1 animal—PBS vehicle injected; urine collected 197 days after injection
2: ZSF1 animal—PBS vehicle injection; urine collected 253 days after injection
3: ZSF1 animal—B2+B4 fraction injected; urine collected 197 days after injection
4: ZSF1 animal—B2+B4 fraction injected; urine collected 253 days after injection
5. ZSF1 animal—no injection; urine collected on day 197 of the study
6. ZSF1 animal—no injection; urine collected on day 253 of the study
7. Healthy animal—no injection; urine collected on day 197 of the study
8. Healthy animal—no injection; urine collected on day 253 of the study Urine was collected from the test animals on day 197 and about 253 days after treatment. Microvesicles were recovered from the urine by standard methods known in the art (for example, see Thou et al. Kidney Int. 2008 September; 74(5): 613-621). As shown by standard Western blotting in FIG. 35 of Ilagan et al. PCT/US2011/036347, microvesicles recovered from the urine of treated animals (lanes 3-4) showed an increase in proteins associated with progenitor cells (CD133 & WNT7A) when compared to either vehicle treated (lanes 1-2) or untreated controls (lanes 5-8). In fact, microvesicles were only recovered from the urine of diseased animals (lanes 1-6), not healthy controls (lanes 7-8), as indicated by expression of the microvesicle specific protein CD63 (FIG. 35 of Ilagan et al. PCT/US2011/036347). The CD133-containing microvesicles appear to be prominosomes shed from kidney cells. Both CD133 and WNT7A have been associated with regeneration and stem cell division (Romagnani P and Kalluri R. 2009. Fibrogenesis Tissue Repair. 2(1):3; Lie et al. 2005. Nature. 437 (7063):1370-5; Willert et al. 2003. Nature. 423(6938):448-52; Li et al. 2009. Am J Physiol Renal Physiol. 297(6): F1526-33). Taken together, this supports targeting proteins expressed in microvesicles as biomarkers for assay development designed to monitor regeneration.

miRNA Microarrays and RT-PCR.

Microarray and RT-PCR analysis of miRNA from urine-derived vesicles was performed by standard methods known in the art (for example, see Wang et al. supra 2010). In addition to proteins, miRNAs were found within the contents of the isolated microvesicles. Table 17.1 of Ilagan et al. PCT/US2011/036347 provides examples of miRNAs that were found to be increased with treatment. The change in miRNA was analyzed in ZSF1 animals treated with B2+B4 over time (day 197 and day 253). A fold change was observed for the miRNAs listed from line 1 on page 98 to line 50 on page 100 in Hagan et al. PCT/US2011/036347. miRNA levels were analyzed in ZSF1 animals treated with B2+B4 (day 253) and compared to the miRNA levels in ZSF1 animals treated with PBS vehicle (day 253). A fold change was observed for the miRNAs listed on line 53 on page 100 to line 7 on page 103 in Ilagan et al. PCT/US2011/036347. miRNA levels were analyzed in ZSF1 animals treated with B2+B4 (day 197) and compared to the miRNA levels in ZSF1 animals treated with PBS vehicle (day 197). A fold change was observed for the miRNAs listed on line 12 on page 103 to line 10 on page 105 in Ilagan et al. PCT/US2011/036347.

The miRNAs listed in Table 17.1 of Hagan et al. PCT/US2011/036347 provide examples of miRNAs that have been implicated in processes relative to tissue regeneration. miR-15b has been implicated in regulating apoptosis through BCL-2 and caspase regulation (Guo et al. 2009. J Hepatol. 50(4):766-78) as well as cell cycle progression through the regulation of cyclins (Xia et al. 2009. Biochem Biophys Res Commun. 380(2):205-10). miR-21 was shown to inhibit apoptosis by modulating survival pathways MAPK/ERK. The miR-30 family of miRNAs is critical for podocyte structure and function suggesting that an increase maybe necessary for glomerulargenisis. miR-141, 200a, 200c and 429 are all involved in modulating epithelial to mesenchymal transition (EMT) in response to TGF-β signaling possibly reducing fibrosis (Saal et al. 2009. Curr. Opin. Nephrol. Hypertens. 18:317-323). miR-146a and 151 have been implicated in NFκB modulation thus potentially reducing the inflammatory response in vivo (
Taganov et al. 2006. Proc Natl Acad Sci USA. 103(33): 12481-6; Griffiths-Jones et al. 2006. NAR. 34 Database Issue: D140-D144). Collectively, these miRNAs regulate processes related to a successful regenerative outcome; thus making them candidate biomarkers for assay development.

Overall, this data supports the concept that urinary microvesicles and/or their luminal contents are viable targets for regenerative assays as they contain proteins and miRNAs capable of modulating multiple pathways including: TGFβ-1, NFκB, apoptosis, cell division and pluripotency in addition to providing practitioners with a non-invasive means of monitoring treatment.

Example 20—Methods of Preparing Human Kidney Cellular Aggregates

Figure 31:
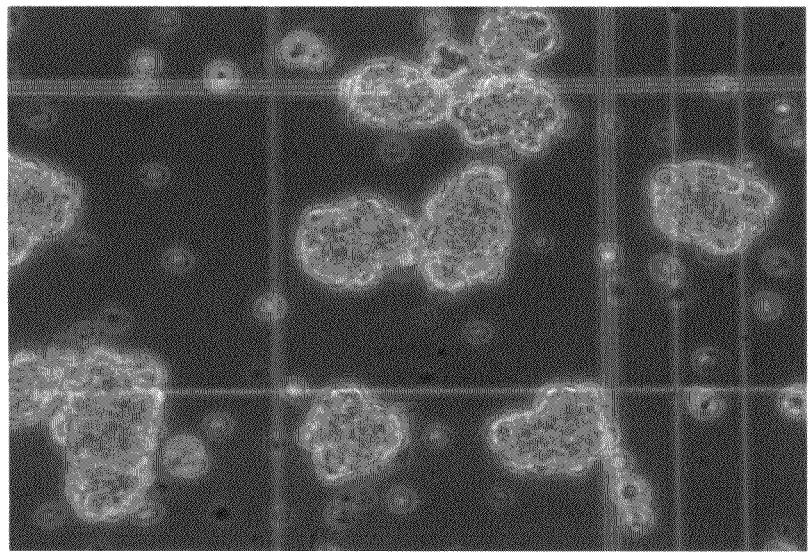
FIG. 31 depicts cellular aggregates or spheroids.

Human kidney cells were isolated using standard operating procedures for generating NKA, as described supra. Cells were expanded and sub-cultured through two passages prior to exposing to a low oxygen environment (2% O2) for 18 hours. After exposure, the cells were harvested and subjected to a two-step density gradient (7% and 16% w/v Optiprep) and centrifuged for 20 minutes at 800×g without brake. The resulting band formed between the 7 and 16% layer was collected and washed (B2, B3, B4). The cells were counted and viability assessed. Cellular aggregates or spheroids were generated by either culturing cells (20-30×10$^3$ cells/cm$^2$) in multi-well plates that were poly-HEMA coated to prevent attachment and placed on an orbital rotator in the incubator for 24 hrs (FIG. 30A). Alternatively, banded cells were resuspended in 75 mls of kidney growth medium at a concentration of 1×10$^6$ cells per ml and placed into a 125 ml spinner flask (BD) onto a magnetic stirrer (4-40 rpm) inside an incubator at 37° C./5% CO$_2$ (FIG. 30B). The cells were left to self aggregate to generate spheroids for 24-48 hours prior to assaying for phentotypic changes (FIG. 31). The cells can either be assayed within the spinner flasks or can be transferred to smaller poly-HEMA coated mutliwell plates, which maintain spheroids, for the assay(s). Any number of suitable assays are performed to measure phenotypic changes, function, viability, and apoptosis. Table 7 provides exemplary assays and the corresponding results.

TABLE 7

Examples of Functional Markers on Kidney Spheroids

Figure 36:
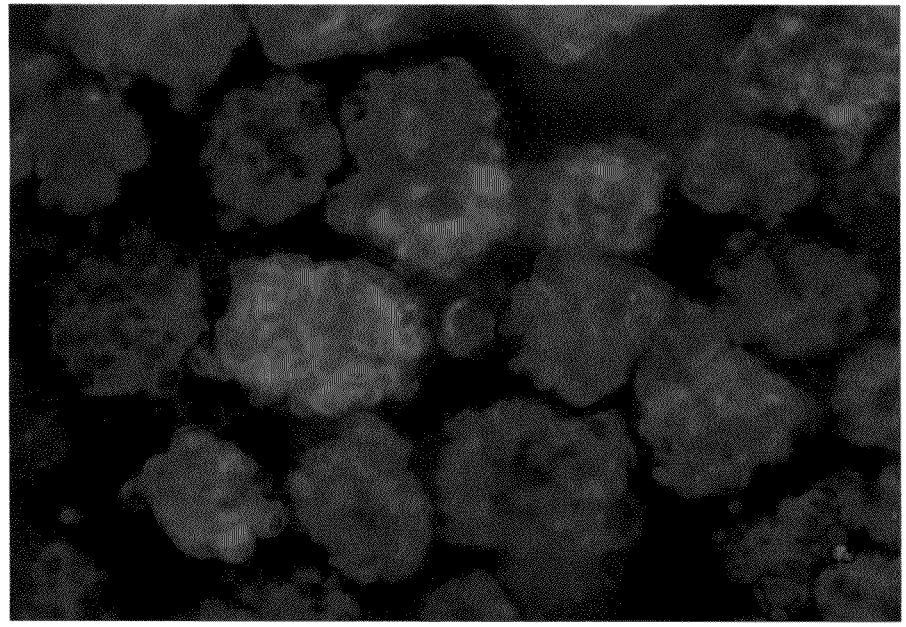
FIG. 36 depicts cellular aggregates—Organic Ion Transporter 1 (OAT1) red; nucleus blue.
Figure 37:
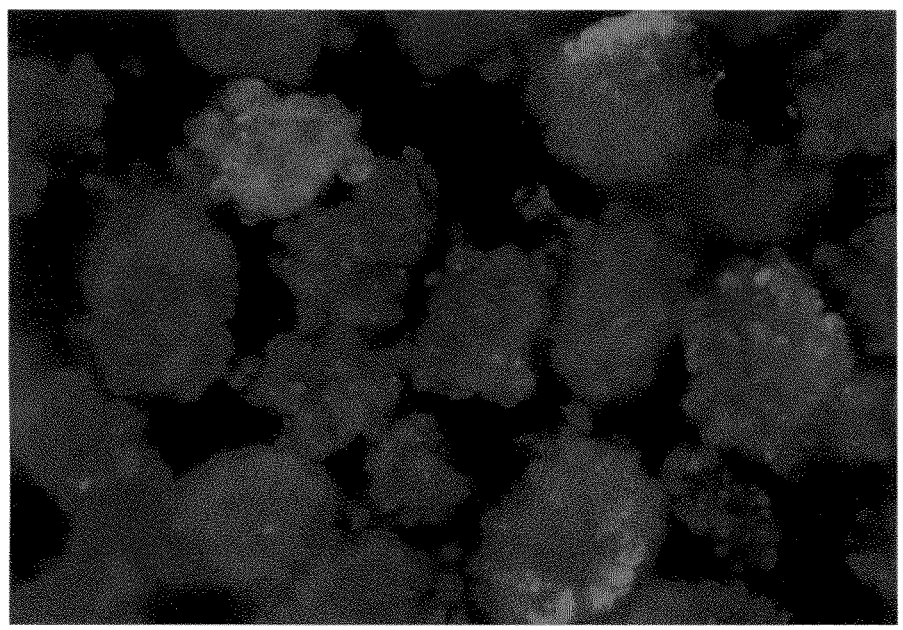
FIG. 37 depicts cellular aggregates—Cubilin red; nucleus blue.

| Marker | Function |
|---|---|
| NKCC2 (FIG. 32) | Expressed in kidney where active reabsorbtion of sodium chloride is mediated |
| GGT-1 (FIG. 33) | GGT-1 initiates extracellular glutathione breakdown (GSH) |
| Aqp-1 (FIG. 34) | Proximal tubule marker associated with water transport |
| LAP-3 (FIG. 35) | Involved in the processing and turnover of intracellular proteins and amino acids |
| OAT-1 (FIG. 36) | Important in transporting anionic substrates and removing toxins |
| Cubilin (FIG. 37) | Functionally import when bound to Megalin required for internalization of cubilin bound ligands such as Albumin, vitamin B12, an apolipoprotein A1 |

What is claimed is:

1. An injectable formulation comprising bioactive cells and a temperature-sensitive cell-stabilizing biomaterial, wherein the cell-stabilizing biomaterial
   consists of a hydrogel having a solid-to-liquid transitional state between 8° C. and ambient temperature or above, and
   wherein the bioactive cells are suspended in and are substantially uniformly dispersed throughout the volume of the cell-stabilizing biomaterial throughout the solid-to-liquid transitional state.

2. The formulation of claim 1, wherein the bioactive cells comprise renal cells.

3. The formulation of claim 1, wherein the hydrogel comprises gelatin.

4. The formulation of claim 3, wherein the gelatin is present in the formulation at about 0.5% to about 1% (w/v).

5. The formulation of claim 3, wherein the gelatin is present in the formulation at about 0.75% (w/v).

6. The formulation of claim 1, further comprising a cell viability agent.

7. The formulation of claim 6, wherein the cell viability agent comprises an agent selected from the group consisting of an antioxidant, an oxygen carrier, an immunomodulatory factor, a cell recruitment factor, a cell attachment factor, an anti-inflammatory agent, an immunosuppressant, an angiogenic factor, and a wound healing factor.

8. The formulation of claim 6, wherein the cell viability agent is an antioxidant.

9. The formulation of claim 8, wherein the antioxidant is 6-hydroxy-2,5,7,8-tetramethylchroman-2-carboxylic acid.

10. The formulation of claim 9, wherein the 6-hydroxy-2,5,7,8-tetramethylchroman-2-carboxylic acid is present at about 50 μM to about 150 μM.

11. The formulation of claim 9, wherein the 6-hydroxy-2,5,7,8-tetramethylchroman-2-carboxylic acid is present at about 100 μM.

12. The formulation of claim 7, wherein the cell viability agent is an oxygen carrier.

13. The formulation of claim 12, wherein the oxygen carrier is a perfluorocarbon.

14. The formulation of claim 7, wherein the cell viability agent is an immunomodulatory agent.

15. The formulation of claim 7, wherein the cell viability agent is an immunosuppressant.

16. An injectable formulation comprising bioactive renal cells, and a temperature-sensitive cell-stabilizing biomaterial, wherein the cell-stabilizing biomaterial consists of about 0.75% (w/v) gelatin and about 100 μM 6-hydroxy-2,5,7,8-tetramethylchroman-2-carboxylic acid, and wherein the cell-stabilizing biomaterial has
   (i) a substantially solid state at about 8° C. and below, and
   (ii) a substantially liquid state at about ambient temperature and above,
   wherein the biomaterial has a solid-to-liquid transitional state between 8° C. and ambient temperature or above, and
   wherein the bioactive renal cells are suspended in and substantially uniformly dispersed throughout the volume of the cell-stabilizing biomaterial throughout the transitional state.

17. The formulation of claim 16, wherein the substantially solid state is a gel state.

18. The formulation of claim 16, further comprising a cell viability agent.

19. The formulation of claim 18, wherein the cell viability agent comprises an agent selected from the group consisting of an antioxidant, an oxygen carrier, an immunomodulatory factor, a cell recruitment factor, a cell attachment factor, an anti-inflammatory agent, an angiogenic factor, and a wound healing factor.

20. The formulation of claim 19, wherein the cell viability agent is an oxygen carrier.

21. The formulation of claim 20, wherein the oxygen carrier is a perfluorocarbon.

22. The formulation of claim 19, wherein the cell viability agent is an immunomodulatory agent.

23. The formulation of claim 19, wherein the cell viability agent is an immunosuppressant.

24. The formulation of claim 1, further comprising biocompatible beads.

25. The formulation of claim 24, wherein the biocompatible beads are internally crosslinked.

26. The formulation of claim 25, wherein the crosslinked biocompatible beads have a reduced susceptibility to enzymatic degradation as compared to non-crosslinked biocompatible beads.

27. The formulation of claim 25, wherein the crosslinked biocompatible beads are carbodiimide-crosslinked beads.

28. The formulation of claim 27, wherein the carbodiimide is selected from the group consisting of 1-Ethyl-3-[3-dimethylaminopropyl] carbodiimide hydrochloride (EDC), DCC—N,N'-dicyclohexylcarbodiimide (DCC), and N,N'-Diisopropylcarbodiimide (DIPC).

29. The formulation of claim 27, wherein the carbodiimide is 1-Ethyl-3-[3-dimethylaminopropyl] carbodiimide hydrochloride (EDC).

30. The formulation of claim 26, wherein the crosslinked biocompatible beads comprise a reduced number of free primary amines as compared to non-crosslinked biocompatible beads.

31. The formulation of claim 25, wherein the biocompatible beads are seeded with the bioactive cells.

32. The formulation of claim 31, wherein the bioactive cells are renal cells.

33. The formulation of claim 25, further comprising additional biocompatible beads that comprise a temperature-sensitive biomaterial, wherein the temperature-sensitive biomaterial consists of a hydrogel that maintains
   (i) a substantially solid state at ambient temperature or below, and
   (ii) a substantially liquid state at about 37° C. or above.

34. The formulation of claim 33, wherein the temperature-sensitive biomaterial of the additional biocompatible beads comprises a solid-to-liquid transitional state between ambient temperature and about 37° C.

35. The formulation of claim 33, wherein the substantially solid state is a gel state.

36. The formulation of claim 33, wherein the hydrogel comprises gelatin.

37. The formulation of claim 36, wherein the additional biocompatible beads comprise gelatin at about 5% (w/v) to about 10% (w/v).

38. The formulation of claim 33, wherein the additional biocompatible beads are spacer beads.

39. The formulation of claim 38, wherein the spacer beads are not seeded with bioactive cells.

40. The formulation of claim 2, further comprising products secreted by a renal cell population.

41. The formulation of claim 40, wherein the products comprise paracrine factors.

42. The formulation of claim 40, wherein the products comprise endocrine factors.

43. The formulation of claim 40, wherein the products comprise juxtacrine factors.

44. The formulation of claim 40, wherein the products comprise vesicles.

45. The formulation of claim 44, wherein the vesicles comprise microvesicles.

46. The formulation of claim 44, wherein the vesicles comprise exosomes.

47. The formulation of claim 44, wherein the vesicles comprise a secreted product selected from the group consisting of paracrine factors, endocrine factors, juxtacrine factors, and RNA.

* * * * *